US008785434B2

(12) United States Patent
Hurt et al.

(10) Patent No.: US 8,785,434 B2
(45) **Date of Patent: *Jul. 22, 2014**

(54) ANTIVIRAL COMPOUNDS

(75) Inventors: Clarence R. Hurt, Los Altos, CA (US); Vishwanath Lingappa, San Francisco, CA (US); Beverly Freeman, Albany, CA (US); Andy Atuegbu, Dublin, CA (US); Anatoliy Kitaygorodskyy, San Francisco, CA (US)

(73) Assignee: Prosetta Antiviral Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/099,006

(22) Filed: May 2, 2011

(65) Prior Publication Data

US 2012/0157435 A1 Jun. 21, 2012

Related U.S. Application Data

(60) Provisional application No. 61/329,683, filed on Apr. 30, 2010, provisional application No. 61/421,225, filed on Dec. 9, 2010, provisional application No. 61/453,571, filed on Mar. 17, 2011, provisional application No. 61/468,614, filed on Mar. 29, 2011, provisional application No. 61/477,203, filed on Apr. 20, 2011, provisional application No. 61/479,351, filed on Apr. 26, 2011.

(51) Int. Cl.

| | |
|---|---|
| ***C07D 417/10*** | (2006.01) |
| ***C07D 417/14*** | (2006.01) |
| ***A61K 31/551*** | (2006.01) |
| ***A61K 31/5415*** | (2006.01) |

(52) U.S. Cl.
USPC .......................................... 514/224.8; 544/37

(58) Field of Classification Search
USPC .......................................... 544/37; 514/224.8
See application file for complete search history.

(56) References Cited

U.S. PATENT DOCUMENTS

| | | | |
|---|---|---|---|
| 4,141,668 | A | 2/1979 | Engel |
| 4,561,001 | A | 12/1985 | Gunn et al. |
| 4,604,458 | A | 8/1986 | Hung |
| 4,714,763 | A | 12/1987 | Theodoropulos |
| 5,344,928 | A | 9/1994 | Masuya et al. |
| 5,532,171 | A | 7/1996 | Motsenbocker et al. |
| 6,194,573 | B1 | 2/2001 | Burkett |
| 6,372,904 | B2 | 4/2002 | Burkett |
| 6,723,893 | B1 | 4/2004 | Brown et al. |
| 6,765,088 | B1 | 7/2004 | Korth et al. |
| 7,276,494 | B2 | 10/2007 | Brown et al. |
| 7,282,215 | B2 | 10/2007 | Chowdhary |
| 7,371,744 | B2 | 5/2008 | Brown et al. |
| 7,407,948 | B2 | 8/2008 | Griffiths et al. |
| 7,407,953 | B2 | 8/2008 | Brown et al. |
| 7,732,439 | B2 | 6/2010 | Brown et al. |
| 7,855,197 | B2 | 12/2010 | Brown et al. |
| 7,915,254 | B2 | 3/2011 | Brown et al. |
| 8,188,074 | B2 | 5/2012 | Brown et al. |
| 2002/0111501 | A1 | 8/2002 | Burkett |
| 2003/0022243 | A1 | 1/2003 | Kondejewski et al. |
| 2003/0104577 | A1 | 6/2003 | Lingappa et al. |
| 2003/0158204 | A1 | 8/2003 | Galey et al. |
| 2003/0162246 | A1 | 8/2003 | Endo et al. |
| 2006/0177813 | A1 | 8/2006 | Endo et al. |
| 2006/0264423 | A1 | 11/2006 | Wood et al. |
| 2007/0015211 | A1 | 1/2007 | Lingappa et al. |
| 2007/0128633 | A1 | 6/2007 | Zozulya et al. |
| 2007/0202537 | A1 | 8/2007 | Lingappa et al. |
| 2009/0023715 | A1 | 1/2009 | Brown et al. |
| 2009/0155761 | A1 | 6/2009 | Hansen et al. |
| 2010/0204215 | A1 | 8/2010 | Galey et al. |
| 2010/0211327 | A1 | 8/2010 | Hahner et al. |
| 2011/0028459 | A1 | 2/2011 | Brown et al. |
| 2011/0178071 | A1 | 7/2011 | Plattner et al. |
| 2011/0306576 | A1 | 12/2011 | Wainwright |
| 2012/0302557 | A1 | 11/2012 | Brown et al. |
| 2012/0328530 | A1 | 12/2012 | Wainwright |

FOREIGN PATENT DOCUMENTS

| | | | |
|---|---|---|---|
| DE | 196 40 758 | | 4/1998 |
| EP | 196515 | | 10/1986 |
| EP | 0510668 | | 10/1992 |
| GB | 2002517 | | 2/1979 |
| GB | 2 083 488 | | 3/1982 |
| GB | 2083488 | A * | 3/1982 |
| GB | 2373787 | | 10/2002 |
| KR | 10-2003-0031992 | | 4/2003 |
| WO | WO 90/13296 | | 11/1990 |
| WO | WO 98/22150 | | 5/1998 |
| WO | WO 98/28607 | | 7/1998 |
| WO | WO 99/25388 | | 5/1999 |
| WO | WO 02/24226 | | 3/2002 |

(Continued)

OTHER PUBLICATIONS

U.S. Appl. No. 11/798,776, filed May 16, 2007, Griffiths et al.
Amaral et al. Phenothiazines: potential management of Creutzfeldt-Jacob disease and its variants, Int. Journal of Antimicrobial Agents 18 (2001) 411-0417.
Andreani, F. et al., Ladder oligophenothiazines by direct thionation of N-Arylanilino Derivatives, (1991) J. Heterocyclic Chem., 28, 295-299.
Arhel et al., Host Proteins Involved in HIV Infection: New Therapeutic Targets, Biochimica et Biophysica Acta, vol. 1802: 313-321, 2010.
Baker-Wagner et al., "Evidence for Host Drug Targets Essential for Dengue Virus Capsid Formation", poster presented at the International Conference on Antiviral Research (ICAR) in San Francisco, CA, Apr. 25-Apr. 28, 2010.

(Continued)

*Primary Examiner* — Kahsay Habte
(74) *Attorney, Agent, or Firm* — Morgan, Lewis & Bockius LLP

(57) ABSTRACT

Compounds and methods for preventing and treating viral infections are provided. In some embodiments, novel compounds broad-spectrum antiviral activity are provided. In more specific embodiments, the compounds and methods are effective against viruses such as Venezuelan Equine Encephalitis, West Nile Virus, and respiratory viruses including the common cold.

41 Claims, 21 Drawing Sheets

(56) References Cited

FOREIGN PATENT DOCUMENTS

| | | |
|---|---|---|
| WO | WO 02/055720 | 7/2002 |
| WO | WO 02/075318 | 10/2002 |
| WO | WO 02/096896 | 12/2002 |
| WO | WO 2004/033628 | 4/2004 |
| WO | WO 2005/019828 | 3/2005 |
| WO | WO 2005/054217 | 6/2005 |
| WO | WO 2006/032847 | 3/2006 |
| WO | WO 2006/032879 | 3/2006 |
| WO | WO 2006/034219 | 3/2006 |
| WO | WO 2007/038201 | 4/2007 |
| WO | WO 2007/086995 | 8/2007 |
| WO | WO 2007/110627 | 10/2007 |
| WO | WO 2007/110629 | 10/2007 |
| WO | WO 2007/110630 | 10/2007 |
| WO | WO 2008/007074 | 1/2008 |
| WO | WO 2008/124550 | 10/2008 |
| WO | WO 2008/155533 | 12/2008 |
| WO | WO 2009/044127 | 4/2009 |
| WO | WO 2010/067078 | 6/2010 |
| WO | WO 2010/097626 | 9/2010 |
| WO | WO 2011/114137 | 9/2011 |
| WO | WO 2012/107706 | 8/2012 |

OTHER PUBLICATIONS

Bewley, G.C.: cDNA and deduced amino acid sequence of murine Cu—Zn superoxide dismutase, Nucleic Acids Research Mar. 25, 1988, vol. 16 No. 6, p. 2728.

Bieniasz, P., Restriction Factors: a Defense Against Retroviral Infection, Trends in Microbiology, vol. 11: 286-291, 2003.

Chang, T.W. et al., Photodynamic inactivation of herpesvirus hominins by methylene blue (38524). (1975) Proc Soc Exp Biol Med vol. 148 pp. 291-293.

Cheng Ng C C: Novel common structural feature among several classes of antimalarial agents, Journal of Pharmaceutical Sciences, American Pharmaceutical Association, Washington, US, val. 63, No. 2, Feb. 1, 1974, pp. 307-310, XP009132753, ISSN: 0022-3549.

Cobo, M.F., Photodynamic inactivation of Junin virus, (1986) Med. Microbiol. Immunol., 175, 67-69.

Coetzer et al., Erythrocyte Membrane Proteins in Hereditary Glucose Phosphate Isomerase Deficiency, J. Clinical Investigation 63 (4): 552-561 (1979), abstract only.

Creed et al., Ground and excited state properties of some new highly water soluble N-substituted thiazine dyes for photogalvanic applications, J. Chem. Soc., Chem. Commun., 1983, 1521-1523.

Dooher et al., Cell-Free Systems for Capsid Assembly of Primate Lentiviruses from Three Different Lineages, The Journal of Medical Primatology, vol. 33: 272-280, 2004.

Feigenbaum, J., Receptor inactivation by dye-neuropeptide conjugates: 1. The synthesis of Cys-containing dye-neuropeptide conjugates., Peptides, vol. 17, No. 6, pp. 991-994, 1996.

Francis et al., "Efficacy of a Small Molecule Inhibitor of Ebola Capsid Assembly in an Animal Model", poster presented at the International Conference on Antiviral Research (ICAR) in San Francisco, CA, Apr. 25-Apr. 28, 2010.

Haurum J.S., Recombinant polyclonal antibodies: the next generation of antibody therapeutics?, Drug Discovery Today, 11(13/14), Jul. 2006.

Karpuj et al., "Small Molecule Therapeutics of Viruses of Families Bunyaviridae and Arenaviridae", poster presented at the International Conference on Antiviral Research (ICAR) in San Francisco, CA, Apr. 25-Apr. 28, 2010.

Khattab, M., Targeting Host Factors: a Novel Rationale for the Management of Hepatitis C Virus, World Journal of Gastroenterology, vol. 15: 3472-3479, 2009.

Klein et al., HIV Gag-leucine zipper chimeras form ABCE1-containing intermediates and RNase-resistant immature capsids similar to those formed by wild-type HIV-1 Gag, The Journal of Virology, vol. 85:7419-35, 2011.

Klein et al., Identification of Residues in the Hepatitis C Virus Core Protein That Are Critical for Capsid Assembly in a Cell-Free System., Journal of Virology, vol. 79: 6814-6826, 2005.

Klein et al., Unique Features of Hepatitis C Virus Capsid Formation Revealed by De Novo Cell-Free Assembly, Journal of Virology, vol. 78: 9257-9269, 2004.

Komano et al., The Interaction of HIV-1 with the Host Factors., Japanese Journal of Infectious Diseases, vol. 58: 125-130, 2005.

Lambrecht, Rapid inactivation of HIV-1 in single donor preparations of human fresh frozen plasma by methylene blue/light treatment, Biologicals (1994) 22, 227-231.

Lawrason et al., Correlation between the mean corpuscular volume and reticulocytosis in phenlhydrazine anemia in swine, Blood 4 : 1256-1263 (1949).

Lingappa et al., "Overlap in Virus Specificity Leads to the Discovery of Small Molecules Active Against Rabies Virus, Monkey Pox Virus and Cytomegalovirus", poster presented at the International Conference on Antiviral Research (ICAR) in San Francisco, CA, Apr. 25-Apr. 28, 2010.

Lingappa et al., "Cell-free Protein Synthesizing Systems as Tools for Discovery of Drugs Inhibiting Viral Capsid Assembly", poster presented at the International Conference on Antiviral Research (ICAR) in San Francisco, CA, Apr. 25-Apr. 28, 2010.

Lingappa et al., "Small Molecule Inhibitors of De Novo Cell-free Capsid Assembly Effective Against Flaviridae and Togaviridae", poster presented at the International Conference on Antiviral Research (ICAR) in San Francisco, CA, Apr. 25-Apr. 28, 2010.

Lingappa et al., A Eukaryotic Cytosolic Chaperonin Is Associated with a High Molecular Weight Intermediate in the Assembly of Hepatitis B Virus Capsid, a Multimeric Particle., The Journal of Cell Biology, vol. 125: 99-111, 1994.

Lingappa et al., A Multistep, ATP-Dependent Pathway for Assembly of Human Immunodeficiency Virus Capsids in a Cell-Free System, The Journal of Cell Biology, vol. 136: 567-581, 1997.

Lingappa et al., Comparing Capsid Assembly of Primate Lentiviruses and Hepatitis B Virus Using Cell-Free Systems., Virology, vol. 333: 114-123, 2005.

Lingappa et al., Recent Insights into Biological Regulation from Cell-Free Protein-Synthesizing Systems., The Mount Sinai Journal of Medicine, vol. 72: 141-160, 2005.

Lingappa, Jr. et al., A Eukaryotic Cytosolic Chaperonin is Associated with a High Molecular Weight Intermediate in the Assembly of Hepatitis B Virus Capsid, a Multimeric Particle, The Journal of Cell Biology, Apr. 1994, vol. 125. No. 1. pp. 99-111.

Loach, Thin-layer chromatographic separation of methylene blue and related thiazine dyes, J.Chromatography, 60 (1971) 119-126.

Long, Experimental Anemia Produced by Phenylhydrazine Derivatives, J. Clinical Investigation 11(4): 329-339 (1926).

Lunsden et al., The Kinetics of Hematopoiesis in the Light Horse III. The Hematological Response to Hemolytic Anemia, Can. J. Comp. Med. 39 : 32-339 Jul. 1975.

Mascarenhas et al., The Capsid Protein of Human Immunodeficiency Virus: Interactions of HIV-1 Capsid with Host Protein Factors., FEBS Journal, vol. 276: 6118-6127, 2009.

Mellish et al., In vitro photodynamic activity of a series of methylene blue analogues, Photochemistry and Photobiology, 2002, 75(4): 392-397.

Motsenbocker et al Photochemistry and Photobiology. vol. 58, No. 5, pp. 648-652, 1993.

Motsenbocker, et al., Establishment of the Optically Pumped Chemiluminescence Technique for Diagnostics, Anal. Chem. 1993, 65,403-400.

Moura et al, 3,7-Bis(dialkylamino)phenothiazin-5-ium Derivatives: Biomedical Applications and Biological Activity, Current Drug Targets, 2003, vol. 4, No. 2.

Moura, J.C.V.P., Synthesis and Evaluation of Phenothiazine Singlet Oxygen Sensitizing Dyes for Application in Cancer Phototherapy, (1997) Phosphorus, Sulfur Silicon, vol. 120 & 121, pp. 459-460.

Muller-Breitkreutz et al., Hepatitis C and Human Immunodeficiency Virus RNA Degradation by Methylene Blue/Light Treatment of Human Plasma, Journal of Medical Virology 56:239-245 (1998).

Palacios et al., Panmicrobial oligonucleotide array for diagnosis of infectious diseases, Emerging Infectious Diseases, vol. 13 No. 1, p. 73-81, Jan. 2007.

(56) References Cited

OTHER PUBLICATIONS

Papin et al., Methylene blue photoinactivation abolishes West Nile virus infectivity in vivo, Antiviral Research, Elsevier Science BV., Amsterdam, NL, vol. 68, No. 2, Nov. 1, 2005, pp. 84-87.
Pardo C A et al., Superoxide dismutase is an abundant component in cell bodies, dendrites, and axons of motor neurons and in a subset of other neurons, Proceedings of the National Academy of Sciences of the United States of America Feb. 14, 1995, vol. 92, No. 4, pp. 954-958.
Petsch et al., "Discovery of Novel Small Molecule Inhibitors of Multiple Influenza-A Strains in Vivo", poster presented at the International Conference on Antiviral Research (ICAR) in San Francisco, CA, Apr. 25-Apr. 28, 2010.
Rakhit Rishi et al., An immunological epitope selective for pathological monomer-misfolded SOD1 in ALS, Nature Medicine Jun. 2007, vol. 13, No. 6, pp. 754-759.
Rakhit Rishi et al., Monomeric Cu, Zn-superoxide dismutase is a common misfolding intermediate in the oxidation models of sporadic and familial amyotrophic lateral sclerosis, The Journal of Biological Chemistry Apr. 9, 2004, vol. 279, No. 15, pp. 15499-15504.
Ray Soumya S. et al. Small-molecule-mediated stabilization of familial amyotrophic lateral sclerosis-linked superoxide dismutase mutants against unfolding and aggregation, Proceedings of The National Academy of Sciences of the United States of America Mar. 8, 2005, vol. 102, No. 10, pp. 3639-3644.
Reed et al., HIV-1 Gag co-opts a cellular complex containing DDX6, a helicase that facilitates capsid assembly, The Journal of Cell Biology, vol. 198(3):439-56, 2012.
Robuschi, L. Sperimentale (1940) 94, 99-124.
Rosenberg et al., Messenger RNA Loses the Ability to Direct in Vitro Peptide Synthesis following incubation with Cisplatin, Molecular Pharmacology 33 (6): 611-616 (1988).
Shapira et al., A Physical and Regulatory Map of Host-Influenza Interactions Reveals Pathways in H1N1 Infection, Cell, vol. 139: 1255-1267, 2009.
Sherman L. et al., Nucleotide Sequence and Expression of Human Chromosome 21-encoded superoxide Dismutase MRNA, Proceedings of the National Academy of Science, Washington, DC, US, vol. 80, Sep. 1983, pp. 5465-5469.
Singh et al., Effect of Mutations in Gag on Assembly of Immature Human Immunodeficiency Virus Type 1 Capsids in a Cell-Free System, Virology, vol. 279: 257-270, 2001.
Stertz et al., Human host factors required for influenza virus replication, Nature. Feb. 11, 2010;463(7282):813-7.
Stremlau, S., Why Old World Monkeys Are Resistant to HIV-1, Science, vol. 318: 1565-1566, 2007.
Swartz, M.R. et al., Inactivation of herpes simplex virus with methylene blue, light, and electricity, (1979) Proc Soc Exp Biol Med 161(2) 204-209.
Tai M M et al., Conformation specific antibodies directed against the Bovine Prothrombin Calcium Complex, Journal of Biological Chemistry, vol. 255, No. 7, 1980, pp. 2790-2795.
Valenty, Monolayer films of surfactant derivatives of methylene blue, Journal of Colloid and Interface Science, vol. 68, No. 3, Mar. 1, 1979.
Visalli et al., DNA Encapsidation as a Target for Anti-Herpesvirus Drug Therapy, Antiviral Research, vol. 59: 73-87, 2003.
Wagner et al., Factors affecting virus photoinactivation by a series of phenothiazine dyes, Photochem Photobiol. Mar. 1998;67(3):343-9.
Wainwright et al., Methylene blue derivatives—suitable photoantimicrobials for blood product disinfection, International Journal of Antimicrobial Agents 16 (2000) 381-394.
Wainwright Mark, Richard M. Giddens, Phenothiazinium photosensitisers: choices in synthesis and application, Dyes and Pigments 57 (2003) 245-257.
Wang et al. Microarray-based detection and genotyping of viral pathogens, PNAS, vol. 99, No. 24, p. 15687-15692, Nov. 26, 2002.
Zimmerman et al., Identification of a Host Protein Essential for Assembly of Immature HIV-1 Capsids, Nature, vol. 415: 88-92, 2002.

* cited by examiner

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | 0.01-0.2 | | | | | | | | | | | | | | <0.1 | | | |
|  | 0.1 | 2.5-10 | <0.16 | 0.16-0.63 | 0.63-2.5 | 0.16-0.63 | <1 | | 3-10 | | | | <1 | | <0.01 | | <2.5 | |
|  | | | | | | | | | | | | | | | | | | |
|  | | | | | | | | | | | | | | | | | | |
|  | 20 | | | | | | <1 | >7.5 | | | | | | | <1 | | | |
|  | 0.2-0.5 | | | | | | | >0.5 | | | | | | | <1 | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | 0.1- 0.2 | | | | | | | | | | | | | | <0.1 | | | 1.25-5 |
|  | 5-20 | | | | | | <1 | >20 | | | | | | | <1 | | | |
|  | 0.1- 0.16 | 2.5-10 | <0.15 6 | 0.63- 2.5 | >10 | <0.15 6 | 1-2.5 | | >7.5 | 0.2-1 | | | <1 | | <1 | | | <0.02 |
|  | 0.5- 2.5 | | | | | | | | | | | | | | | | | 0.02- 0.08 |
|  | 0.1- 0.5 | | | | | | | | | | | | | | | | | 0.078- 0.31 |
|  | >20 | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | <2.5 | | | | | | 1-4 | | 0.6-2 | >10 | | | 1-7.5 | | 1-7.5 | | <10 | |
|  | 0.5-2.5 | | | | | | 1-2 | | 0.6-2 | >10 | | | >7.5 | | | | | 0.31-1.25 |
|  | | | | | | | 7.5-20 | | | | | | >20 | | | | | |
|  | 20* | | | | | | 7.5-20* | | | | | | >20 | | | | | |
|  | <10 | | | | | | | >1 | | | | | 1-5 | | <1 | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | 2.5-10 | | | | | | | >1 | | | | | >10 | | >10 | | | |
|  | <20 | | | | | | | >20 | | | | | >20 | | >20 | | | |
|  | | | | | | | | | | | | | | | | | | |
|  | <0.4 | | | | | | | | | | | | | | | | | |
|  | | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | 1-20 | | | | | | | 7.5-20 | | | | | | | | | | |
|  | <5 | | | | | | | | | | | | | | <1 | | | |
|  | <5 | | | | | | | | | | | | | | <1 | | | |
|  | <5 | | | | | | | | | | | | | | | | | |
|  | >20 | | | | | | | | | | | | | | | | | |
|  | <0.8 | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | <20 | | | | | |
|  | <20 | | | | | | | | | | | | | | | | | |
|  | <20 | | | | | | | | | | | | | | | | | |
|  | <0.1 | | | | | | | | | | <0.5 | | <2 | | | | | |
|  | <2.4 | | | | | | | | | | | | | | | | | |
|  | >1.2 | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | <10 | | | | 1-5 | | | |
|  | | | | | | | | | | | | | | | | | | |
|  | >20 | | | | | | | | | | | | >20 | | | | | |
|  | <20 | | | | | | | | | | | | | | | | | |
|  | <1.2 | | | | | | | | | | | | <20 | | | | | |
|  | <2.4 | | | | | | | | | | | | <10 | | | | | |

| Structure | Flu | ADV | HCoV | HSV | RHINV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | <2.4 | | | | | | | | | | | | | | | | | |
|  | <20 | | | | | | | | | | | | | | | | | |
|  | <0.6 | | | | | | | | | | | | | | | | | |
|  | <2.4 | | | | | | | | | | | | | | | | | |
|  | <5 | | | | | | | | | | | | | | | | | |
|  | <0.5 | | | | | | 0.25-2.5 | 1-3.2 | | | | | <10 | | | | | 0.08-0.31 |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | 0.5* | | | | | | 0.25-1 | 1-3.2 | | | | | <20 | | | | | 0.08-0.31 |
|  | 0.1-2.4 | | | | | | 0.25-1 | >1 | | | | | <2 | | | <0.5 | | 0.078-0.31 |
|  | <10 | | | | | | | | | | | | | | | | | |
|  | <5 | | | | | | | | | | | | | | | | | |
|  | <2.4 | | | | | | | | | 0.2-1 | <0.04 | 0.2-0.75 | <1 | 0.2-0.75 | | | | |
|  | <0.5 | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
| | <5 | | | | | | | | | | | | | | | | | |
|  | 1-5 | | | | | | 2.5-10 | | 0.2-0.6 | 1-5 | <7.5 | | 1-5 | | | | | 0.02-0.078 |
|  | <1 | | | | | | | | | | <20 | | 1-7.5 | | | | | |
|  | <0.8 | | | | | | | | | | | | | | | | | |
|  | <0.8 | | | | | | | | | | | | | | | | | |
|  | | | | | | | | | | | <20 | | >20 | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | >20 | >10 | | | | | | | | |
|  | 1* | | | | | | | | | 0.2-1 | | | | | | | | 0.078-0.31 |
|  | | | | | | | | | | | | | | | | | | |
|  | | | | | | | | | | | | | | | | | | |
|  | | | | | | | | | | | | | | | | | | |
|  | | | | | | | | | | | | | | | | | | 1.25-5 |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | <1 | | | | | | | | | | | | | | <0.5 | | | |
|  | <0.2 | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | | | | | | | | | | | | | | | | | | |
|  | 0.2-1 | | | | | | 0.25-0.5 | | | | | | | | | | | |
|  | <1 | | | | | | 1-2.5 | | | | <20 | | <1 | | | | | |
|  | 0.04-0.2 | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | >5 | | | | | | | | >7.5 | | | | | | | | | |
|  | | | | | | | | | | | | | | | | | | |
|  | | | | | | | | | | | <20 | | <20 | | | | | |
|  | <0.2 | | | | | | | | | | <20 | | <1 | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | 0.2-1 | | | | | | | | | | | | | | | | | |
|  | | | | | | | | | | | | | | | | | | |
|  | | | | | | | | | | | | | | | | | | |
|  | | | | | | | | | | | <20 | | <20 | | | | | |
|  | | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
| AND Enantiomer  | | | | | | | | | | | | | | | | | | |
| AND Enantiomer  | | | | | | | | | | | | | | | | | | |
|  | <0.6 | | | | | | | | | <0.2 | <0.04 | <0.04 | <0.04 | <0.04 | | | | |
|  | <2.4 | | | | | | 0.35-0.5 | | >7.5 | 0.135-0.2 | <0.04 | 0.04-0.2 | <0.04 | 0.04 | | | | |
|  | | | | | | | | | | <0.2 | | | | | | | | |
|  | | | | | | | | | | >5 | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | 0.2-0.5 | >10 | | | | | | | | |
|  | 0.02-0.1 | | | | | | | | | <0.2 | | | | | | | | |
|  | | | | | | | >2.5 | | | 0.2-1 | | | | | | | | 0.078-0.31 |
|  | | | | | | | | | | <0.2 | | | | | | | | |
|  | | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | | | | | | | | | | | | | | | | | | |
|  | | | | | | | | | | | | | | | | | | |

| Structure | Flu | ADV | HCoV | HSV | RHNV | RSV | HCV | HIV | MPXV | RABV | DENV | EEEV | VEEV | WEEV | WNV | CKGV | EBOV | MARV |
|---|---|---|---|---|---|---|---|---|---|---|---|---|---|---|---|---|---|---|
|  | | | | | | | | | | | | | | | | | | |

ANTIVIRAL COMPOUNDS

1 CROSS-REFERENCE TO RELATED APPLICATIONS

This application claims priority under 35 U.S.C. §119(e) to provisional U.S. Patent Application Ser. No. 61/329,683 filed 30 Apr. 2010, 61/421,225 filed 9 Dec. 2010, 61/453,571 filed 17 Mar. 2011, 61/468,614 filed 29 Mar. 2011, 61/477,203 filed 20 Apr. 2011, and 61/479,351 filed 26 Apr. 2011, the entire disclosure of U.S. Patent Application Ser. No. 61/329,683 filed 30 Apr. 2010 is incorporated herein by reference in its entirety and for all purposes.

2 BACKGROUND OF THE INVENTION

2.1 Field of the Invention

The present invention provides compositions and methods for preventing and treating viral infections. The present invention thus has applications in the areas of medicine, pharmacology, virology, and medicinal chemistry.

2.2. The Related Art

Few good options are available for preventing or treating viral infections. The vast majority of antiviral drugs interfere with viral replication through the inhibition of transcription of the viral genome. Commonly these drugs inhibit a specific protein involved in viral genomic transcription, such as a polymerase or transcriptase; which often produces unwanted toxicity, since viruses depend largely on host factors for viral genomic replication. Moreover, given the highly specific nature of the target, small mutations in the viral genome are often sufficient to create viral strains that are resistant to chemotherapeutics. In addition, since the drugs inhibit active viral replication, they cannot eliminate virus that is latent or sequestered in the host; thus, patients are forced to take antivirals and endure their toxic effects for long periods if not indefinitely. Not surprisingly, patients on such regimens cannot continue treatment, and remain infected as well as providing a potentially continuing source of additional infections.

Thus there is a need for better antiviral chemotherapeutics and more effective strategies for identifying such chemotherapeutics. The need is especially urgent for those suffering from chronic and debilitating viral infections, such as human immunodeficiency virus (HIV) and hepatitis C (HCV), for which no good treatment exists for the reasons noted above.

But new viral threats are also on the horizon. The steady encroachment of civilization into the most remote regions of the globe has introduced the risk of exotic viral infections to the population at large. Each passing year brings an increasing number of reports of infections by hemorragic fevers, such as Ebola virus (EBOV), Marburg virus (Marburg), and Rift Valley Fever virus (RVFV). Still other viral infections can cause potentially debilitating effects, such as recurrent fevers, joint pain, and fatigue; these include: Punta Toro Virus (PTV), West Nile virus (WNV), chikungunya virus (CHK), Easter Equine Encephalitis virus (EEEV), Western Equine Encephalitis virus (WEEV), Lhasa virus (LASV), and Dengue virus (DENV).

By way of example, one of the additional "new" viruses (that is, new with respect to the industrialized world) is Venezuelan Equine Encephalitis virus (also called Venezuelan equine encephalomyelitis, VEEV). VEEV is a mosquito-borne viral disease of all equine species, including horses, asses (wild and domestic), and zebras. Equines infected with VEEV may show one or more of the following signs: fever, depression, loss of appetite weakness, and central nervous system disorders (lack of coordination, chewing movements, head pressing, "sawhorse" stance, circling, paddling motion of the limbs, and convulsions). In some cases, horses infected with VEEV may show no clinical signs before dying. The clinical signs of VEEV can be confused with those of other diseases that affect the central nervous system. These include eastern equine encephalitis, western equine encephalitis, African horse sickness, rabies, tetanus, and bacterial meningitis. VEE might also be mistaken for toxic poisoning. Definitive diagnosis can be made by isolating the virus in a laboratory or by testing blood for the presence of antibodies to the virus.

Humans also can contract this disease. Healthy adults who become infected by the virus may experience flu-like symptoms, such as high fevers and aches; and those having weakened immune systems, as well as the young and elderly, can become more severely ill or even die.

The virus that causes VEEV is transmitted primarily by mosquitoes that bite an infected animal and then bite and feed on another animal or human. The speed with which the disease spreads depends on the subtype of the VEEV virus and the density of mosquito populations. Enzootic subtypes of VEEV are diseases endemic to certain areas. Generally these serotypes do not spread to other localities. Enzootic subtypes are associated with the rodent-mosquito transmission cycle. These forms of the virus can cause human illness but generally do not affect equine health. Epizootic subtypes, on the other hand, can spread rapidly through large populations. These forms of the virus are highly pathogenic to equines and can also affect human health. Equines, rather than rodents, are the primary animal species that carry and spread the disease. Infected equines develop an enormous quantity of virus in their circulatory system. When a blood-feeding insect feeds on such animals, it picks up this virus and transmits it to other animals or humans. Although other animals, such as cattle, swine, and dogs, can become infected, they generally do not show signs of the disease or contribute to its spread.

Naturally occurring outbreaks of VEEV are rare. In 1936, VEEV was first recognized as a disease of concern in Venezuela following a major outbreak of equine encephalomyelitis. From 1936 to 1968, equines in several South American countries suffered devastating outbreaks. In 1969, the disease moved north throughout Central America, finally reaching Mexico and Texas in 1971. The highly pathogenic form of VEEV has not occurred in the United States since 1971. However, in 1993 an outbreak of VEEV in the State of Chiapas, Mexico, prompted the U.S. Department of Agriculture to temporarily increase its surveillance activities and tighten its quarantine requirements for equine species entering the United States from Mexico. During outbreaks, the most effective way to prevent further spread of disease is to quarantine infected equines. Controlling mosquito populations through pesticide treatments and eliminating insect-breeding sites will also enhance disease control. These measures should be accompanied by a large-scale equine immunization program. Equines in the United States should be vaccinated for VEE only when there is a serious threat that the disease could spread to this country.

Similar to VEE is West Nile virus (WNV), which was mentioned above. West Nile virus is named for a district in Uganda where the virus was first identified in humans in 1937. Outbreaks of the virus have occurred in a number of countries throughout Europe, the Middle East, Africa, Central Asia, and Australia, since that time. WNV was first detected in the Western Hemisphere in 1999, and since then the disease has spread across North America, Mexico, Puerto Rico, the Dominican Republic, Jamaica, Guadeloupe, and El Salvador. Symptoms range from a mild, flu-like illness (fever, headache, muscle and joint pain) and a red, bumpy rash, to meningitis. In rare cases those infected will develop encephalitis, which can include high fever, a stiff neck, disorientation, paralysis, convulsions, coma, and death in about ten percent of cases.

No cure or treatment is available for either VEEV or WNV, or the other viruses listed above; so public health experts emphasize prevention by avoiding areas where the disease has been detected or where disease vectors (usually mosquitoes) have been identified. However, that approach is becoming less reasonable as the world population grows. Moreover, some officials fear that one or both of these diseases, or other similar viruses in the toga- and flaviviridae, could be "weaponized" by a hostile government or terrorist organization to immobilize military personnel or important segments of the population in an attack.

To make matters still more complicated, the above-mentioned viral threats span almost all of the recognized viral families, including the bunyaviruses, flaviviruses, filoviruses, arenaviruses, and togaviruses. Since viral families are defined in significant part by their differences in mechanism for genomic replication, therapeutic strategies that are focused on inhibiting genomic replication will be inadequate for large outbreaks of new, and especially weaponized, viruses.

PCT Publication WO 2008/12450 discloses small molecule therapeutics having "broad spectrum" antiviral properties. Nevertheless, there remains an acute need to provide medicinal treatments for viral diseases. The present invention meets these and other needs.

3 SUMMARY OF EMBODIMENTS OF THE INVENTION

The present invention provides a variety of compounds, methods, and compostions for treating viral infections, especially those described above. Various embodiments of the invention include, but are not limited to, the following:

In a first aspect, the invention provides novel compounds having useful anti-viral activity. In one embodiment, the present invention provides compounds having the structure:

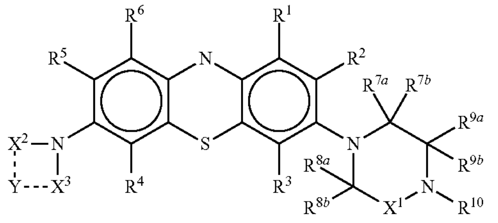

and their pharmaceutically acceptable salts, hydrates, and coordination compounds. $R^1$-$R^{9b}$ are selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl) alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuonyl, cycloalkylsulfonyl, aralkycarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl. $R^{10}$ is hydrogen or optionally substituted alkyl, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl. $X^1$ is $(CR^{11}R^{11'})_m$, wherein m is either 1 or 2 such that each of $R^{11}$ and $R^{11'}$, independently for each value of m, is selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl) alkylcarbonyloxy, alkylcarbonyl, arylcarbonyl, heteroarylcarbonyl, cycloalkylcarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl) alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuonyl, cycloalkylsulfonyl, aralkycarbonylthiooxy, carbonylythio, heteroaralkylcarbonylthio, (cycloalkyloxy)carbonylthio, (cycloheteroalkyl) alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl) iminoalkyl.

Y is optionally present; and when Y is present, Y is $NR^{12}$, O, S, SO, or $SO_2$, or a single or double bond between $X^2$ and $X^3$; $R^{12}$ is hydrogen or optionally substituted alkyl, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkyl sulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl; and $X^2$ and $X^3$ are $(CR^{13}R^{13})_n$ and $(CR^{14}R^{14})_o$ respectively, wherein each of n and o is independently either 1, 2, or 3 such that the sum n+o is either 3, 4, or 5, and independently for each value of the n and o methylene units of $X^2$ and $X^3$, each of $R^{13}$, $R^{13'}$, $R^{14}$, $R^{14'}$ is selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl. When Y is not present $X^2$ is $R^{15}$ and $X^3$ is $R^{16}$, where $R^{15}$ and $R^{16}$ are selected independently from the group consisting of: hydrogen and optionally substituted alkyl, alkylcarbonyl, arylcarbonyl, heteroarylcarbonyl, cycloalkycarbonyl, cycloheteroalkylcarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl.

In a more specific embodiment, the present invention provides a compound from the family of compounds just described wherein m is 1, such that $X^1$ is $(CR^{11}R^{11'})$, thereby defining $X^1$ as $(CR^{11a}R^{11b})$, said compound having the structure:

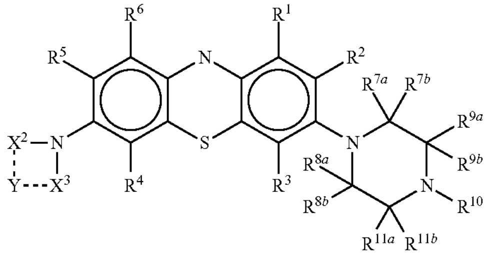

$R^{11a}$ and $R^{11b}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthioooxy, carbonylythio, heteroaralkylcarbonylthio, (cycloalkyloxy)carbonylthio, (cycloheteroalkyl) alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

In other embodiments Y is not present; such compounds have the structure:

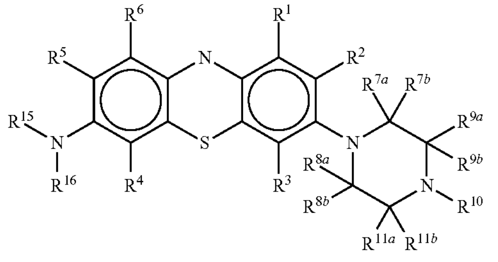

In still other embodiments Y is present; such compound have the structure:

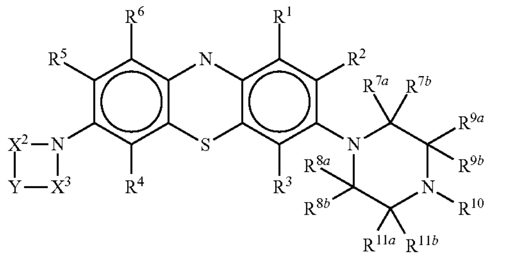

Yet other embodiments include those compounds in which each of n and o is 2, such that $X^2$ and $X^3$ have the form $(CR^{13}R^{13'})_2$ and $(CR^{14}R^{14'})_2$ respectively, defining thereby $X^2$ as $(CR^{13a}R^{13b})(CR^{13c}CR^{13d})$ and $X^3$ as $(CR^{14a}R^{14b})(CR^{14c}R^{14d})$, said compound having the structure:

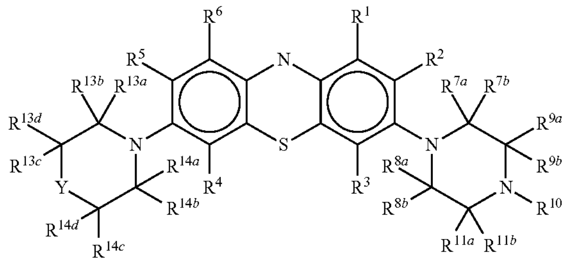

wherein $R^{13a}$-$R^{14d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

In still other embodiments, wherein m is 2, such that $X^1$ is $(CR^{11}R^{11'})_2$, thereby defining $X^1$ as $(CR^{11c}R^{11d})$, said compound having the structure:

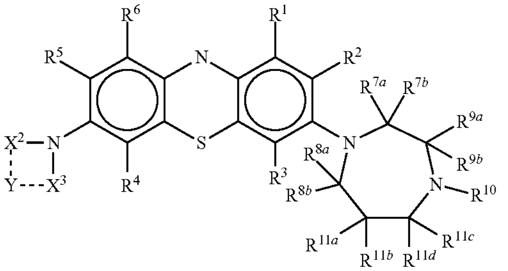

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

Other embodiments of the compounds just described include those, wherein Y is present; these compounds having the structure:

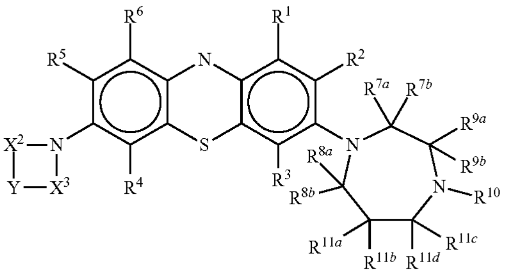

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)

alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

Other embodiments of the compounds just described include those, wherein Y is present; these compounds having the structure:

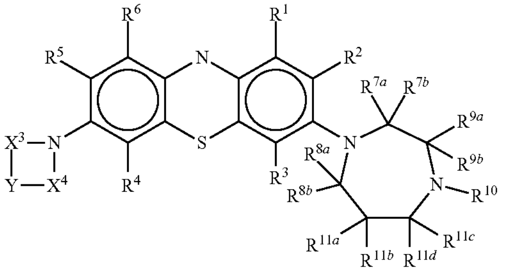

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthioooxy, carbonylythio, heteroaralkylcarbonylthio, (cycloalkyloxy)carbonylthio, (cycloheteroalkyl) alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

In another aspect, the present invention provides methods for treating a viral disease in a mammal afflicted with such disease, comprising administering to such mammal a therapeutically effective amount of the compound of the invention. In more specific embodiments, the viral disease is an etiological component of a respiratory syndrome selected from the group consisting of: bronchiolitis, the common cold, croup, influenza, and pneumonia.

4 BRIEF DESCRIPTION OF THE DRAWINGS

5 DETAILED DESCRIPTION OF SOME EMBODIMENTS OF THE INVENTION

5.1 Definitions

Figure 1A:
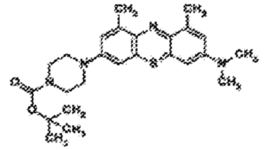
FIG. 1A is a table showing the anti-viral activities of some compounds of the invention as determined by the methods described herein.

The following terms are used herein as defined below unless specifically stated otherwise:

Optionally substituted refers to the replacement of hydrogen with a univalent or divalent radical. Suitable substitution groups include, for example, hydrooxyl, nitro, amino, imino, cyano, halo, thio, thioamido, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, alkylthio, aminoalkyl, cyanoalkyl, and the like as defined herein. The substitution group can itself be substituted. The group substituted onto the substitution group can be, for example, carboxyl, halo; nitro, amino, cyano, hydroxyl, loweralkyl, loweralkoxy, aminocarbonyl, —SR, thioamido, —$SO_3H$, —$SO_2R$ or cycloalkyl, where R is typically hydrogen, hydroxyl or loweralkyl. When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substitutents can be straight chain, branched or cyclic arrangements of covalently bonded carbon or heteroatoms.

Loweralkyl as used herein refers to branched or straight chain alkyl groups comprising one to ten carbon atoms that independently are unsubstituted or substituted, e.g., with one or more halogen, hydroxyl or other groups. Examples of loweralkyl groups include, but are not limited to, methyl, ethyl, propyl, isopropyl, n-butyl, t-butyl, n-hexyl, neopentyl, trifluoromethyl, pentafluoroethyl, and the like.

Alkylenyl refers to a divalent straight chain or branched chain saturated aliphatic radical having from 1- to 20 carbon atoms. Typical alkylenyl groups employed in compounds of the present invention are loweralkylenyl groups that have from 1 to about 6 carbon atoms in their backbone.

Alkenyl refers herein to straight chain, branched, or cyclic radicals having one or more double bonds and from 2 to 20 carbon atoms.

Alkynyl refers herein to straight chain, branched, or cyclic radicals having one or more triple bonds and from 2 to 20 carbon atoms.

Haloloweralkyl refers to a loweralkyl radical substituted with one or more halogen atoms.

Loweralkoxy as used herein refers to RO— wherein R is loweralkyl. Representative examples of loweralkoxy groups include methoxy, ethoxy, t-butoxy, trifluoromethoxy and the like.

Loweralkylhio as used herein refers to RS— wherein R is loweralkyl.

Alkoxyalkyl refers to the group -$alk_1$-O-$alk_2$, where $alk_1$ is alkylenyl or alkenyl, and $alk_2$ is alkyl or alkenyl.

Loweralkoxyalkyl refers to an alkoxyalkyl as defined above, where $alk_1$ is loweralkylenyl or loweralkenyl, and $alk_2$ is loweralkyl or loweralkenyl.

Aryloxyalkyl refers to the group alkylenyl-O-aryl. The term

Aralkoxyalkyl refers to the group alkylenyl-O-aralkyl, where aralkyl is a loweraralkyl.

Cycloalkyl refers to a mono- or polycyclic, loweralkyl substituent. Typical cycloalkyl substituents have from 3 to 8 backbone (i.e., ring) atoms in which each backbone atom is optionally substituted carbon. When used in context with cycloalkyl substituents, the term polycyclic refers herein to fused, non-fused cyclic carbon structures and spirocycles. Examples of cycloalkyl groups include, but are not limited to, cyclopropyl, cyclobutyl, cyclopentyl, cyclohexyl, adamantyl, bornyl, norbornyl, and the like.

Cycloheteroalkyl refers herein to cycloalkyl substituents that have from 1 to 5, and more typically from 1 to 4 heteroatoms (i.e., non-carbon atoms such as nitrogen, sulfur, and oxygen) in the ring structure, with the balance of atoms in the ring being optionally substituted carbon. Representative heterocycloalkyl moieties include, for example, morpholino, piperazinyl, piperidinyl, pyrrolidinyl, methylpryolidinyl, pyrrolidinone-yl, and the like.

(Cycloalkyl)alkyl and (Cycloheteroalkyl)alkyl refer to alkyl chains substituted with cycloalkyl and cycloheteroalkyl groups respectively.

Haloalkoxy refers to an alkoxy radical substituted with one or more halogen atoms. The term haloloweralkoxy refers to a loweralkoxy radical substituted with one or more halogen atoms.

Halo refers herein to a halogen radical, such as fluorine, chlorine, bromine, or iodine.

Aryl refers to monocyclic and polycyclic aromatic groups, or fused ring systems having at least one aromatic ring, having from 3 to 14 backbone carbon atoms. Examples of aryl groups include without limitation phenyl, naphthyl, dihydronaphthyl, tetrahydronaphthyl, and the like.

Aralkyl refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Heteroaryl refers herein to aryl groups having from one to four heteroatoms as ring atoms in an aromatic ring with the remainder of the ring atoms being aromatic or non-aromatic carbon atoms. When used in connection with aryl substituents, the term polycyclic refers herein to fused and non-fused cyclic structures in which at least one cyclic structure is aromatic, such as, for example, benzodioxozolo, naphthyl, and the like. Exemplary heteroaryl moieties employed as substituents in compounds of the present invention include pyridyl, pyrimidinyl, thiazolyl, indolyl, imidazolyl, oxadiazolyl, tetrazolyl, pyrazinyl, triazolyl, thiophenyl, furanyl, quinolinyl, purinyl, benzothiazolyl, benzopyridyl, and benzimidazolyl, and the like.

Amino refers herein to the group —$NH_2$. The term loweralkylamino refers herein to the group —NRR' where R and R' are each independently selected from hydrogen or loweralkyl. The term arylamino refers herein to the group —NRR' where R is aryl and R' is hydrogen, loweralkyl, aryl, or aralkyl. The term aralkylamino refers herein to the group —NRR' where R is aralkyl and R' is hydrogen, loweralkyl, aryl, or aralkyl. The terms heteroarylamino and heteroaralkylamino are defined by analogy to arylamino and aralkylamino.

Aminocarbonyl refers herein to the group —C(O)—$NH_2$. The terms loweralkylaminocarbonyl, arylaminocarbonyl, aralkylaminocarbonyl, heteroarylaminocarbonyl, and heteroaralkylaminocarbonyl refer to —C(O)NRR' where R and R' independently are hydrogen and optionally substituted loweralkyl, aryl, aralkyl, heteroaryl, and heteroaralkyl respectively by analogy to the corresponding terms above.

Thio refers to —SH. The terms loweralkylthio, arylthio, heteroarylthio, cycloalkylthio, cycloheteroalkylthio, aralkylthio, heteroaralkylthio, (cycloalkyl)alkylthio, and (cycloheteroalkyl)alkylthio refer to —SR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfonyl refers herein to the group —$SO_2$—. The terms loweralkylsulfonyl, arylsulfonyt, heteroarylsulfonyt, cycloalkylsulfonyt, cycloheteroalkylsulfonyt, aralkylsulfonyl, heteroaralkylsulfonyt, (cycloalkyl)alkylsulfonyt, and (cycloheteroalkyl-) alkylsulfonyl refer to —$SO_2$R where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Sulfinyl refers herein to the group —SO—. The terms loweralkylsulfinyl, arylsulfinyl, heteroarylsulfinyl, cycloalkylsulfinyl, cycloheteroalkylsulfinyl, aralkylsulfinyl, heteroaralkylsulfinyl, (cycloalkyl)alkylsulfinyl, and (cycloheteroalkyl)alkylsulfinyl refer to —SOR where R is optionally substituted loweralkyl, aryl, heteroaryl, cycloalkyl, cycloheteroalkyl, aralkyl, heteroaralkyl, (cycloalkyl)alkyl, and (cycloheteroalkyl) alkyl respectively.

Formyl refers to —C(O)H.

Carboxyl refers to —C(O)OH.

Carbonyl refers to the divalent group —C(O)—. The terms lower alkylcarbonyl, arylcarbonyl, hetero aryl carbonyl, cycloalkylcarbonyl, cycloheteroalkylcarbonyl, arallycarbonyl, hetero arallylcarbonyl, (cycloalkyl)alkylcarbonyl, and (cycloheteroalkyl)alkylcarbonyl refer to —C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Thiocarbonyl refers to the group —C(S)—. The terms lower alkylthiocarbonyl, arylthiocarbonyl, heteroarylthiocarbonyl, cycloalkylthiocarbonyl, cycloheteroalkylthiocarbonyl, aralkylthiocarbonyloxlthiocarbonyl, heteroaralkylthiocarbonyl, (cycloalkyl)alkylthio carbonyl, and (cycloheteroalkyl)alkylthiocarbonyl refer to —C(S)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonyloxy refers generally to the group —C(O)—O—. The terms loweralkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy refer to —C(O)OR, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Oxycarbonyl refers to the group —O—C(O)—. The terms loweralkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxy carbonyl, (cycloheteroalkyl)alkyloxy carbonyl refer to —O—C(O)R, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Carbonylamino refers to the group —NH—C(O)—. The terms loweralkylcarbonylamino, arylcarbonylamino, heteroarylcarbonylamino, cycloalkylcarbonylamino, cycloheteroalkylcarbonylamino, aralkylcarbonylamino, hetero aralkylcarbonylamino, (cyclo alkyl)alkylcarbonylamino, and (cycloheteroalkyl)alkylcarbonylamino refer to —NH—C(O)R—, where R is optionally substituted loweralkyl, aryl, heteroaryl, cycloalkyl, cycloheteroalkyl, aralkyl, heteroaralkyl, (cycloalkyl)alkyl, or (cycloheteroalkyl)alkyl respectively. In addition, the present invention includes n-substituted carbonylamino (—NR'C(O)R), where R' is optionally substituted loweralkyl, aryl, heteroaryl, aralkyl, or heteroaralkyl and R retains the previous definition.

Carbonylthio refers to the group —C(O)—S—. The terms loweralkylcarbonylthio, arylcarbonylthio, heteroarylcarbonylthio, cyclo alkylcarbonylthio, cycloheteroalkylcarbonylthio, aralkylcarbonylthio, heteroaralkylcarbonylthio, (cycloalkyl)alkylcarbonylthio, (cycloheteroalkyl)alkylcarbonylthio refer to —C(O)SR—, where R is optionally substituted loweralkyl, aryl, heteroaryl, cycloalkyl, cycloheteroalkyl, aralkyl, heteroaralkyl, (cycloalkyl)alkyl, and (cycloheteroalkyl)alkyl respectively.

Guanidino or Guanidyl refers to moieties derived from guanidine, $H_2N$—C(═NH)—$NH_2$. Such moieties include those bonded at the nitrogen atom carrying the formal double bond (the p-position of the guanidine, e.g., diaminomethyleneamino, (($H_2N$)$_2$—C═NH—) and those bonded at either of the nitrogen atoms carrying a formal single bond (the 1- or 3-positions of the guanidine, e.g., $H_2N$—C(═NH)—NH—). The hydrogen atoms at either nitrogen can be replaced with a suitable substituent, such as loweralkyl, aryl, or loweraralkyl.

Amidino refers to the moieties R—C(═N)—NR' (the radical being at the $N^1$ nitrogen) and R(NR')C═N— (the radical being at the $N^2$ nitrogen), where R and R' can be hydrogen, loweralkyl, aryl, or loweraralkyl.

Imino refers to the group —C(═NR)—, where R can be hydrogen or optionally substituted loweralkyl, aryl, heteroaryl, or heteroaralkyl respectively. The terms iminoloweralkyl, iminocycloalkyl, iminocycloheteroalkyl, iminoaralkyl, iminohetero aralkyl, (cycloalkyl)iminoalkyl, (cycloiminoalkyl)alkyl, (cycloiminoheteroalkyl)alkyl, and (cycloheteroalkyl)iminoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an imino group, respectively.

Oximino refers to the group —C(═NOR)—, where R can be hydrogen (hydroximino) or optionally substituted loweralkyl, aryl, heteroaryl, or heteroaralkyl respectively. The terms oximinoloweralkyl, oximinocycloalkyl, oximinocycloheteroalkyl, oximino aralkyl, oximinoheteroaralkyl, (cycloalkyl)oximinoalkyl, (cyclooximinoalkyl)alkyl, (cyclooximinoheteroalkyl)alkyl, and (cycloheteroalkyl)oximinoalkyl refer to optionally substituted loweralkyl, cycloalkyl, cycloheteroalkyl, aralkyl, heteroaralkyl, (cycloalkyl)alkyl, and (cycloheteroalkyl)alkyl groups that include an oximino group, respectively.

Methylene as used herein refers to an unsubstituted, monosubstituted, or disubstituted carbon atom having a formal $sp^3$ hybridization (i.e., —CRR'—, where R and R' are hydrogen or independent substituents).

Methine as used herein refers to an unsubstituted or substituted carbon atom having a formal $sp^2$ hybridization (i.e., CR= or =CR—, where R is hydrogen or a substituent).

5.2 Compounds and Methods of the Invention

In a first aspect, the present invention provides novel compounds having the having structure:

Figure 1

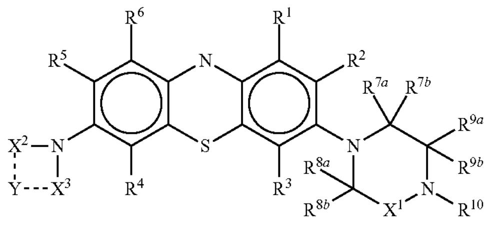

and its pharmaceutically acceptable salts, hydrates, and coordination compounds.

Figure 1A:
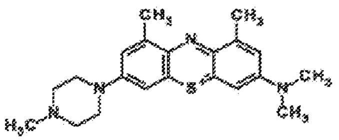
Figure 1A:
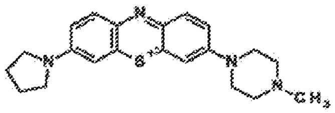
Figure 1A:
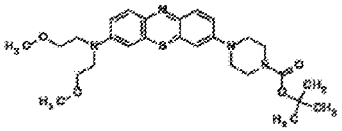
Figure 1A:
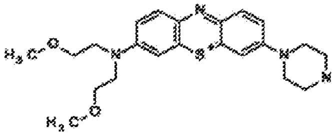
Figure 1A:
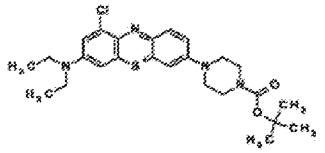
Figure 1B:
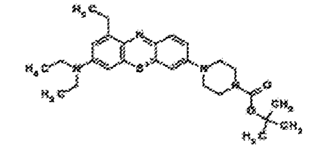
FIG. 1B is a table showing the anti-viral activities of some compounds of the invention as determined by the methods described herein.
Figure 1B:
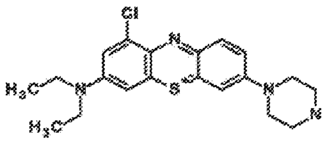
Figure 1B:
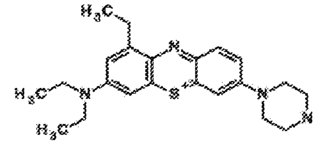
Figure 1B:
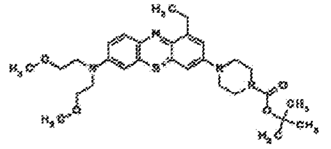
Figure 1B:
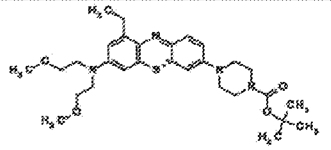
Figure 1B:
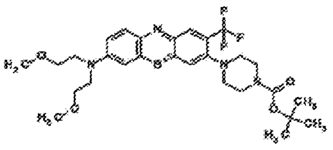
Figure 1C:
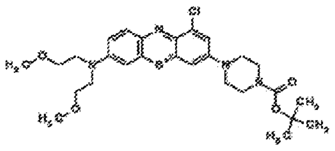
FIG. 1C is a table showing the anti-viral activities of some compounds of the invention as determined by the methods described herein.
Figure 1C:
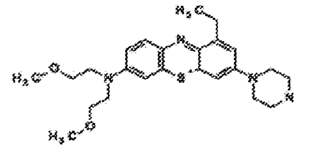
Figure 1C:
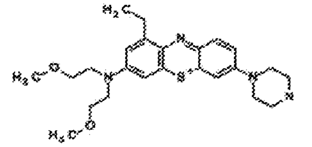
Figure 1C:
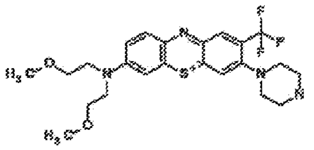
Figure 1C:
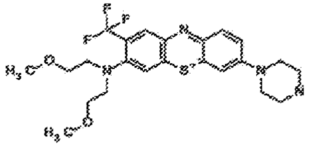
Figure 1C:
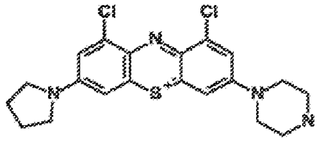
Figure 1D:
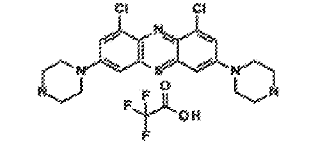
FIG. 1D is a table showing the anti-viral activities of some compounds of the invention as determined by the methods described herein.
Figure 1D:
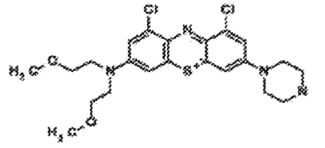
Figure 1D:
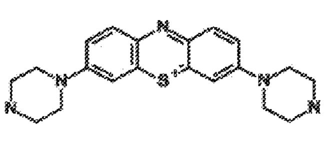
Figure 1D:
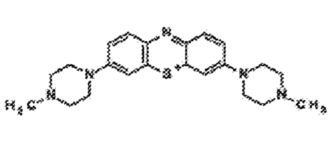
Figure 1D:
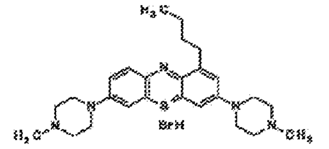
Figure 1D:
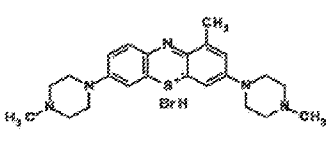
Figure 1E:
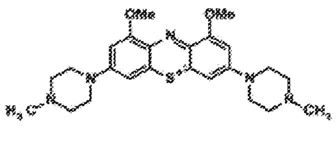
FIG. 1E is a table showing the anti-viral activities of some compounds of the invention as determined by the methods described herein.
Figure 1E:
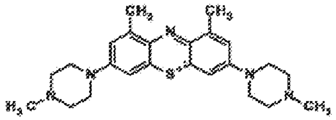
Figure 1E:
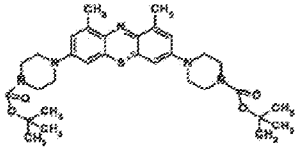
Figure 1E:
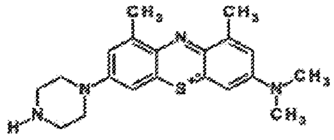
Figure 1E:
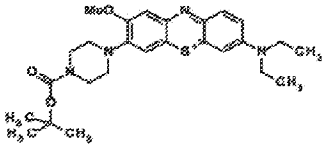
Figure 1E:
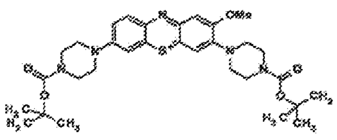
Figure 1F:
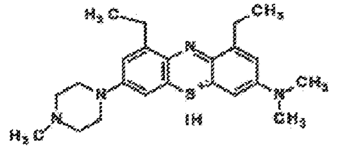
FIG. 1F is a table showing the anti-viral activities of some compounds of the invention as determined by the methods described herein.
Figure 1F:
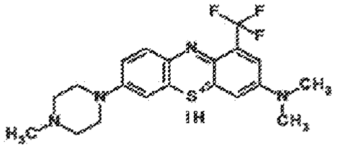
Figure 1F:
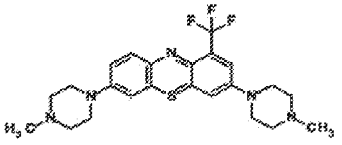
Figure 1F:
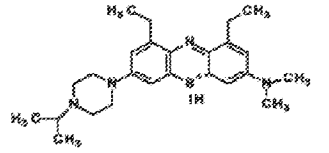
Figure 1F:
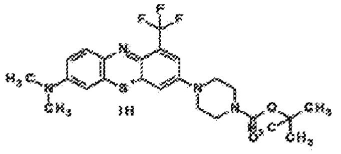
Figure 1F:
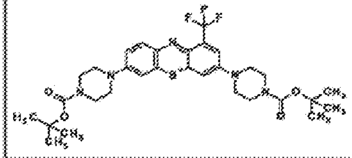
Figure 1G:
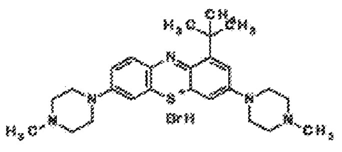
FIG. 1G is a table showing the anti-viral activities of some compounds of the invention as determined by the methods described herein.
Figure 1G:
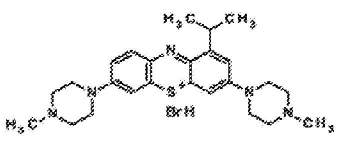
Figure 1G:
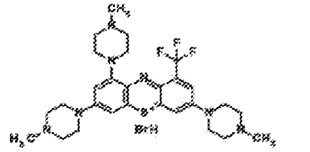
Figure 1G:
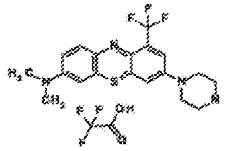
Figure 1G:
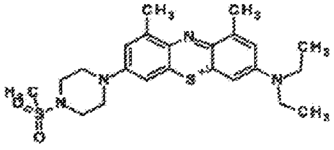
Figure 1G:
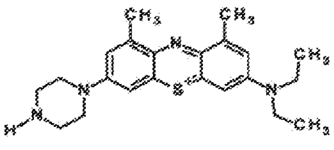
Figure 1H:
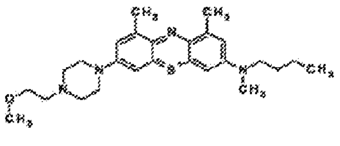
FIG. 1H is a table showing the anti-viral activities of some compounds of the invention as determined by the methods described herein.
Figure 1H:
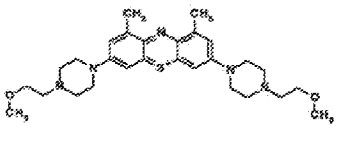
Figure 1H:
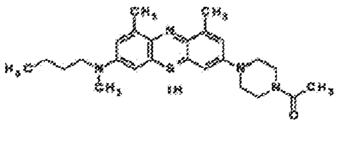
Figure 1H:
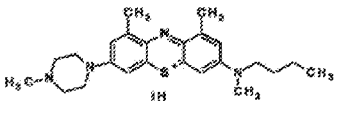
Figure 1H:
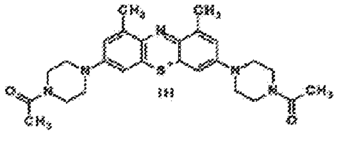
Figure 1H:
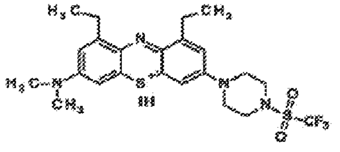
Figure 1I:
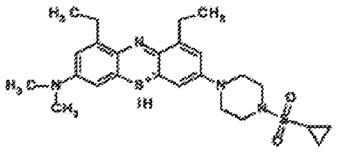
FIG. 1I is a table showing the anti-viral activities of some compounds of the invention as determined by the methods described herein.
Figure 1I:
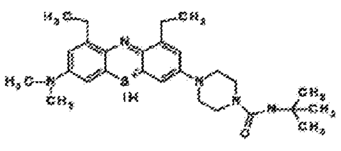
Figure 1I:
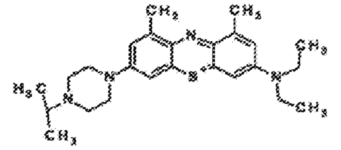
Figure 1I:
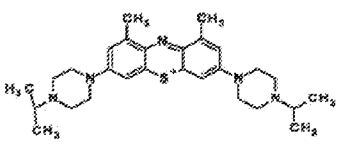
Figure 1I:
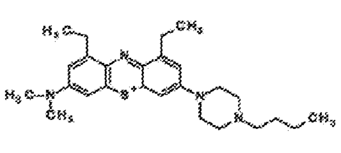
Figure 1I:
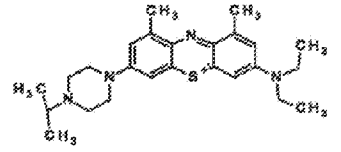
Figure 1J:
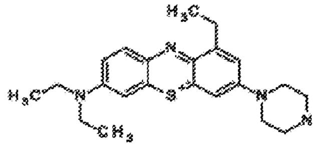
FIG. 1J is a table showing the anti-viral activities of some compounds of the invention as determined by the methods described herein.
Figure 1J:
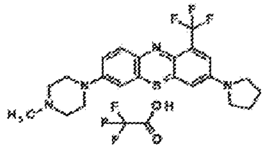
Figure 1J:
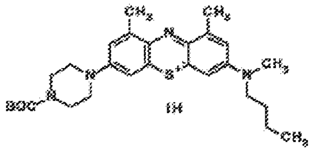
Figure 1J:
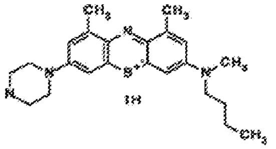
Figure 1J:
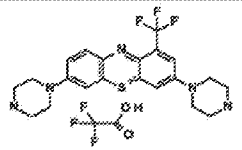
Figure 1K:
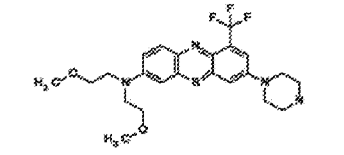
FIG. 1K is a table showing the anti-viral activities of some compounds of the invention as determined by the methods described herein.
Figure 1K:
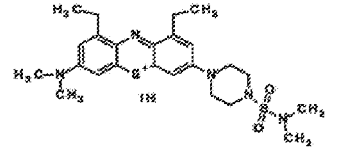
Figure 1K:
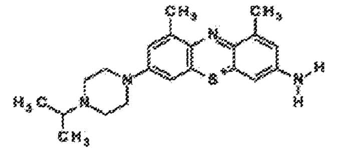
Figure 1K:
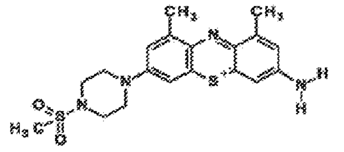
Figure 1K:
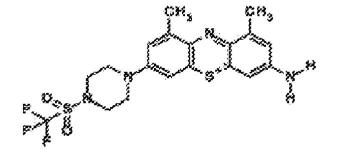
Figure 1K:
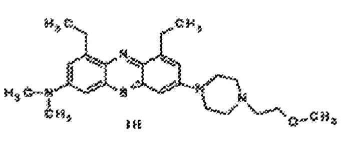
Figure 1L:
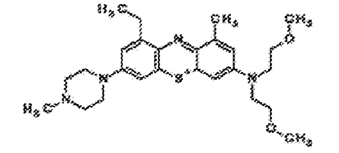
FIG. 1L is a table showing the anti-viral activities of some compounds of the invention as determined by the methods described herein.
Figure 1L:
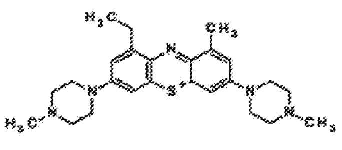
Figure 1L:
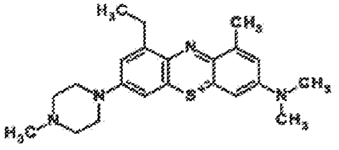
Figure 1L:
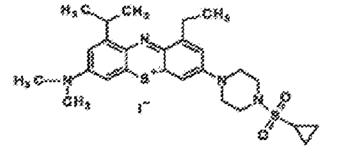
Figure 1L:
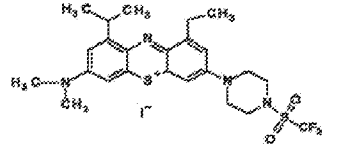
Figure 1L:
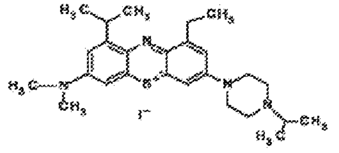
Figure 1M:
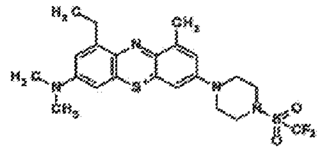
FIG. 1M is a table showing the anti-viral activities of some compounds of the invention as determined by the methods described herein.
Figure 1M:
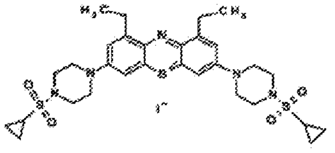
Figure 1M:
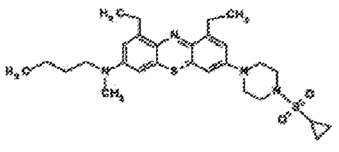
Figure 1M:
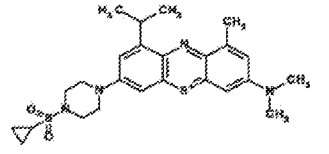
Figure 1M:
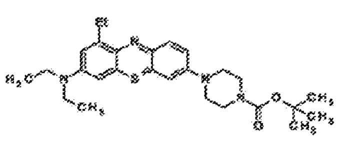
Figure 1M:
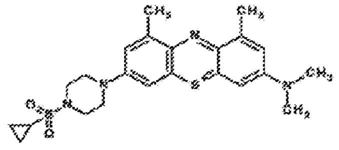
Figure 1N:
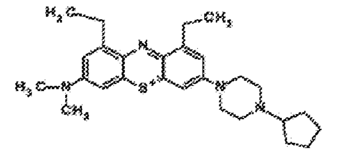
FIG. 1N is a table showing the anti-viral activities of some compounds of the invention as determined by the methods described herein.
Figure 1N:
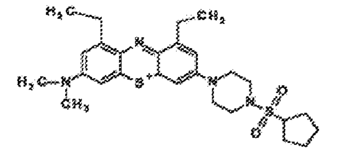
Figure 1N:
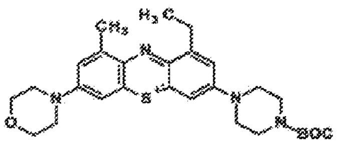
Figure 1N:
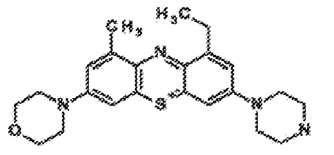
Figure 1N:
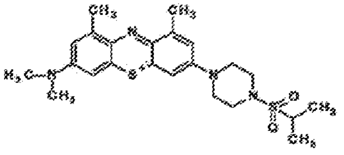
Figure 1N:
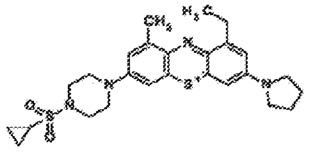
Figure 1O:
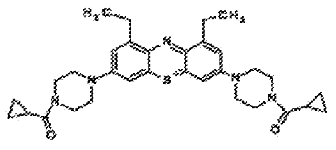
FIG. 1O is a table showing the anti-viral activities of some compounds of the invention as determined by the methods described herein.
Figure 1O:
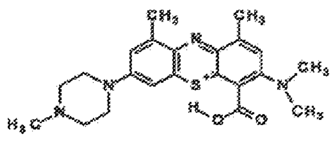
Figure 1O:
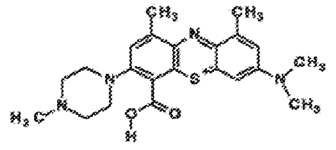
Figure 1O:
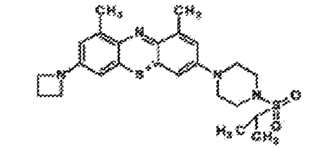
Figure 1O:
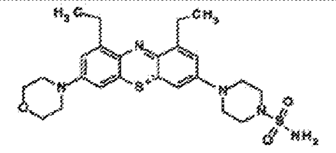
Figure 1O:
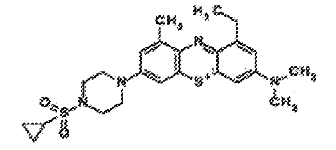
Figure 1P:
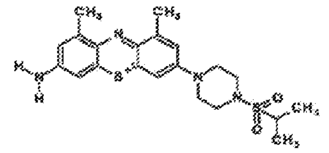
FIG. 1P is a table showing the anti-viral activities of some compounds of the invention as determined by the methods described herein.
Figure 1P:
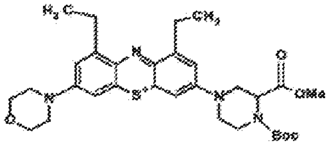
Figure 1P:
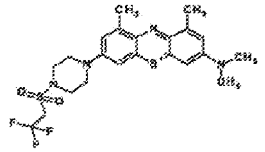
Figure 1P:
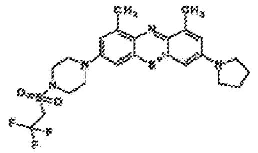
Figure 1P:
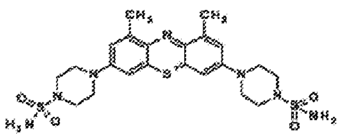
Figure 1P:
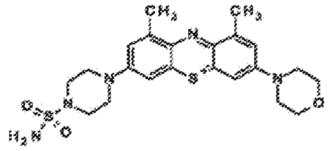
Figure 1Q:
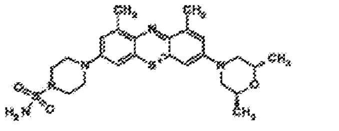
FIG. 1Q is a table showing the anti-viral activities of some compounds of the invention as determined by the methods described herein.
Figure 1Q:
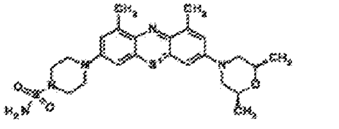
Figure 1Q:
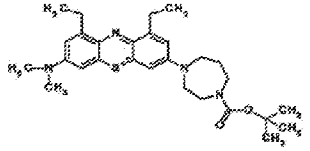
Figure 1Q:
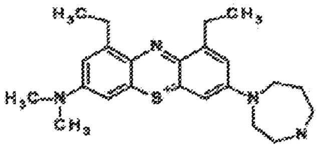
Figure 1Q:
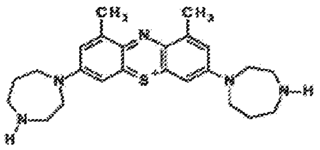
Figure 1Q:
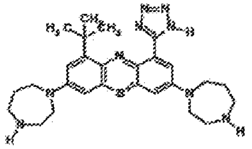
Figure 1R:
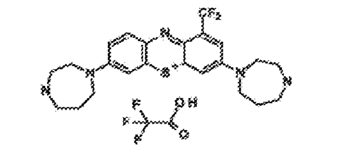
FIG. 1R is a table showing the anti-viral activities of some compounds of the invention as determined by the methods described herein.
Figure 1R:
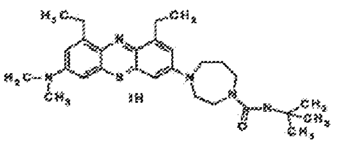
Figure 1R:
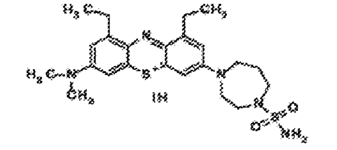
Figure 1R:
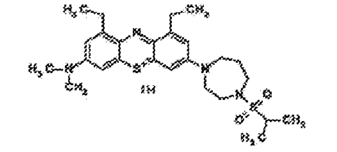
Figure 1R:
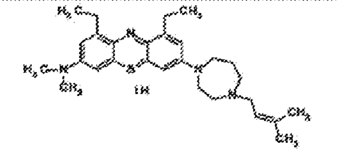
Figure 1R:
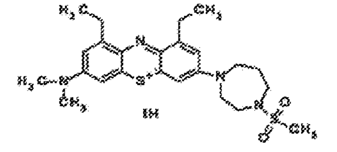
Figure 1S:
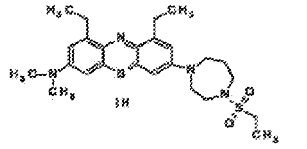
FIG. 1S is a table showing the anti-viral activities of some compounds of the invention as determined by the methods described herein.
Figure 1S:
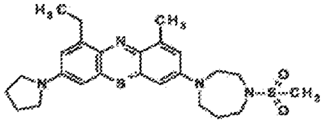
Figure 1S:
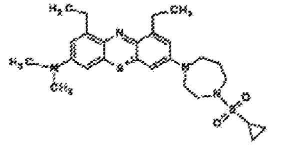
Figure 1S:
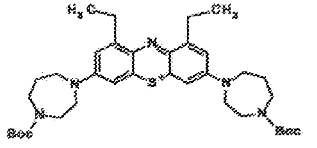
Figure 1S:
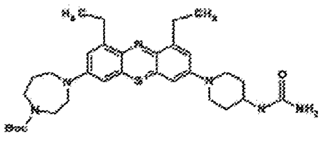
Figure 1S:
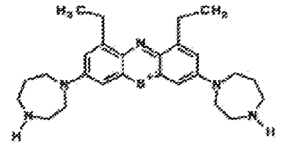
Figure 1T:
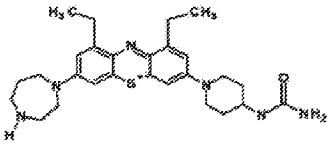
FIG. 1T is a table showing the anti-viral activities of some compounds of the invention as determined by the methods described herein.
Figure 1T:
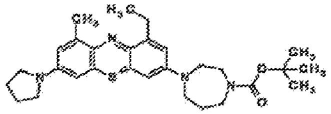
Figure 1T:
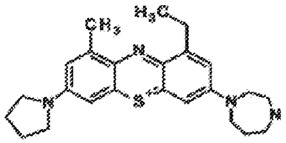
Figure 1T:
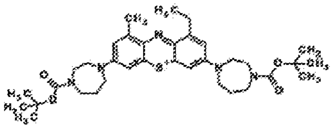
Figure 1T:
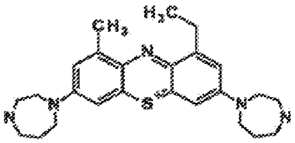
Figure 1T:
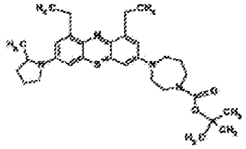
Figure 1U:
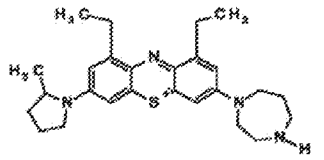
FIG. 1U is a table showing the anti-viral activities of some compounds of the invention as determined by the methods described herein.

Those having ordinary skill in the art will appreciate that compounds having the structure shown above (FIG. 1) can exist in a variety of formal hybridization structures that may or may not include a formal charge; thus, the structural formula for shown above (and all similar formulas herein) implicitly includes all equivalent resonance structures including any charges. Similarly, the illustration of any specific resonance structure herein is defined to include all equivalent resonance structures implicitly unless specifically noted otherwise. The identification of such resonance structures and their equivalents is well known to persons having ordinary skill in the art.

$R^1$-$R^{9b}$ are selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuonyl, cycloalkylsulfonyl, aralkycarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl) iminoalkyl, and (cycloheteroalkyl)iminoalkyl.

$R^{10}$ is hydrogen or optionally substituted alkyl, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsufonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl.

$X^1$ is $(CR^{11}R^{11'})_m$, wherein m is either 1 or 2 such that each of $R^{11}$ and $R^{11'}$, independently for each value of m, is selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl) alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuonyl, cycloalkylsulfonyl, aralkycarbonylthioooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

As used herein, the phrase "independently for each value of m, is selected independently" refers to the fact that each methylene unit can include two different substituents (when the carbon atom is fully saturated). In other words, each value of m can yield as many as 2×m different substituents, which will be denoted herein by the lower case letters a, b, c, . . . , etc. Thus, as used herein the group denoted $(CR^{11}R^{11'})_m$ will yield $(CR^{11a}R^{11b})$ for m=1, $(CR^{11a}R^{11b})(CR^{11c}R^{11d})$ for m=2, etc. In some cases, as will be obvious to those having ordinary skill in the art, the substitutent will define an unsaturated carbon, i.e., an sp or $sp^2$ carbon, such as in the case of nitriles or carbonyls, in which case the two substituents on a carbon atom are treated as a single unitary substituent.

Y is optionally present; and when Y is present, Y is $NR^{12}$, O, S, SO, or $SO_2$, or a single or double bond between $X^2$ and $X^3$; $R^{12}$ is hydrogen or optionally substituted alkyl, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl; and $X^2$ and $X^3$ are $(CR^{13}R^{13})_n$ and $(CR^{14}R^{14})_o$ respectively, wherein each of n and o is independently either 1, 2, or 3 such that the sum n+o is either 3, 4, or 5, and independently for each value of the n and o methylene units of $X^2$ and $X^3$, each of $R^{13}$, $R^{13'}$, $R^{14}$, $R^{14'}$ is selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthiooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl. When Y is not present $X^2$ is $R^{15}$ and $X^3$ is $R^{16}$, where $R^{15}$ and $R^{16}$ are selected independently from the group consisting of: hydrogen and optionally substituted alkyl, alkylcarbonyl, arylcarbonyl, heteroarylcarbonyl, cycloalkycarbonyl, cycloheteroalkylcarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl.

When Y is not present $X^2$ is $R^{15}$ and $X^3$ is $R^{16}$, where $R^{15}$ and $R^{16}$ are selected independently from the group consisting of: hydrogen and optionally substituted alkyl, alkylcarbonyl, arylcarbonyl, heteroarylcarbonyl, cycloalkycarbonyl, cycloheteroalkycarbonyl, aralkycarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsulfonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl.

In one embodiment, the present invention provide compounds defined above in which m is 1, such that $X^1$ is $(CR^{11}R^{11'})$; thereby defining $X^1$ as $(CR^{11a}R^{11b})$, said compounds having the structure:

wherein $R^{11a}$ and $R^{11b}$ are selected independently from the group consisting of: hydrogen,

Figure 2

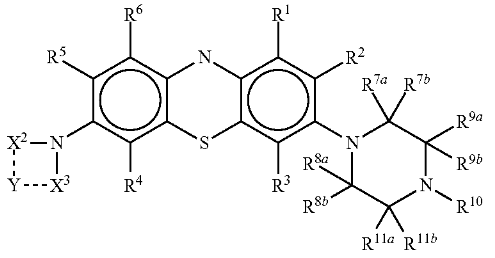

halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl) alkylcarbonyloxy, alkylcarbonyl, arylcarbonyl, heteroarylcarbonyl, cycloalkycarbonyl, cycloheteroalkycarbonyl, aralkylcarbonyl, heteroaralkylcarbonyl, (cycloalkyl) alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthioooxy, carbonylythio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

Among the compounds just described (FIG. 2) are embodiments in which Y is not present, such compound having the structure:

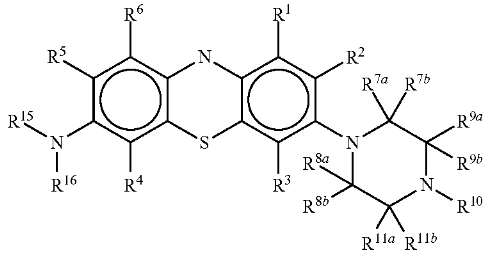

Particular embodiments of these compounds include those in which each of $R^{15}$ and $R^{16}$ is hydrogen. More particular embodiments are those in which each of $R^{15}$ and $R^{16}$ is hydrogen, and each of $R^2$-$R^5$, $R^{7a}$-$R^{9b}$, $R^{11a}$ and $R^{11b}$ is hydrogen, each of $R^1$ and $R^6$ independently is optionally substituted alkyl, and $R^{10}$ is optionally substituted alkyl or alkylsulfonyl. Still more specific embodiments have the substituents just described and further each of $R^{15}$ and $R^{16}$ independently is alkyl or alkyloxyalkyl. More specific among these embodiments are those wherein each of $R^{15}$ and $R^{16}$ independently is alkyl, still more specifically methyl or ethyl. Yet more specific embodiments include these substituents and further each of $R^2$-$R^5$, $R^{7a}$-$R^{9b}$, $R^{11a}$, and $R^{11b}$ is hydrogen, each of $R^1$ and $R^6$ is selected independently from the group consisting of hydrogen, halo, and optionally substituted alkyl, and $R^{10}$ is hydrogen, or optionally substituted alkyl, alkyloxycarbonyl, alkylsulfonyl, cycloalkylsulfonyl, and alkylaminosulfonyl.

In other embodiments of FIG. 2 Y is present, said compound having the structure:

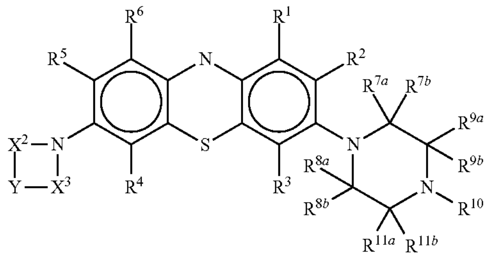

In some embodiments, each of n and o is 2 for these compounds, such that $X^2$ and $X^3$ have the form $(CR^{13}R^{13'})_2$ and $(CR^{14}R^{14'})_2$ respectively, defining thereby $X^2$ as $(CR^{13a}R^{13b}))(CR^{13c}R^{13d})$ and $X^3$ as $(CR^{14a}R^{14b})(CR^{14c}R^{14d})$, said compound having the structure:

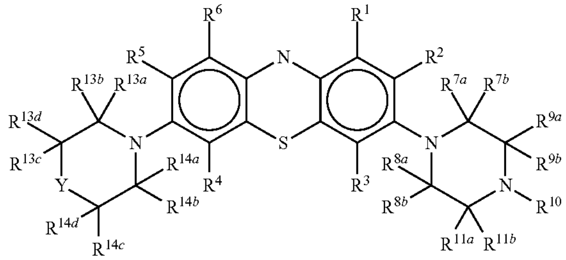

wherein $R^{13a}$-$R^{14d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

In more particular embodiments, when Y is present, in addition to the substituents described above each of $R^2$-$R^5$, $R^{7a}$-$R^{9b}$, $R^{11a}$, $R^{11b}$, and $R^{13a}$-$R^{14d}$ is hydrogen, each of $R^1$ and $R^6$ is selected independently from the group consisting of hydrogen, halo, and optionally substituted alkyl. Among these compounds are further embodiments defined by the additional specification that Y is $NR^{12}$ or O. In more specific embodiments, Y is $NR^{12}$, and $R^{10}$ and $R^{12}$ are selected independently from the group consisting of: hydrogen, or optionally substituted alkyl, alkyloxycarbonyl, alkylsulfonyl, cycloalkylsulfonyl, and alkylaminosulfonyl. In other more specific embodiments, Y is O.

Other embodiments are defined by the compound shown in FIG. 1, wherein m is 2, such that $X^1$ is $(CR^{11}R^{11'})_2$, thereby defining $X_1$ as $(CR^{11a}R^{11b})(CR^{11c}CR^{11d})$, said compound having the structure:

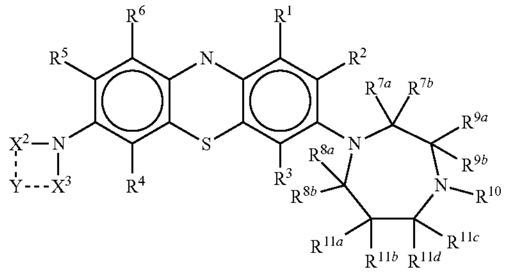

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

Some embodiments of the invention include those just described above (FIG. 3) and further wherein Y is not present, such compounds having the structure:

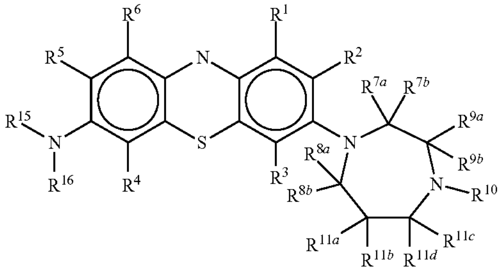

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkycarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkycarbonyl, cycloheteroalkycarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroar alkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulonyl, heteroarylsuony, cycloalkylsulfonyl, aralkycarbonylthioooxy, carbonylythio, heteroaralkylcarbonylthio, (cycloalkyloxy)carbonylthio, (cycloheteroalkyl) alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

In other embodiments, compounds of the invention have the description provided above (FIG. 3) but wherein Y is present, these compounds have the structure:

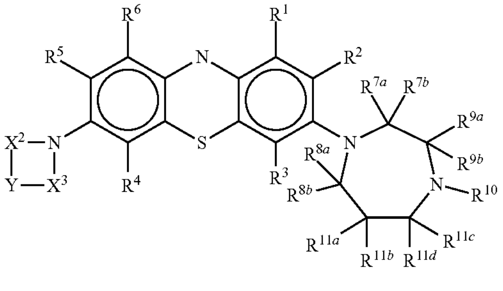

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl) alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

In another aspect, the present invention provide methods for treating a viral disease in a mammal afflicted with such disease, comprising administering to such mammal a therapeutically effective amount of a compound described herein, i.e., a compound encompassed with the compounds illustrated in FIG. 1 above. In more specific embodiments, the viral disease is an etiological component of a respiratory syndrome selected from the group consisting of: bronchiolitis, the common cold, croup, influenza, and pneumonia. For example and not limitation, Influenza is associated with the first three syndromes listed above; adenovirus with the first two and the third; and rhinovirus with the last syndrome.

In another aspect, the present invention provides methods and compositions for treating a viral disease in a mammal afflicted with such disease, comprising administering to such mammal a therapeutically effective amount of a compound described herein. In more particular embodiments the viral disease is Influenza (Flu), Adenovirus (ADV), Human Corona Virus (HCoV), Herpes Simplex Virus (HSV), Rhinovirus (RHNV), Respiratory Syntactical Virus (RSV), Hepatitis C Virus (HCV), Human Immunodeficiency Virus (HIV), Monkey Pox Virus (MPXV), Rabies Virus (RABV), Dengue Virus (DENV), Easter Equine Encephalitis Virus (EEEV), Venezuelan Equine Encephalitis Virus (VEEV), Wester Equine Encephalitis Virus (WEEV), West Nile Virus (WNV), Chikungunya Virus (CKGV), Ebola Virus (EBOV), Marburg Virus (MARV). Particular, non limiting, exemplary compounds and their activities against these viruses are provided in the Appendix.

5.3 Synthesis of the Compounds of the Invention

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N. H.), Aspin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance CH and $^{13}C$ NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

5.4 Compositions for, and Methods of, Treating Viral Infections

Compounds of the present invention can be administered in a variety of ways including enteral, parenteral and topical routes of administration. For example, suitable modes of administration include oral, subcutaneous, transdermal, transmucosal, iontophoretic, intravenous, intramuscular, intraperitoneal, intranasal, subdural, rectal, vaginal, and the like.

In accordance with other embodiments of the present invention, there is provided a composition comprising a compound described here, together with a pharmaceutically acceptable carrier or excipient. Suitable pharmaceutically acceptable excipients include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinylpyrrolidinone, low melting waxes, ion exchange resins, and the like, as well as combinations of any two or more thereof. Other suitable pharmaceutically acceptable excipients are described in Remington's Pharmaceutical Sciences, Mack Pub. Co., New Jersey (1991), which is incorporated herein by reference.

Pharmaceutical compositions of the present invention may be in any form suitable for the intended method of administration, including, for example, a solution, a suspension, or an emulsion. Liquid carriers are typically used in preparing solutions, suspensions, and emulsions. Liquid carriers contemplated for use in the practice of the present invention include, for example, water, saline, pharmaceutically acceptable organic solvent(s), pharmaceutically acceptable oils or fats, and the like, as well as mixtures of two or more thereof. The liquid carrier may contain other suitable pharmaceutically acceptable additives such as solubilizers, emulsifiers, nutrients, buffers, preservatives, suspending agents, thickening agents, viscosity regulators, stabilizers, and the like. Suitable organic solvents include, for example, monohydric alcohols, such as ethanol, and polyhydric alcohols, such as glycols. Suitable oils include, for example, soybean oil, coconut oil, olive oil, safflower oil, cottonseed oil, and the like. For parenteral administration, the carrier can also be an oily ester such as ethyl oleate, isopropyl myristate, and the like. Compositions of the present invention may also be in the form of microparticles, microcapsules, liposomal encapsulates, and the like, as well as combinations of any two or more thereof.

The compounds of the present invention may be administered orally, parenterally, sublingually, by inhalation spray, rectally, vaginally, or topically in dosage unit formulations containing conventional nontoxic pharmaceutically acceptable carriers, adjuvants, and vehicles as desired. Topical administration may also involve the use of transdermal administration such as transdermal patches or ionophoresis devices. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-propanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid can be useful in the preparation of injectables.

Suppositories for rectal or vaginal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting agents, emulsifying and suspending agents, cyclodextrins, and sweetening, flavoring, and perfuming agents.

The compounds of the present invention can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and phosphatidyl cholines (lecithins), both natural and synthetic. Methods to form liposomes are known in the art.

While the compounds of the invention can be administered as the sole active pharmaceutical agent, they can also be used in combination with one or more other compound as described herein, or in combination with other agents used in the treatment or prevention of AD and related diseases, or both.

In addition, the compounds of the present invention can be used, either singly or in combination as described above, in combination with other modalities for preventing or treating AD and related diseases or disorders. Such other treatment modalities include without limitation, surgery, radiation, hormone supplementation, and diet regulation. These can be performed sequentially (e.g., treatment with a compound of the invention following surgery or radiation) or in combination (e.g., in addition to a diet regimen).

The additional active agents may generally be employed in therapeutic amounts as indicated by sources well known to those having ordinary skill in the art, e.g., the PHYSICIAN'S DESKEFERENCE (PDR) $53^{rd}$ Edition (1999), which is incorporated herein by reference, or such therapeutically useful amounts as would be known to one of ordinary skill in the art. The compounds of the invention and the other therapeutically active agents can be administered at the recommended maximum clinical dosage or at lower doses. Dosage levels of the active compounds in the compositions of the invention may be varied to obtain a desired therapeutic response depending on the route of administration, severity of the disease and the response of the patient. The combination can be administered as separate compositions or as a single dosage form containing both agents. When administered as a combination, the therapeutic agents can be formulated as separate compositions that are given at the same time or different times, or the therapeutic agents can be given as a single composition.

In accordance with yet other embodiments, the present invention provides methods for treating or preventing AD or similar disorder in a human or animal subject in which an amount of a compound of the invention that is effective to at least ameliorate disease symptoms. Effective amounts of the compounds of the invention generally include any amount sufficient to detectably modulate AD using standard measures, by other methods known to those having ordinary skill in the art, or by detecting prevention or alleviation of symptoms in a subject afflicted with AD.

The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy. The prophylactically or therapeutically effective amount for a given situation can be readily determined by routine experimentation and is within the skill and judgment of the ordinary clinician.

For exemplary purposes of the present invention, a prophylactically or therapeutically effective dose will generally be from about 0.1 mg $kg^{-1}$ $d^{-1}$ to about 100 mg $kg^{-1}$ $d^{-1}$, preferably from about 1 mg $kg^{-1}$ d" to about 20 mg $kg^{-1}$ $d^{-1}$, and most preferably from about 10 mg $kg^{-1}$ $d^{-1}$ to about 10 mg $kg^{-1}$ $d^{-1}$ of a compound of the present invention, which may be administered in one or multiple doses.

6 EXAMPLES

The following Examples are provided to illustrate certain aspects of the present invention and to aid those of skill in the art in the art in practicing the invention. These Examples are in no way to be considered to limit the scope of the invention in any manner.

6.0.1 Synthesis of Compounds

The compounds of the present invention can be synthesized using techniques and materials known to those of skill in the art. Starting materials for the compounds of the invention may be obtained using standard techniques and commercially available precursor materials, such as those available from Aldrich Chemical Co. (Milwaukee, Wis.), Sigma Chemical Co. (St. Louis, Mo.), Lancaster Synthesis (Windham, N.H.), Aspin Chemicals, Ltd. (New Brunswick, N.J.), Ryan Scientific (Columbia, S.C.), Maybridge (Cornwall, England), Arcos (Pittsburgh, Pa.), and Trans World Chemicals (Rockville, Md.)

The procedures described herein for synthesizing the compounds of the invention may include one or more steps of protection and deprotection (e.g., the formation and removal of acetal groups). In addition, the synthetic procedures disclosed below can include various purifications, such as column chromatography, flash chromatography, thin-layer chromatography ("TLC"), recrystallization, distillation, high-pressure liquid chromatography ("HPLC") and the like. Also, various techniques well known in the chemical arts for the identification and quantification of chemical reaction products, such as proton and carbon-13 nuclear magnetic resonance ($^1H$ and $^{13}C$ NMR), infrared and ultraviolet spectroscopy ("IR" and "UV"), X-ray crystallography, elemental analysis ("EA"). HPLC and mass spectroscopy ("MS") can be used for identification, quantitation and purification as well.

Although the schemes below illustrate specific starting materials and products, those having ordinary skill in the art will understand that many substitution patterns can be made using known methods and materials in combination with the teachings herein.

Phenothiazine Core

6.0.1.1 Di-(2-tolylamine)

Heated glassware then allowed to cool to room temperature under argon. Added $Pd_2(dba)_3$ (1.39 g, 1.52 mmol, 1.0 mol %) or $Pd(dba)_2$ (1.38 g, 2.4 mmol, 1.4 mol %), 2-(di-tert-butylphosphino)biphenyl (1.09 g, 3.65 mmol, 2.4 mol %), 2-bromotoluene (40 mL, 332.1 mmol) or 2-chlorotoluene (39 mL, 332.1 mmol), lithiumamide (3.47 g, 151.1 mmol, 45 mol %), sodium t-butoxide 29.5 g, 297.7 mmol, 90 mol %), then toluene (150 mL). Heated at 80° C. under argon 4.5 h to overnight; let cool to room temperature. Diluted with diethyl ether, then filtered through a pad of celite. Concentrated the resulting filtrate in vacuo. Used in the next reaction without purification. Alternatively, purify the resulting residue by Isco column chromatography in hexane to give the product as white crystals with a yellow tint (23.4 g, 118.6 mmol, 72% yield). Alternatively, for purification, perform repeated crystallizations of the residue from hot isopropanol or acetone/isopropanol to obtain product. For another alternative purification, dissolve residue indichloromethane and put through silica plug with hexane rinses followed by hexane containing about 1% dichloromethane. Collected the filtrates and concentrated them to obtain yellow-white solids as product.

6.0.1.2 1,9-dimethyl-10H-phenothiazine

Put di(2-tolyl)amine (11.7 g, 59.3 mmol) in a 3-neck 100 mL round-bottom flask. Added elemental sulfur (3.9 g, 121.65 mmol, 2 eq.), crushed iodine (0.44 g, 1.73 mmol, 3 mol %), then o-dichlorobenzene (22 mL). Added an outlet to a dilute bleach solution (for hydrogen sulfide evolution) then put under argon. Refluxed at 180° C. for 4 h. Remove solvent under reduced pressure. Purified with Isco column chromatography using 2% ethyl acetate/98% hexane. Obtained product as white crystals (2 g, 8.8 mmol, 15% yield). Alternatively, put di(2-tolyl)amine (either purified or impure from the aforementioned reaction; 8.9525 g, 45.3 mmol) in a round bottom flask. Added elemental sulfur (2.98 g, 92.9 mmol, 2 eq.) then crushed iodine (3.28 g, 12.9 mmol, 28% mol). Added an outlet to a dilute bleach solution (for hydrogen sulfide) then put under argon. Stirred at 210° C. for 30 min or until no starting material was present by LC/MS. Allowed the reaction cool to about 60° C. then add hexane for extraction. Repeat hot hexane extractions (at least one overnight; minimum time of half an hour for each extraction) of reaction until product was no longer seen in residue (about 4 times). Combined hexane extractions and concentrate in vacuo. Purified resulting residue either through repeated repeated hot hexane/ethanol or isopropanal crystallizations, hot acetone/isopropanol crystallizations (or triturations) or Isco column chromatography using 2% ethyl acetate/98% hexane to obtain product as white crystals (2.92 g, 12.8 mmol, 28% yield).

6.0.1.3 1,9-Dimethoxy-10H-phenothiazine

Procedures the same as above, but used 2-chloroanisole instead of 2-bromotoluene or 2-chlorotoluene in the initial step.

6.0.1.4 1-Isopropyl-9-methyl-10H-phenothiazine

Procedures the same as Examples above, but used 2-bromocumene and 2-bromotoluene instead of just 2-bromotoluene or just 2-chlorotoluene in the initial step.

6.0.1.5 1-Cyano-10H-phenothiazine

Prepared 1-cyanophenothiazine as described in the literature starting from 2-aminobenzenethiol (2.1 mL, 2.46 g, 20 mmol), 2,3-difluorobenzonitrile (1.9 mL, 2.83 g, 20 mmol), and sodium hydride (1.09 g, 27.3 mmol) in 10 mL of DMF. After crystallizing from dichloromethane-ethanol, obtained 1-cyanophenothiazine as a dark yellow powder (1.342 g, 6 mmol, 30% yield).

6.0.1.6 1-(1H-Tetrazol-5-yl)-10H-phenothiazine

Prepared 1-(1H-tetrazol-5-yl)-phenothiazine as described in the literature starting from 1-cyanophenothiazine (200 mg, 0.891 mmol), sodium azide (308 mg, 4.74 mmol, 5.3 eqs.), then ammonium chloride (254 mg, 4.75 mmol, 5.3 eqs.) in DMF (10 mL) at 120° C. overnight. Added dilute aqueous phosphoric acid (pH 1) until fluffy white or yellow precipitate stopped appearing. Rinsed with deionized water until neutral then dried the resulting yellow precipitate overnight under vacuum to obtain product (162.8 mg, 0.609 mmol, 68% yield). Used in the next reactions without further purification.

6.0.1.7 4-Carboxy-1,9-dimethylphenothiazin-5-ium tetraiodide hydrate

Procedure the same as above, but used 1,9-dimethylphenothiazine-4-carboxylic acid, instead of 1,9-dimethylphenothiazine.

Activated Phenothiazines 6.0.1.8
3,7-Dibromo-1,9-dimethyl-10H-phenothiazine

Bromination performed as described in the literature starting from dimethylphenothiazine (instead of phenothiazine) (1.008 g, 4.4 mmol), acetic acid (36 mL), and bromine (0.57 mL, 1.77 g, 11.1 mmol, 2.5 eqs.) in acetic acid (4 mL). Performed workup as described in the literature using sodium sulfite (1.12 g, 8.9 mmol, 2 eqs.) then after 20 min, deionized water (1 mL). Dissolved potassium hydroxide (680 mg, 12.11 mmol, 2.75 eqs.) in 50 mL of deionized water and brought the volume up to 100 mL with ice. Added the above reaction mixture to get a gray precipitate and stirred for 2 h to overnight. Filtered off the gray precipitate, rinse with more deionized water, then dried overnight under vacuum to obtain product as a dark gray solid without further purification (1.6 g, 4.15 mmol, 94% yield).

6.0.1.9
3,7-Dibromo-1-(1H-tetrazol-5-yl)-10H-phenothiazine

Procedure the same as above, but used 1-(1H-tetrazol-5-yl)-10H-phenothiazine instead of 1,9-dimethylphenothiazine.

6.0.1.10 tert-Butyl 3,7-dibromo-1,9-dimethyl-10H-phenothiazine-10-carboxylate

Performed as described in the literature. Alternatively, added crushed DMAP (316 mg, 2.59 mmol) followed by acetonitrile (8 mL) to 3,7-dibromo-1,9-dimethyl-10H-phenothiazine (1.6 g, 4.15 mmol). The suspension was heated to 85° C. then crushed $Boc_2O$ was added (1.9 g, 8.5 mmol, 2 eqs.) dissolved in acetonitrile (2 mL). Refluxed overnight. Filtered off precipitate, dissolved in dichloromethane, extract with diluted 2 N phosphoric acid (pH=2) once, then with deionized water until neutral (4×). Simultaneously, added water to the remaining filtrate and repeated the same extraction sequence. Alternatively, removed solvents under vacuum from the filtrate and performed the above extraction sequence on the resulting residue. Dry organic layers over sodium sulfate then remove solvent under vacuum. Dissolved in acetone then add isopropanol until precipitate appeared. Alternatively, purified using flash silica gel chromatography. Obtained product as mauve or pale green precipitate (1.25 g, 2.58 mmol, 62% yield).

6.0.1.11 tert-Butyl 3,7-dibromo-1-(1H-tetrazol-5-yl)-10H-phenothiazine-10-carboxylate Procedure the same as above, but used 3,7-dibromo-1-(1H-tetrazol-5-yl)-10H-phenothiazine instead of 3,7-dibromo-1,9-dimethyl-10H-phenothiazine.

Sunfonylpiperazinyl Phenothiazines 6.0.1.12 HCl Salt of 1-(isopropylsulfonyl)piperazine At 0° C. to −10° C., mixed Boc-piperazine (7.3541 g, 38.695 mmol) with DIPEA (12.58 mL, 71.86 mmol) in dichloroethane (DCE) for deprotonation. Mixed propane-2-sulfonyl chloride (5 mL, 42.3 mmol) with DCE (40 mL) and added dropwise to the iced piperazine mixture. Once addition was complete, removed the ice bath and stirred at room temperature, checking reaction by TLC and LC/MS. Once the reaction was completed, added ethyl acetate and filtered off the resulting white crystals (the DIPEA-HCl salt). Took the remaining ethyl acetate solution and extract with 1M aqueous HCl (once), then saturated aqueous sodium bicarbonate (once), then brine until neutral (twice). Dried the resulting ethyl acetate layer over sodium sulfate then removed solvent. Dried under vacuum overnight to obtain the Boc-protected sulfonylpiperazine as an orange white solid (10.4 g, 35.57 mmol, 92% yield). Without further purification, added the above Boc-protected sulfonylpiperazine (10.4 g, 35.57 mmol) to DCE (40 mL) followed by an equal volume of 4 M in dioxane (40 mL). Stirred overnight. Once the reaction appeared complete by TLC and LC/MS, filtered off the resulting precipitate and rinse with cold dichloromethane until it was less acidic. Dried under vacuum overnight to obtain product as an offwhite precipitate (as the HCl salt, 7.85 g, 34.32 mmol, 96% yield). Used in subsequent reactions without further purification.

6.0.1.13 HCl Salt of 1-(2,2,2-trifluoroethylsulfonyl)piperazine

Procedure the same as above, but used 2,2,2-trifluoroethanesulfonyl chloride instead of propane-2-sulfonyl chloride.

Derivatives of Methylene Blue 6.0.1.14 1,9-Dimethoxy-3,7-bis(4-methylpiperazin-1-yl)phenothiazin-5-ium bromide Performed the reaction as described in the literature starting with 3,7-dibromo-1,9-dimethoxyphenothiazin-5-ium bromide (750 mg, 1.54 mmol), N-methylpiperazine (0.848 mL, 7.7 mmol) and chloroform (35 mL). Purified using flash silica gel chromatography to obtain product as a dark blue residue (35 mg, 0.65 mmol, 4% yield).

6.0.1.15 3-(4-(tert-Butoxycarbonyl)piperazin-1-yl)-7-(diethylamino)-2-methoxyphenothiazin-5-ium bromide and 3,7-bis(4-(tert-butoxycarbonyl)piperazin-1-yl)-2-methoxyphenothiazin-5-ium bromide Procedure the same as above, but used 3,7-dibromo-2-dimethoxyphenothiazin-5-ium bromide, instead of 3,7-dibromo-1,9-dimethoxyphenothiazin-5-ium bromide and diethylamine and N-Boc-piperazine simultaneously, instead of N-methylpiperazine.

6.0.1.16 3-(Dimethylamino)-1,9-dimethyl-7-(4-methylpiperazin-1-yl)phenothiazin-5-ium iodide and 1,9-dimethyl-3,7-bis(4-methylpiperazin-1-yl)-phenothiazin-5-ium iodide Performed the reaction as described in the literature starting with the dimethylphenothiazinium salt (3.18 g, 4.22 mmol) in chloroform (152 mL) and N-methylpiperazine (0.95 mL, 8.63 mmol). Reaction progress was monitored via LC/MS and TLC. Once newly formed precipitate was filtered off or the solvent removed under vacuum, the resulting iodide salt was stirred with ether or hexane overnight to remove excess amine then refiltered. After pumping down under vacuum, a dark precipitate was obtained as an intermediate. Without further purification, performed the 2' amine addition with dimethylamine (2 M in THF; 2.11 mL, 4.22 mmol) and methanol (115 mL), as described in the. Alternatively, acetonitrile was used as the solvent instead of methanol and the addition of the amine was alternated with the addition of the solvent. Progress was monitored via LC/MS and TLC. Used flash silica gel chromatography to obtain unsymmetrical product as a blue solid (1.04 g, 2.10 mmol, 50% yield) and the symmetrical dipiperazine as by-product.

6.0.1.17 3-(4-(tert-Butoxycarbonyl)piperazin-1-yl)-7-(dimethylamino)-1,9-dimethylphenothiazin-5-ium iodide, 3,7-bis(4-(tert-butoxycarbonyl)piperazin-1-yl)-1,9-dimethylphenothiazin-5-ium iodide, and 3-(dimethylamino)-1,9-dimethyl-7-(piperazin-1-yl) phenothiazin-5-ium 2,2,2-trifluoroacetate Performed the reaction as described above, but used tert-butyl piperazine-1-carboxylate (instead of N-methylpiperazine) in the $1^{st}$ step with chloroform and dimethylamine (2 M in THF) for the $2^{nd}$ step in the more polar solvent. Dissolved some of the asymmetrical adduct (37 mg, 0.063 mmol) in dichloromethane (1-1.5 mL). Added TFA (0.5-1 mL, up to 13.5 mmol). Stirred for 24 h to 72 h. Removed solvent under vacuum. Purified via flash silica gel chromatography. Obtained product as a dark blue-green residue (10 mg, 0.021 mmol; 34% yield).

6.0.1.18 3-(Butyl(methyl)amino)-7-(4-(2-methoxyethyl)piperazin-1-yl)-1,9-dimethylphenothiazin-5-ium iodide and 3,7-bis[4-(2-methoxyethyl)piperazin-1-yl]-1,9-dimethyl-phenothiazin-5-ium iodide Performed the reaction as described above, but used 1-(2-methoxyethyl)-piperazine (instead of N-methylpiperazine) in the $1^{st}$ step with chloroform and N-methylbutan-1-amine, (instead of dimethylamine), for the 2' step in the more polar solvent.

6.0.1.19 3-(4-(Cyclopropylsulfonyl)piperazin-1-yl)-7-(dimethylamino)-1,9-dimethylphenothiazin-5-ium iodide Performed the reaction as described above, but used 1-(cyclopropylsulfonyl)-piperazine hydrochloride salt and excess triethylamine (instead of N-methylpiperazine) in the $1^{st}$ step with chloroform.

6.0.1.20 3-(Dimethylamino)-7-(4-(isopropylsulfonyl) piperazin-1-yl)-1,9-dimethylphenothiazin-5-ium iodide Performed the reaction as described above, but used 1-(isopropylsulfonyl)piperazine hydrochloride salt and excess triethylamine (instead of N-methylpiperazine) in the $1^{st}$ step with chloroform. Product precipitates out of the reaction.

6.0.1.21 3-(Azetidin-1-yl)-7-(4-(isopropylsulfonyl) piperazin-1-yl)-1,9-dimethylphenothiazin-5-ium iodide Performed the reaction as described above, but used 1-(isopropylsulfonyl)piperazine hydrochloride salt and excess triethylamine (instead of N-methylpiperazine) in the $1^{st}$ step with chloroform and azetidine hydrochloride salt with excess triethylamine (instead of dimethylamine) for the 2' step in the more polar solvent.

6.0.1.22 3-(Dimethylamino)-1,9-dimethyl-7-(4-(2,2,2-trifluoroethylsulfonyl)piperazin-1-yl)phenothiazin-5-ium iodide Performed the reaction as described above, but used 1-(2,2,2-trifluoroethylsulfonyl)piperazine hydrochloride salt and excess triethylamine (instead of N-methylpiperazine) in the $1^{st}$ step with chloroform.

6.0.1.23 1,9-Dimethyl-3-(pyrrolidin-1-yl)-7-(4-(2,2,2-trifluoroethylsulfonyl)piperazin-1-yl)phenothiazin-5-ium iodide Performed the reaction as described above, but used 1-(2,2,2-trifluoroethylsulfonyl)piperazine hydrochloride salt and excess triethylamine (instead of N-methylpiperazine) in the $1^{st}$ step with chloroform and pyrrolidine (instead of dimethylamine) for the $2^{nd}$ step in the more polar solvent.

6.0.1.24 1,9-Dimethyl-3-morpholino-7-(4-sulfamoylpiperazin-1-yl)phenothiazin-5-ium iodide Performed the reaction as described above, but used piperazine-1-sulfonamide hydrochloride salt and excess triethylamine (instead of N-methylpiperazine) in the $1^{st}$ step with chloroform and morpholine (instead of dimethylamine) for the $2^{nd}$ step in the more polar solvent (50:50 methanol:acetonitrile).

6.0.1.25 1,9-Dimethyl-3,7-bis(4-sulfamoylpiperazin-1-yl)phenothiazin-5-ium ioide, 3-((2R,6S)-2,6-dimethylmorpholino)-1,9-dimethyl-7-(4-sulfamoylpiperazin-1-yl)phenothiazin-5-ium iodide, and 3-((2R,6R)-2,6-dimethylmorpholino)-1,9-dimethyl-7-(4-sulfamoylpiperazin-1-yl)phenothiazin-5-ium iodide Performed the reaction as described above, but used piperazine-1-sulfonamide hydrochloride salt and excess triethylamine (instead of N-methylpiperazine) in the $1^{st}$ step with chloroform and 2,6-dimethylmorpholine (cis and trans isomers), instead of dimethylamine, for the $2^{nd}$ step in the more polar solvent (50:50 methanol:acetonitrile). The symmetrical dipiperazine adduct precipitated out. The asymmetrical adducts were isolated via preparatory TLC plates.

6.0.1.26 3,7-Di(1,4-diazepan-1-yl)-1,9-dimethylphenothiazin-5-ium iodide

Performed the reaction as described above, but used tert-butyl 1,4-diazepane-1-carboxylate (instead of N-methylpiperazine) in the $1^{st}$ step with chloroform and more tert-butyl 1,4-diazepane-1-carboxylate (instead of dimethylamine) for the $2^{nd}$ step in the more polar solvent. Dissolved the isolated Boc protected adduct in dichloromethane. Added 2% hydroiodic acid. Stirred until complete by TLC and LC/MS. Removed solvent under vacuum. Obtained product as a dark blue residue.

6.0.1.27 4-Carboxy-3-(dimethylamino)-1,9-dimethyl-7-(4-methylpiperazin-1-yl)phenothiazin-5-ium iodide Performed the reaction as described above, but used the 4-carboxy-1,9-dimethylphenothiazin-5-ium salt instead of the dimethylphenothiazinium salt.

6.0.1.28 4-Carboxy-7-(dimethylamino)-1,9-dimethyl-3-(4-methylpiperazin-1-yl)phenothiazin-5-ium iodide Performed the reaction as described above, but added dimethylamine (2 M in THF) in the $1^{st}$ step with chloroform (instead of N-methylpiperazine) and added N-methylpiperazine (instead of dimethylamine) for the 2' step in the more polar solvent.

6.0.1.29 3-(4-(Cyclopropylsulfonyl)piperazin-1-yl)-7-(dimethylamino)-1-isopropyl-9-methylphenothiazin-5-ium iodide Performed the reaction as described above, but used the 1-isopropyl-9-methylphenothiazin-5-ium salt instead of the dimethylphenothiazinium salt.

6.0.1.30 3-Amino-7-(4-isopropylpiperazin-1-yl)-1,9-dimethylphenothiazin-5-ium iodide Performed the reaction as described in the literature starting with the dimethylphenothiazinium salt (0.1017 g, 0.135 mmol) in chloroform (5 mL) and N-isopropylpiperazine (0.039 mL, 0.267 mmol). Reaction progress was monitored via LC/MS and TLC. Once newly formed precipitate was filtered off or the solvent removed under vacuum, the resulting iodide salt was stirred with ether or hexane overnight to remove excess amine then refiltered. Without further purification, added dioxane to the intermediate (2 mL) followed by an equal volume of 8 N KOH then a few more drop of deionized water. Heated reaction to 70° C. and stirred for 1.5 h, until the intermediate was consumed as monitored by TLC. Removed the bottom aqueous layer, then removed the remaining organic solvent under vacuum. Dissolved in dichloromethane and extracted with deionized water until neutral. If there was only one layer, removed the solvent under vacuum. Purified using flash silica gel chromatography and isolated this by-product as a dark blue-purple solid (4 mg, 0.008 mmol, 3% yield).

6.0.1.31 3-Amino-1,9-dimethyl-7-(4-(methylsulfonyl)piperazin-1-yl)phenothiazin-5-ium iodide Performed the reaction as described above, but used 1-(methylsulfonyl)piperazine (instead of N-isopropylpiperazine).

6.0.1.32 3-Amino-1,9-dimethyl-7-(4-(triylfluoroylmethylsulfonyl)piperazin-1-yl)phenothiazin-5-ium iodide Performed the reaction as described above, but used 1-(2,2,2-trifluoroethylsulfonyl)piperazine hydrochloride salt and excess triethylamine N-isopropylpiperazine).

6.0.1.33 3-Amino-7-(4-(isopropylsulfonyl)piperazin-1-yl)-1,9-dimethylphenothiazin-5-ium iodide Performed the reaction as described above, but used 1-(isopropylsulfonyl)piperazine hydrochloride salt and excess triethylamine N-isopropylpiperazine).

6.0.1.34 tert-Butyl 3-(bis(2-methoxyethyl)amino)-1,9-dimethyl-7-(4-(methylsulfonyl)piperazin-1-yl)-10H-phenothiazine-10-carboxylate and tert-butyl-1,9-dimethyl-3,7-bis(4-(methylsulfonyl)piperazin-1-yl)-10H-phenothiazine-10-carboxylate Performed the reaction as described in the literature except used tert-butyl 3,7-dibromo-1,9-dimethyl-10H-phenothiazine-10-carboxylate (instead of the phenothiazine derivative; 350 mg, 0.722 mmol), 1-(methylsulfonyl)piperazine (instead of phenothiazine; 118.6 mg, 0.722 mmol) for the $1^{st}$ amination, bis(2-methoxyethyl)amine (instead of phenothiazine; 0.106 mL, 0.724 mmol) for the $2^{nd}$ amination, cesium carbonate (instead of sodium t-butoxide; 823 mg, 2.5 mmol), BINAP as the ligand (instead of tri-t-butylphosphine; 19 mg, 0.0305 mmol), either toluene or m-xylene (instead of o-xylene; 5 mL) at 90° C. to −100° C. for 2 h during the $1^{st}$ amination, and m-xylene (instead of o-xylene; 5 mL) for the $2^{nd}$ amination. The 2' amination was performed with or without purification and isolation after the first amination. Progress of the reaction is monitored by TLC and LC/MS. The final product(s) were purified using flash silica gel chromatography. The asymmetrical adduct was obtained as the main product (139 mg, 0.224 mmol, 31% yield) and the symmetrical dipiperazine adduct (83 mg, 0.127 mmol, 18% yield) was obtained as a minor by-product.

6.0.1.35 tert-Butyl 3-(bis(2-methoxyethyl)amino)-7-(4-isopropylpiperazin-1-yl)-1,9-dimethyl-10H-phenothiazine-10-carboxylate and tert-butyl 3,7-bis(4-isopropylpiperazin-1-yl)-1,9-dimethyl-10H-phenothiazine-10-carboxylate Performed the reaction as described above, but used N-isopropylpiperazine (instead of 1-(methylsulfonyl)piperazine) for the first amination.

6.0.1.36 3-(Diethylamino)-1,9-dimethyl-7-(4-(methylsulfonyl)piperazin-1-yl)phenothiazin-5-ium bromide and 3-(diethylamino)-1,9-dimethyl-7-(piperazin-1-yl)phenothiazin-5-ium bromide Performed the amination reactions as described above, but used diethylamine (instead of bis(2-methoxyethyl)amine) for the $2^{nd}$ amination. To remove the Boc protecting group, put the resulting asymmetrical adduct (105.3 mg, 0.225 mmol) in dichloromethane (1.5 mL), followed by an equal volume of 48% aqueous HBr (1.5 mL). Monitored by TLC and LC/MS. Removed solvent under vacuum. Dissolved in chloroform: methanol (3:1) or dichloromethane then extracted with deionized water until neutral. Extracted the first aqueous layer with chloroform:methanol (3:1). Combined the resulting organic layers, extract with deionized water until neutral, then removed the resulting organic solvents under vacuum again. Purified using flash silica gel chromatography. Obtained product as a blue solid (26.4 mg, 0.048 mmol, 22% yield) and an adduct without the sulfonyl group on the piperazine (3.0 mg, 0.006 mmol, 3% yield) as a blue solid by-product.

6.0.1.37 3-(Diethylamino)-7-(4-isopropylpiperazin-1-yl)-1,9-dimethylphenothiazin-5-ium bromide and 3,7-bis(4-isopropylpiperazin-1-yl)-1,9-dimethylphenothiazin-5-ium bromide Performed the reactions as described above, but used N-isopropylpiperazine (instead of 1-(methylsulfonyl)piperazine) for the first amination. Obtained both the expected asymmetrical adduct and the symmetrical dipiperazine by-product in near equal proportions. Boc removal was performed on both adducts.

6.0.1.38 3-(Diethylamino)-7-(4-isopropylpiperazin-1-yl)-1,9-dimethylphenothiazin-5-ium 2,2,2-trifluoroacetate and 3,7-bis(4-isopropylpiperazin-1-yl)-1,9-dimethylphenothiazin-5-ium 2,2,2-trifluoroacetate Performed the reactions as described above, but used trifluoroacetic acid (TFA) (instead of 48% aqueous HBr). Obtained both the expected asymmetrical adduct and the symmetrical dipiperazine by-product in near equal proportions.

6.0.1.39 1-tert-butyl-3,7-di(1,4-diazepan-1-yl)-9-(1H-tetrazol-5-yl)phenothiazin-5-ium 2,2,2-trifluoroacetate Performed the reactions as described above, but used tert-butyl-3,7-dibromo-1-(1H-tetrazol-5-yl)-10H-phenothiazine-10-carboxylate (instead of tert-butyl 3,7-dibromo-1,9-dimethyl-10H-phenothiazine-10-carboxylate), tert-butyl-1,4-diazepane-1-carboxylate for both amination steps, TFA (instead of 48% aqueous HBr) for the removal of the Boc protecting groups. The expected product was not obtained but thet-butylated adduct was isolated.

6.0.1.40 Phenothiazin-5-ium iodide

This compound was prepared according the procedure by B. Wilson et. al, *Tetrahedron* 64 (2008), 3429-3436. To the solution of 10H-phenothiazine in anhydrous chloroform (22 mL), at 5° C., surmounted with an addition funnel was added the solution of iodine (2.4 g, 9.40 mmol) in $CHCl_3$ (55 mL) over a 1 h period. The resulting dark solution was stirred for an additional 1 h at 5° C. monitored by TLC. After the disappearance of the starting material, the cooling bath was removed, solid precipitate was filtered, washed several times with chloroform, dried, to afford a very dark solid.

6.0.1.41 3,7-Dibromophenothiazin-5-ium bromide

Commercially available phenothiazine (2.00 g, 10.00 mmol) was dissolved in AcOH (120 mL) and a solution of $Br_2$ (10.0 mL) in AcOH (100 mL, 10% v/v, 195 mmol) was added all at once with vigorous stirring for 1.0 min. To this solution was added 400 mL of $H_2O$ and the red precipitate was filtered, washed with $Et_2O$, and dried under vacuum to give 4.09 g of a dark solid for a 94% yield.

6.0.1.42 1-Chlorophenothiazine

This compound was prepared according to a procedure by A. R. Katritzky et al., *Synthesis,* 1988, 215-217. To a solution of phenothiazine (10.0 g, 50.18 mmol) in anhydrous THF (200 mL) and cooled to −78° C. was added a solution of n-BuLi (24.1 mL, 60.2 mmol, 2.5 M in hexanes) dropwise. The mixture was stirred until a yellow precipitate formed, and then allowed to warm to room temperature, until a clear yellow solution resulted. The solution was again cooled to −78° C. and $CO_2$ gas was bubbled through the mixture for 5 min. The resulting solution was allowed to warm to RT and the solvent was evaporated to give a residue. The residue was again dissolved in anhydrous THF (200 mL) and cooled to −78° C., before t-BuLi (50 mL, 85 mmol, 1.7 M in pentane) was added dropwise. The resulting mixture was allowed to warm to −20° C. and was stirred at this temperature for 2 h. The reaction mixture was again cooled to −78° C. and a solution of hexachloroethane (100 mmol) in THF (50 mL) was added dropwise. The mixture was stirred at this temperature for 1 hour then allowed to warm to −20° C. and stirred for 2 h. The reaction mixture was quenched with ice cold 1 N HCL and extracted with EtOAC. The combined organic layers were washed with brine, dried over $MgSO_4$, filtered and evaporated to give a residue. The residue was purified by flash silica gel chromatography to give of an beige solid.

6.0.1.43 1-Chlorophenothiazin-5-ium Iodide

1-Chlorophenothiazine (664 mg, 2.84 mmol) was dissolved in $CHCl_3$ (50 mL) and cooled to 5° C. The solution was stirred as a solution of $I_2$ (2.16 g, 8.51 mmol) dissolved in $CHCl_3$ (10 mL) was added dropwise. The mixture was stirred at 5° C. overnight and allowed to warm to RT. The solvent was evaporated to dryness. The residue was stirred in $Et_2O$ and was filtered off and washed with $Et_2O$ until the filtrate was colorless. The dark solid was dried under vacuum and used without purification.

6.0.1.44 1-Ethylphenothiazine

This compound was prepared according to a procedure by A. R. Katritzky et al., *Synthesis,* 1988, 215-217. To a solution of phenothiazine (10.0 g, 50.18 mmol) in anhydrous THF (200 mL) and cooled to −78° C. was added a solution of n-BuLi (24.1 mL, 60.2 mmol, 2.5 M in hexanes) dropwise. The mixture is stirred until a yellow precipitate forms and then allowed to warm to room temperature, until a clear yellow solution results. the solution is again cooled to −78° C. and $CO_2$ gas is bubbled through the mixture for 5 min. The resulting solution is allowed to warm to RT and the solvent was evaporated to give a residue. The residue was again dissolved in anhydrous THF (200 mL) and cooled to −78° C., before t-BuLi (50 mL, 85 mmol, 1.7 M in pentane) was added dropwise. The resulting mixture was allowed to warm to −20° C. and was stirred at this temperature for 2 h. The reaction mixture was again cooled to −78° C. and a solution of ethyl iodide (100.0 mmol) in THF (50 mL) was added dropwise. The mixture was stirred at this temperature for 1 hour then allowed to warm to −20° C. and stirred for 2 h. The reaction mixture was quenched with ice cold 1N HCl and extracted with EtOAc. The combined organic layers were washed with brine, dried over $MgSO_4$, filtered and evaporated to give a residue. The residue was purified by flash silica gel chromatography to give the desired product.

6.0.1.45 1-Ethylphenothiazin-5-ium Iodide

1-Ethylphenothiazine (664 mg, 2.84 mmol) was dissolved in $CHCl_3$ (50 mL) and cooled to 5° C. The solution was stirred as a solution of $I_2$ (2.16 g, 8.51 mmol) dissolved in $CHCl_3$ (10 mL) was added dropwise. The mixture was stirred at 5° C. overnight and allowed to warm to RT. The solvent was evaporated to dryness. The residue was stirred in $Et_2O$ and was filtered off and washed with $Et_2O$ until the filtrate was colorless. The dark solid was dried under vacuum and used without purification.

6.0.1.46 2-(Trifluoromethyl)phenothiazin-5-ium iodide

Commercially available 2-Trifluoromethylphenothiazine (1.14 g, 4.28 mmol) was dissolved in $CHCl_3$ (20 mL) and a solution of $I_2$ (3.25 g, 12.84 mmol) in $CHCl_3$ (120 mL) was added. The mixture was warmed at 55° C. to 60° C. until the SM was consumed (by TLC). The reaction mixture was allowed to cool to RT and the solvent was evaporated. The residue was stirred in $Et_2O$, filtered off and washed with $Et_2O$ until the filtrate was colorless. The intermediate was used without further purification.

6.0.1.47 3,7-Dibromo-10H-phenothiazine

Phenothiazine (5.0 g, 25 mmol) was suspended in 200 mL of glacial AcOH Then, 3.3 mL $Br_2$ (0.63 mol) in 200 mL of glacial was slowly added to the reaction mixture and stirred for 6 h at room temperature. The reaction was cooled with an ice bath and 6.30 grams (50 mmol) of $Na_2SO_3$ was added to the reaction mixture. By adding a little water (3.0 mL), a deep-violet color formed within three hours. After the addition of a solution of 4.10 g (62 mmol) of KOH dissolved in water (1.0 L) a greenish solid formed, which was washed with a little cold 2-propanol. The solid was recrystallized with 2-propanol to give 7.90 g (88%) as a green powder.

6.0.1.48 3,7-dibromo-1,9-dichloro-10H-phenothiazine

The 3,7-dibromophenothiazine (6.25 g, 17.5 mmol) was dissolved in $CHCl_3$ (200 mL) and $SO_2Cl_2$ (3.13 mL, 38.5 mmol) was added dropwise over 15 min. The dark mixture was stirred at RT for 26 h. The mixture was then filtered and the solid washed with $CHCl_3$. The solid was collected and stirred in $Et_2O$ and the resulting green solid was filtered off and dried under vacuum to give a quantitative yield of the desired product.

6.0.1.49 tert-Butyl-3,7-dibromo-1,9-dichloro-10H-phenothiazine-10-carboxylate The 3,7-dibromo-1,9-dichloro-10H-phenothiazine (10.00 g, 23.47 mmol) was suspended in $CH_3CN$ (200 mL) and DMAP (2.87 g, 23.47 mmol) was added. The mixture was heated at reflux (near 85° C.) and $Boc_2O$ (15.16 g, 70.41 mmol) dissolved in $CH_3CN$ (50 mL) was added dropwise over 1 h. The reaction mixture became homogeneous and turned brown. The reaction was allowed to cool to RT and the solvent was evaporated. The residue was purified by flash silica gel chromatography to give a 95% yield.

6.0.1.50 Di-ortho-tolylamine

The round bottom flask was heated then allow to cool to room temperature under argon. Add $Pd_2(dba)_3$ (1.39 g, 1.52 mmoles, 1.0 mol %) or $Pd(dba)_2$ (1.38 g, 2.4 mmol, 1.4 mol %), 2-(di-tert-butylphosphino)biphenyl (1.09 g, 3.65 mmol, 2.4 mol %), 2-bromotoluene (40 mL, 332.1 mmoles) or 2-chlorotoluene (39 mL, 332.1 mmoles), lithium amide (3.47 g, 151.1 mmol, 45 mol %), sodium t-butoxide 29.5 g, 297.7 mmoles, 90 mol %), then toluene (150 mL). Heat at 80° C. under argon overnight. Let cool to room temperature. Diluted with diethyl ether then filtered through a pad of celite. Concentrated the resulting filtrate in vacuo. Used in the next reaction without purification. Purified the resulting residue by column chromatography with hexane to give the product as white crystals with a yellow tint (23.4 g, 118.6 mmol, 72% yield).

6.0.1.51 1,9-dimethyl-10H-phenothiazine

Put di(2-tolyl)amine (11.7 g, 59.3 mmol) in a 3-neck 100 mL round-bottom flask and added elemental sulfur (3.9 g, 121.65 mmoles, 2 eq.), crushed iodine (0.44 g, 1.73 mmoles, 3 mole %), then o-dichlorobenzene (22 mL). Added an outlet to a dilute bleach solution (for hydrogen sulfide evolution) then put under argon. Refluxed at 180° C. for 4 h. Removed solvent under reduced pressure. Purified with column chromatography using 2% ethyl acetate/98% hexane to obtain product as white crystals (2 g, 8.8 mmoles, 15% yield). (Alternatively, put di(2-tolyl)amine (either purified or impure from the aforementioned reaction; 8.9525 g, 45.3 mmoles) in a round bottom flask. Added elemental sulfur (2.98 g, 92.9 mmoles, 2 eq.) then crushed iodine (3.28 g, 12.9 mmoles, 28% mole). Added an outlet to a dilute bleach solution (for hydrogen sulfide) then put under argon. Stirred at 210° C. for 30 min or until no starting material was present by LC/MS. Let the reaction cool to about 60° C. then added hexane for extraction. Repeated hot hexane extractions (at least one overnight; minimum time of half an hour for each extraction) of reaction until product was no longer seen in residue (about 4 times). Combined hexane extractions and concentrate in vacuo. Purified resulting residue either through repeated hot acetone/isopropanol crystallizations (or triturations) or Isco column chromatography using 2% ethyl acetate/98% hexane to obtain product as white crystals (2.92 g, 12.8 mmoles, 28% yield).)

6.0.1.52 1,9-dimethylphenothiazin-5-ium 1,9-Dimethylphenothiazine (4.203 g, 18.49 mmol) was dissolved in 130 mL of chloroform and crushed iodine (14.1 g, 55.55 mmol, 3 eqs.) in 520 mL of chloroform was added over a period of 1.5 h to 2 h. Stirred for 1 h to 4 h. Once newly formed precipitate was filtered off or the solvent removed under vacuum, the resulting iodide salt was stirred with ether or hexane (sometimes overnight) to remove excess iodine then refiltered. After pumping down under vacuum, a brown precipitate was obtained as product (12.6 g)

6.0.1.53 N-(2-ethylphenyl)acetamide

To the stirred solution of commercially available ethyl aniline (20.3 g, 167.5 mmol, 1 eq.) in anhydrous pyridine (90 mL), 0° C., under argon was added acetic anhydride (32 mL, 335.04 mmol, 2 eq). After the addition, the resulting solution was stirred with warming to room temperature overnight. The reaction solution was cooled (zero degree), pH adjusted between 4 to 5 with 10% HCl, and extracted with ethyl acetate (2×500 mL). The combined organics were washed with brine, dried ($Na_2SO_4$), filtered and concentrated to provide the title compound as a white solid.

6.0.1.54 N,N-bis(2-ethylphenyl)acetamide

The mixture of the N-(2-ethylphenyl)acetamide (7.35 g, 45.03 mmol), anhydrous $K_2CO_3$ (6.22 g, 45.03 mmol), copper(I)bromide (452.2 mg, 3.15 mmol) in 1-bromo-2-ethylbenzene was stirred and heated to 200° C. under argon for 48 h. After cooling the reaction mixture was poured into ice-$H_2O$ and extracted with ethyl acetate (2×500 mL), the combined organics were washed with brine, dried over anhydrous $K_2CO_3$), filtered and concentrated to dryness. The crude obtained was purified on the ISCO machine using the ethyl acetate-hexane gradient to afford the N,N-bis(2-ethylphenyl) acetamide (8.1 g, 67%).

6.0.1.55 Bis(2-ethylphenyl)amine

The N,N-bis(2-ethylphenyl)acetamide (8.1 g, 30.30 mmol) and KOH (5 g), in EtOH (50 mL), was stirred and heated to reflux overnight. After 20 h additional KOH (10 g) was added, with stirring to reflux continued for an additional 6 h. It was cooled, poured into $H_2O$ (125 mL) and extracted with ethyl acetate (2×350 mL). The combined organics were washed with brine, dried ($MgSO_4$), filtered and concentrated to dryness, affording a dark red oil (5.8 g, 85%).

6.0.1.56 1,9-diethyl-10H-phenothiazine

The bis(2-ethylphenyl)amine, sulfur and iodine in vial (containing an outlet for gaseous expulsion) were combined and stirred in a preheated (150° C.) heating block for 15 min. The temperature was increased to 210° C., stirred and heated for an additional 45 min, and cooled. The dark mixture obtained was dissolved with 10% MeOH/$CH_2Cl_2$, silica gel added, concentrated and purified by flash silica gel chromatography using ethyl acetate-hexane gradient to afford the desired product (40%).

6.0.1.57 1,9-diethylphenothiazin-5-ium

This compound was prepared according the procedure by B. Wilson et. al., *Tetrahedron* 64 (2008), 3429-3436. To the solution of 1,9-diethyl-10H-phenothiazine (0.8 g, 3.13 mmol) in anhydrous chloroform (22 mL), at 5° C. surmounted with an addition funnel was added the solution of iodine (2.4 g, 9.40 mmol) in $CHCl_3$ (55 mL) over a 1 h period. The resulting dark solution was stirred for an additional 1 h at 5° C. as monitored by TLC. After the disappearance of the starting material, the cooling bath was removed, solid precipitate was filtered, washed several times with chloroform, dried, to afford a very dark solid (1.02 g, 50%).

6.0.1.58 N-acetyl-o-trifluoromethylaniline

Commercial o-trifluoromethylaniline (13.5 g, 83.9 mmol) was dissolved in acetic anhydride (55 mL, 580.0 mmol) and stirred at room temperature for 1 h. Then the reaction mixture was poured into $H_2O$, the whole was extracted with ethyl acetate (2×300 mL). The combined organic extracts were washed with 5% aqueous $NaHCO_3$, brine, dried ($K_2CO_3$), filtered and concentrated to provide the title compound as a white solid (15.7 g, 92%).

6.0.1.59 N-Acetyl-2-trifluoromethyldiphenylamine (4)

A mixture of the N-acetyl-O-trifluoromethyl-aniline (6.1 g, 30.0 mmol), anhydrous $K_2CO_3$ (4.1 g, 30.0 mmol), CuI (210 mg, 1.1 mmol) and bromobenzene (3) (16 mL, 160 mmol) was stirred and heated at 175° C. to 180° C. under an Ar atmosphere for 48 h. After cooling the reaction mixture was poured into ice-$H_2O$ and extracted with ethyl acetate (2×200 mL), the combined organic extracts were washed with brine, dried over anhydrous $K_2CO_3$, filtered and concentrated to dryness. The obtained crude material was purified by flash chromatography (using ethyl acetatehexane as an eluent) to afford the N-acetyl-2-trifluoromethyldiphenylamine (5.4 g, 64%).

6.0.1.60 2-Trifluoromethyldiphenylamine

A solution of the N-acetyl-2-trifluoromethyldiphenylamine (3.5 g, 12.5 mmol) in 10% KOH (2 g, 36 mmol)/EtOH (20 mL) was stirred and reflux for 6 h, then poured into $H_2O$. The mixture was extracted with ethyl acetate (2×100 mL). The combined organic layers were washed with brine, dried ($Na_2SO_4$), filtered and concentrated to dryness, gave dark red oil (2.5 g, 85%).

6.0.1.61 1-Trifluoromethyl-10H-phenothiazine

2-Trifluoromethyldiphenylamine (1.1 g, 4.6 mmol), sulfur (295 mg, 9.2 mmol) and iodine (328 mg, 1.29 mmol) were added in a vial, which was fitted with a balloon for discharge. A hot block was preheated (150° C.), the vial was heated on the hot block, and after 15 min the temperature was increased to 210° C.; the reaction mixture was stirred and heated for an additional 45 min and cooled. The dark solid material was dissolved in mixture methanol/chloroform and purified by flash chromatography (ethyl acetate-hexane as an eluent) to afford the desired product (450 mg, 36%).

6.0.1.62
3,7-Dibromo-1-trifluoromethyl-10H-phenothiazine

1-Trifluoromethyl-10H-phenothiazine (6) (2.10 g, 7.85 mmol) was dissolved in acetic acid (40 mL) and stirred at room temperature as a solution of bromine (2.52 g, 0.81 mL, 15.7 mmol) in acetic acid (10 mL) was added. The mixture was allowed to stir overnight at this condition. To this mixture sodium sulfite $Na_2SO_3$ (1.98 g, 15.7 mmol) and water (2 mL) were added. The mixture was stirred at room temperature for 3 h. After that reaction mixture was poured into 100 mL of ice-water contained NaOH (1.28 g, 32 mmol). The mixture was stirred overnight and filtered, gave light green solid (2.84 g, 84%).

6.0.1.63
3,7-Dibromo-1-trifluoromethyl-10-Boc-phenothiazine 3,7-Dibromo-1-trifluoromethyl-10H-phenothiazine (2.0 g, 4.7 mmol) was suspended in $CH_3CN$ (20 mL) and $(Boc)_2O$ (3.1 g, 14.2 mmol) and DMAP (0.57 g, 4.7 mmol) were added. The mixture was warmed to 50° C. After 5 min starting material was dissolved in solvent, $CO_2$ was eliminated and solid material formed. After 2 h the reaction mixture was cooled to room temperature. The solid was filtered off and dried on air (1.83 g, 74%).

6.0.1.64 3-(Bis(2-methoxyethyl)amino)-7-(4-(tert-butoxycarbonyl)piperazin-1-yl)phenothiazin-5-ium iodide Phenothiazin-5-ium iodide (400 mg, 0.567 mmol) was dissolved in $CHCl_3$ (20 mL) and bis(2-methoxyethyl)amine (0.17 mL, 1.13 mmol) was added dropwise. The mixture was stirred at RT overnight. The solvent was removed and the material was used without purification. The salt (200 mg, 0.281 mol) was dissolved in MeOH (20 mL) and a solution of N-Boc piperazine (105 mg, 0.562 mmol) was added. The mixture was stirred for 24 hrs and the solvent was removed by evaporation. The crude material was purified by flash silica gel chromatography to give a dark blue solid of the desired product.

6.0.1.65 3-(bis(2-methoxyethyl)amino)-7-(piperazin-1-yl)phenothiazin-5-ium-2,2,2-trifluoroacetate 3-(Bis(2-methoxyethyl)amino)-7-(4-(tert-butoxycarbonyl)piperazin-1-yl)phenothiazin-5-ium iodide was dissolved in $CH_2Cl_2$ and trifluoroacetic acid (1:1 mixture) and heated at 50° C. for 2 to 4 h. The mixture was allowed to cool to RT and the solvent was evaporated to give a residue, which was purified by flash silica gel chromatography. Isolated 15 mg of a dark blue solid as the desired product.

6.0.1.66 7-(4-(tert-butoxycarbonyl)piperazin-1-yl)-1-chloro-3-(diethylamino)phenothiazin-5-ium iodide 1-Chlorophenothiazin-5-ium Iodide (350 mg, 0.473 mmol) was dissolved in $CHCl_3$ (5 mL) and diethylamine (0.1 mL, 1.04 mmol) was added. The resulting mixture was allowed to stir at RT for 24 h. The solvent was removed and the crude material was used without purification. The crude material was dissolved in MeOH (5 mL) and 1-Boc-piperazine (177 mg, 0.95 mmol) was added as a solution in MeOH (2 mL) and thje mixture was stirred for 24 h. The solvent was evaporated and a portion of the material was purified by prep TLC to give 5.2 mg of a product.

6.0.1.67 1-chloro-3-(diethylamino)-7-(piperazin-1-yl)phenothiazin-5-ium 2,2,2-trifluoroacetate The 7-(4-(tert-butoxycarbonyl)piperazin-1-yl)-1-chloro-3-(diethylamino)phenothiazin-5-ium iodide was dissolved in $CH_2Cl_2$ (4 mL) and trifluoroactic acid (4 mL) and heated at 70° C. overnight. The mixture was allowed to cool to RT and the solvent was evaporated to give a residue. The residue was purified by Prep TLC to give 2.2 mg of the desired product.

6.0.1.68 7-(4-(tert-butoxycarbonyl)piperazin-1-yl)-3-(diethylamino)-1-ethylphenothiazin-5-ium iodide and 7-(4-(tert-butoxycarbonyl)piperazin-1-yl)-3-(diethylamino)-1-ethylphenothiazin-5-ium 1-Ethylphenothiazin-5-ium Iodide (350 mg, 0.473 mmol) was dissolved in $CHCl_3$ (5 mL) and diethylamine (0.1 mL, 1.05 mmol) was added. The resulting mixture was allowed to stir at RT for 24 h. The solvent was removed and the crude material was used without purification. The crude material was dissolved in MeOH (5 mL) and 1-Boc-piperazine (177 mg, 0.95 mmol) was added as a solution in MeOH (2 mL) and the mixture was stirred for 24 h. The solvent was evaporated and a portion of the material was purified by prep TLC to give 4.5 mg of the first isomer and 10 mg of the second isomer.

6.0.1.69 3 3-(diethylamino)-1-ethyl-7-(piperazin-1-yl)phenothiazin-5-ium 2,2,2-trifluoroacetate and 7-(diethylamino)-1-ethyl-3-(piperazin-1-yl)phenothiazin-5-ium 2,2,2-trifluoroacetate Each of the isomers was dissolved in $CH_2Cl_2$ (4 mL) and trifluoroactic acid (4 mL) and heated at 70° C. overnight. Each of the mixtures were allowed to cool to RT and the solvent was evaporated to give a residue for each isomer. The residue was purified by Prep TLC to give the two regioisomers. Alternatively, each regioisomer can be purified separately.

6.0.1.70 3-(bis(2-methoxyethyl)amino)-7-(4-(tert-butoxycarbonyl)piperazin-1-yl)-1-ethylphenothiazin-5-ium iodide and 7-(bis(2-methoxyethyl)-amino)-3-(4-(tert-butoxycarbonyl)piperazin-1-yl)-1-ethylphenothiazin-5-ium iodide 1-Ethylphenothiazin-5-ium iodide was dissolved in $CHCl_3$ (5 mL) and bis-(2-methoxyethyl)amine (0.22 mL, 1.5 mmol) was added. The resulting mixture was stirred at RT for 24 h. The solvent was evaporated and the residue was dissolved in DMF (10 mL), followed by N-Boc-piperazine (250 mg, 1.36 mmol) and $Cs_2CO_3$ (665 mg, 2.04 mmol). The mixture was stirred for 48 h at RT. The solvent was evaporated and the residue was purified by flash chromatography to give two regioisomer products (665 mg, 2.04 mmol). The mixture was stirred for 48 h at RT. The solvent was evaporated and the residue was purified by flash chromatography to give the desired product (7 mg of the first product and 10 mg of the second).

6.0.1.71 1,9-dichloro-3,7-di(piperazin-1-yl)phenothiazin-5-ium 2,2,2-trifluoroacetate tert-Butyl 3,7-dibromo-1,9-dichloro-10H-phenothiazine-10-carboxylate (540 mg, 1.03 mmol) was combined with $Pd_2(dba)_3$ (27 mg, 0.046 mmol), BINAP (40 mg, 0.063 mmol), sodium tert-butoxide (312 mg, 3 mmol), N-Boc-piperazine (200 mg, 1.1 mmol), and xylenes (10 mL). The resulting mixture was heated at 140° C. for 16 h. The mixture was allowed to cool to RT and the organic solvent was evaporated to give a residue which was purified by flash silica gel chromatography to give the 3-N-Boc piperazine and bis 3,7-N,N,-Boc-piperazine products. The bis-Boc-piperazine compound (20 mg, 0.027 mmol) was dissolved in $CH_2Cl_2$ (5 mL) and trifluoroacetic acid (5 mL) and heated to 70° C. or 16 h. The mixture was allowed to cool to RT and the organic solvent was evaporated to give a residue. The residue was purified by Prep TLC to give 4.2 mg of the desired product.

6.0.1.72 1,9-dichloro-3-(piperazin-1-yl)-7-(pyrrolidin-1-yl)phenothiazin-5-mum 2,2,2-trifluoroacetate tert-Butyl-7-bromo-3-(4-(tert-butoxycarbonyl)piperazin-1-yl)-1,9-dichloro-4-aH-phenothiazine-10(10aH)-carboxylate (225 mg, 0.356 mmol) was combined with $Pd_2(dba)_3$ (13 mg, 0.023 mmol), BINAP (19 mg, 0.031 mmol), sodium tert-butoxide (145 mg, 1.4 mmol), pyrrolidine (45 μL, 0.53 mmol), and xylenes (10 mL). The resulting mixture was heated at 140° C. for 16 h. The mixture was allowed to cool to RT and the organic solvent was evaporated to give a residue which was purified by flash silica gel chromatography to give 28 mg of a dark powder. The tert-butyl 3-(4-(tert-butoxycarbonyl)piperazin-1-yl)-1,9-dichloro-7-(pyrrolidin-1-yl)-4-aH-phenothiazine-10(10aH)-carboxylate was dissolved in $CH_2Cl_2$ (5 mL) and trifluoroacetic acid (5 mL) and heated to 70° C. or 16 h. The mixture was allowed to cool to RT and the organic solvent was evaporated to give a residue. The residue was purified by Prep TLC to give 10 mg of the desired product.

6.0.1.73 3-(bis(2-methoxyethyl)amino)-1,9-dichloro-7-(piperazin-1-yl)phenothiazin-5-ium 2,2,2-trifluoroacetate tert-Butyl 3,7-dibromo-1,9-dichloro-10H-phenothiazine-10-carboxylate (1.0 g, 1.89 mmol) was combined with $Pd_2(dba)_3$ (50 mg, 0.085 mmol), BINAP (40 mg, 0.063 mmol), sodium tert-butoxide (577 mg, 5.54 mmol), bis(2-methoxyethyl)amine (0.28 mL, 1.9 mmol), and xylenes (10 mL). The resulting mixture was heated at 140° C. for 16 h. The mixture was allowed to cool to RT and the organic solvent was evaporated to give a residue which was purified by flash silica gel chromatography to give 350 mg of the monobromo compound tert-butyl 7-(bis(2-methoxyethyl)amino)-3-bromo-1,9-dichloro-4-aH-phenothiazine-10(10aH)-carboxylate. Tert-butyl 7-(bis(2-methoxyethyl)amino)-3-bromo-1,9-dichloro-4-aH-phenothiazine-10(10aH)-carboxylate (125 mg, 0.22 mmol) was combined with $Pd_2(dba)_3$ (10 mg, 0.0168 mmol), BINAP (15 mg, 0.0195 mmol), $Cs_2CO_3$ (80 mg, 0.25 mmol), N-Boc-piperazine 60 mg, 0.32 mmol), and xylenes (10 mL). The mixture was heated at reflux for 16 h. The mixture was allowed to cool to RT and the organic solvent was evaporated under vacuum. The residue was dissolved in $CH_2Cl_2$ (5 mL) and trifluoroacetic acid (5 mL) and heated to 70° C. or 16 h. The mixture was allowed to cool to RT and the organic solvent was evaporated to give a residue. The residue was purified by Prep TLC to give 7.9 mg of the desired product.

6.0.1.74 Preparation of 1,9-diethyl-[3-dimethylamino-(4-methylpiperazinyl)-phenothiazinium iodide To the solution of 1,9-diethylphenothiazin-5-ium tetraiodide hydrate (0.203 g, 0.31 mmol) in chloroform 10 mL, was added dimethylamine solution in THF (0.31 mL, 0.62 mmol). The resulting mixture was stirred at room temperature for 3 h and concentrated to dryness. To the crude residue obtained was added anhydrous methanol 12 mL and 1-methylpiperazine (35 μL, 0.31 mmol), and stirred vigorously overnight and monitored by LCMS. The crude product was purified by chromatography on the Teledyne Isco combi flash using chloroform-methanol as the eluant to afford the title compound. MS (m/z):$[M+H]^+$=397 (neutral product).

6.0.1.75 Preparation of 1,9-diethyl-3-dimethylamino-7-[4-isopropylpiperazinyl]-phenothiazinium iodide This compound was prepared as described above, except that isopropylpiperazine was used in the secondamination step. The crude was purified on the Teledyne Isco combi-flash using chloroform-methanol as the eluant to provide the title compound. MS (m/z):$[M+H]^+$=425 (neutral product).

6.0.1.76 Preparation of 3-(butyl(methyl)amino-1,9-dimethyl-7-(4-methylpiperazin-1-yl)phenothiazin-5-ium iodide To the solution of 1,9-dimethyl-7-(methylpiperazin-1-yl) phenothiazin-5-ium triiodide (150 mgs, 0.21 mmol) in anhydrous methanol 10 mL was added N-methylbutylamine (200 μL, 1.7 mmol). The resulting mixture was stirred vigorously at room temperature overnight, monitored by LCMS. The crude was purified as usual using chloroform-methanol as eluant to provide the title compound. MS (m/z):$[M+H]^+$=411 (neutral product).

6.0.1.77 Preparation of 3-(dimethylamino)-1,9-diethyl-7-(4-trifluoromethylsulfonyl)piperazin-1-yl) phenothiazin-5-ium iodide To the solution of the 1,9-diethylphenothiazin-5-ium tetraiodide hydrate (0.20 mg, 0.31 mmol) in chloroform 5 mL, was added the mixture of 1-(trifluoromethylsulfonyl)piperazine hydrochloride (158 mg, 0.62 mmol), triethylamine in chloroform was prepared by the treatment of boc-piperazine with diisopropylethylamine and trifluoromethanesulfonyl chloride in anhydrous 1,2-dichloroethane (DCE), after extractive workup was concentrated. The resulting product was treated with 4 M HCl in Dioxane and 1,2-dichloroethane at room temperature to furnish the aniline. The resulting mixture was stirred vigorously at room temperature monitored by LCMS; 0.3 h later, it was concentrated to dryness, treated with dimethylamine-in-THF and anhydrous methanol and stirred at room temperature for 18 h. The crude was purified as usual using chloroform-methanol as the eluant to provide the title compound. MS (m/z):$[M+H]^+$=515 (neutral product).

6.0.1.78 Preparation of -(4-tert-butoxycarbonyl)-1,4-diazepan-1-yl)-1,9-diethyl-7-(4-ureidopiperidin-1-yl) phenothiazin-5-ium iodide To the solution of the triiodide hydrate (0.255 g, 0.39 mmol) in chloroform 6 mL, was added the mixture of piperidin-4-yl-urea hydrochloride (0.14 g, 0.78 mmol) and triethylamine in chloroform 6 mL. The resulting mixture was stirred at room temperature for 3 h and concentrated to dryness. To the crude obtained was added anhydrous methanol 12 mL and boc-homopiperazine (0.5 g, 2.5 mmol) and stirred at room temperature for 18 h, and purified as usual using chloroform-methanol as eluant to provide the title compound. MS (m/z): [M+H]=595 (neutral product).

6.0.1.79 Preparation of 3-(1,4-diazepan-1-yl)-1,9-diethyl-7-(4-ureidopiperidin-1-yl)phenothiazin-5-ium 2,2,2-trifluoroacetate To the solution of the above compound in 1,2-dichloroethane 5 mL was added trifluoroacetic acid (TFA) 0.5 mL. The resulting solution was stirred at room temperature, monitored by LCMS. MS (m/z):$[M+H]^+$=495 (neutral product).

6.0.1.80 Preparation of 3,7-di(1,4-diazepan-1-yl)-1,9-diethylphenothiazin-5-ium 2,2,2-trifluoroacetate To the solution of the triiodide hydrate (28 g, 0.43 mmol) in chloroform 12 mL was added the solution of boc-homopiperazine (0.43 g, 2.15 mmol), stirred at room temperature for 18 h and purified as usual using chloroform-methanol as eluant to provide the intermediate. Treatment of with TFA in 1,2-dichloroethane (DCE) provided the title compound. MS (m/z):$[M+H]^+$=452 (neutral product).

6.0.1.81 Preparation of 3-(4-(tert-butoxycarbonyl)-1,4-diazepan-1-yl)-1,9-diethyl-7-(2-methylpyrrolidin-1-yl)phenothiazin-5-ium iodide To the solution of the triiodide hydrate (0.28 g, 0.43 mmol) in chloroform 6 mL, was added the solution of boc-homopiperazine (17 g, 0.87 mmol) in chloroform 6 mL. The resulting mixture was stirred at room temperature for 3 h and concentrated to dryness. To the residue obtained was added anhydrous methanol 10 mL and a solution of 2-methylpyrrolidine (0.23 g, 2.68 mmol) in methanol 2 mL, stirred at room temperature for 18 h and purified as usual using chloroform-methanol to provide the title compound. MS (m/z): $[M+H]^+$=537 (neutral product).

6.0.1.82 Preparation of 3-(1,4-diazepan-1-yl)-1,9-diethyl-7-(2-methylpyrrolidin-1-yl)phenothiazin-5-ium 2,2,2-trifluoroacetate This compound was prepared by analogy to 3,7-di(1,4-diazepan-1-yl)-1,9-diethylphenothiazin-5-ium 2,2,2-trifluoroacetate described above. MS (m/z):[M+H]+437 (neutral product).

6.0.1.83 Preparation of 3-(4-(cyclopentylsulfonyl)piperazin-1-yl)-7-(dimethylamino)-1,9-diethylphenothiazin-5-ium iodide To the solution of the triiodide hydrate (0.22 g, 0.34 mmol) in chloroform 5 mL, was added the mixture of 1-(cyclopentylsulfonyl)piperazine hydrochloride (0.15 g, 0.58 mmol), triethylamine in chloroform 5 mL (was prepared by treating boc-piperazine with cyclopentylsulfonyl chloride and Hunig's base in anhydrous 1,2-dichloroethane. The product was isolated by extractive workup, and treated with 4 M HCl-in-Dioxane and DCE at room temperature to afford the hydrochloride salt). The resulting mixture was stirred at room temperature for 3 h and concentrated to dryness. The crude obtained was treated with dimethylamine and methanol, stirred at room temperature for 18 h, purified as usual to provide the title compound. MS (m/z):$[M+H]^+$=515 (neutral product).

6.0.1.84 Preparation of 3,7-bis(4-(tert-butoxycarbonyl)-1,4-diazepan-1-yl)-1,9-diethylphenothiazin-5-ium iodide See above. MS (m/z):[M+H]+=652 (neutral compound).

6.0.1.85 Preparation of 3,7 bis(4(cyclopropanecarbonyl)piperazin1yl)1,9-diethylphenothiazin5ium iodide To the solution of the triiodide hydrate (0.34 g, 0.53 mmol) in chloroform 6 mL was added the mixture of cyclopropyl (piperazin-1-yl)methanone hydrochloride (0.2 g, 1.05 mmol), triethylamine in chloroform 6 mL was prepared by treating Boc-piperazine with cyclopropanecarbonyl chloride, Hunig's base in DCE. The product obtained was Boc-deprotected with 4 M HCl-in Dioxane and DCE to afford the hydrochloride salt.). The reaction mixture was stirred at room temperature overnight and purified as usual to provide the title compound. MS (m/z):$[M+H]^+$=560 (neutral compound).

6.0.1.86 Preparation of 1,9-diethyl-3-morpholino-7-(4-sulfamoylpiperazin-1-yl)phenothiazin-5-ium iodide To the solution of the triiodide hydrate (0.23 g, 0.35 mmol) in chloroform was added the mixture of piperazine-1-sulfonamide hydrochloride (0.14 g, 0.70 mmol), triethylamine in chloroform. (was prepared by reacting sulfamoyl chloride with three equivalents of Boc-piperazine in ethyl acetate at room temperature overnight. On completion, the reaction mixture was diluted with ethyl acetate washed sequentially with 0.5 M HCl, water, brine, dried, filtered and concentrated to dryness. The product obtained was Boc-deprotected as usual to afford the hydrochloride salt). The reaction mixture was stirred for 3 h, concentrated to dryness, treated with morpholine, methanol and stirred at room temperature overnight, as usual to provide the title compound. MS (m/z):[M+H]±504 (neutral compound).

6.0.1.87 Preparation of 3-(4-(tert-butoxycarbonyl)-3-(methoxycarbonyl)-piperazin-1-yl)-1,9-diethyl-7-morpholinophenothiazin-5-ium iodide The mixture of the triiodide hydrate (0.28 g, 0.42 mmol) and N—I-boc-2-piperazinecarboxylic acid methyl ester (0.21 g, 0.84 mmol) in chloroform 12 mL for 3 h and concentrated to dryness. The residue obtained was treated with morpholine in methanol as usual. After the usual purification, the title compound was obtained. MS (m/z):$[M+H]^+$=583. (neutral product).

6.0.1.88 Preparation of 3-(dimethylamino)-9-ethyl-1-isopropyl-7-(4-iso-propylpiperazin-1-yl)phenothiazin-5-ium iodide To the solution of 1-ethyl-9-isopropylphenothiazin-5-ium (0.23 g, 0.35 mmol) prepared analogously to that shown above in chloroform 10 mL, was added isopropylpiperazine (101 μL, 0.71 mmol). The resulting mixture was stirred at room temperature for 3 h and concentrated to dryness, crude obtained treated with methanol, dimethylamine for 18 h. Purification as usual provided the title compound. MS (m/z): [M+H]=439. (neutral product).

6.0.1.89 Preparation of 3,7-bis(4-(cyclopropylsulfonyl)piperazin-1-yl)-1,9-diethyl-phenothiazin-5-ium iodide To the solution of the triiodide hydrate in chloroform was added the mixture of 1-(cyclopropylsulfonyl)piperazine hydrochloride triethylamine in chloroform (prepared analogously as using cyclopropanesulfonyl chloride). Boc-Deprotection with 4 M HCl afforded the hydrochloride salt, a mixture of triethylamine in chloroform was stirred at room temperature for 18 h and purified as usual to provide the title compound. MS (m/z):[M+H]±633 (neutral product).

6.0.1.90 Preparation of 3-(butyl(methyl)amino)-7-(4-cyclopropylsulfonyl)piperazin-1-yl)1,9-diethylphenothiazin-5-ium iodide The mixture of 1,9-diethylphenothiazin-5-ium iodide (4 g, 0.63 mmol), (0.29 g, 1.27 mmol) and triethylamine in chloroform 20 mL was stirred at room temperature for 3 h and concentrated to dryness. To the residue obtained was added methanol and N-methylbutylamine, stirred at room temperature for 18 h, purified as usual to provide the title compound. MS (m/z):$[M+H]^+$=529 (neutral product).

6.0.1.91 Preparation of 3-(4-(cyclopropylsulfonyl)-1,4-diazepin-1-yl)-7-(dimethylamino)-1,9-diethylphenothiazin-5-ium iodide To the solution of 1,9-diethylphenothiazin-5-ium (0.35 g, 0.54 mmol) in chloroform 5 mL, was added the mixture of 1-(cyclopropylsulfonyl)sulfonyl-1,4-diazepane hydrochloride (0.26 g, 1.08 mmol) and, triethylamine in chloroform was prepared analogously using Boc-homopiperazine). After stirring for 3 h, it was concentrated to dryness, methanol and dimethylamine added, stirred for 18 h, purified to provide the title compound. MS (m/z):[M+H]+=501 (neutral product).

6.0.1.92 Preparation of 3-(4-cyclopentylpiperazin-1-yl)-7-(dimethylamino)-1,9-diethylphenothiazin-5-ium iodide The mixture of 1,9-diethylphenothiazin-5-ium (0.27 g, 0.42 mmol), and 1-cyclopentylpiperazine (0.13 g, 0.84 mmol) in chloroform 10 mL was stirred at room temperature for 3 h, concentrated to dryness and treated with dimethylamine as usual. Purification provided the title compound. MS (m/z):$[M+H]^+$=451 (neutral product).

6.0.1.93 Preparation of 3-(dimethylamino)-1,9-diethyl-7-(methylsulfonyl)-1,4-diazepan-1-yl)phenothiazin-5-ium iodide The mixture of 1-(methylsulfonyl)-1,4-diazepane hydrochloride (0.14 g, 0.66 mmol) and triethylamine in chloroform 5 mL was added to the solution of 1,9-diethylphenothiazin-5-ium (0.22 g, 0.33 mmol) in chloroform 5 mL prepared analogously as using methanesulfonic anhydride and Boc-homopiperazine). After 3 h of stirring, it was concentrated to dryness, treated with dimethylamine as usual, and purified to provide the title compound. MS (m/z):[M+H]±−475. (neutral product).

6.0.1.94 Preparation of 3-(dimethylamino)-1,9-diethyl-7-(4-(ethylsulfonyl)-1,4-diazepan-1-yl)phenothiazin-5-ium iodide The preparation was analogous to that shown above, except that the 1-(ethylsulfonyl)-1,4-diazepane hydrochloride prepared by employing ethanesulfonyl chloride was used. MS (m/z):$[M+H]^+$=489 (neutral product).

6.0.1.95 Preparation of 3-(dimethylamino)-1,9-diethyl-7-(4-(2-methoxyethyl)piperazin-1-yl)phenothiazin-5-ium iodide The mixture of 1,9-diethylphenothiazin-5-ium (0.20 g, 0.31 mmol), 1-(2-methoxyethyl)piperazine (92 μL, 0.62 mmol) in chloroform 10 mL, was stirred at room temperature as usual, then treated with dimethylamine in methanol. Purification as usual provided the title compound. MS (m/z):[M+H]+=457 (neutral compound).

6.0.1.96 Preparation of 3-(4-(cyclopropylsulfonyl)piperazin-1-yl)-7-(dimethylamino)-1-ethyl-9-isopropylphenothiazin-5-ium iodide The preparation was analogous to that shown above, except that 1-(cyclopropylsulfonyl)piperazine hydrochloride was employed. MS (m/z):[M+H]+=500 (neutral compound).

6.0.1.97 Preparation of 3-(dimethylamino)-9-ethyl-1-isopropyl-7-(4-trifluoromethylsulfonyl)piperazin-1-yl)phenothiazin-5-ium iodide The procedure was analogous to that shown above, except that the 1-ethyl-9-isopropylphenothiazine triiodide hydrate was used in place of the diethylphenothiazin-5-ium. MS (m/z):[M+H]+=528 (neutral compound).

6.0.1.98 Preparation of 3-(4-(tert-butylcarbamoyl)-1,4-diazepan-1-yl)-7-(dimethylamino)-1,9-diethylphenothiazin-5-ium iodide The mixture of 1,9-diethylphenothiazin-5-ium (0.21 g, 0.32 mmol), triethylamine and N-tert-butyl-1,4-diazepane-1-carboxamide hydrochloride (0.15 g, 0.65 mmol) in chloroform 10 mL was prepared by reacting Boc-homopiperazine with tert-butyl isocyanate and Hunig's base in DCE, followed by the usual Boc-deprotection to afford the hydrochloride salt) was stirred at room temperature for 3 h, concentrated, treated with dimethylamine in methanol, purified to provide the title compound. MS (m/z):$[M+H]^+$=496 (neutral compound).

6.0.1.99 Preparation of 3-(dimethylamino)-1,9-diethyl-7-(4-sulfamoyl-1,4-diazepan-1-yl)phenothiazin-5-ium iodide The mixture of (0.18 g, 0.28 mmol), triethylamine and 1,4-diazepane-1-sulfonamide hydrochloride (0.082 g, 0.38 mmol) in chloroform 10 mL, was stirred at room for 3 h and concentrated to dryness (analogously to that described above, except that Boc-homopiperazine was used). The crude obtained was treated with dimethylamino in methanol for 18 h, purified to provide the title compound. MS (m/z):$[M+H]^+$=476 (neutral product).

6.0.1.100 Preparation of 3-(dimethylamino)-1,9-diethyl-7-(4-(isopropylsulfonyl)-1,4-diazepan-1-yl)phenothiazin-5-ium iodide The mixture of 1,9-diethylphenothiazin-5-ium (0.22 g, 0.33 mmol), triethylamine and 1-(isopropylsulfonyl)-1,4-diazepane hydrochloride (0.16 g, 0.66 mmol) in chloroform 10 mL, was stirred at room temperature for 3 h and concentrated to dryness (analogously to using isopropylsulfonyl chloride). The crude obtained was treated with dimethylamine and methanol, purified to provide the title compound. MS (m/z): [M+H]±503 (neutral compound).

6.0.1.101 Preparation of 3-(dimethylamino)-1,9-diethyl-7-(4-(methylbut-2-enyl)-1,4-diazepan-1-yl) phenothiazin-5-ium iodide The mixture of 1,9-diethylphenothiazin-5-ium (0.22 g, 0.33 mmol), triethylamine and 1-(3-methylbut-2-enyl)-1,4-diazepane hydrochloride (0.14 g, 0.66 mmol) in chloroform 10 mL, was stirred at room temperature for 3 h and concentrated to dryness. (was prepared by treating Boc-homopiperazine with prenyl bromide and potassium carbonate in N,N-dimethylformamide (DMF). After extractive workup, the product obtained was Boc-deprotected as usual to furnish the hydrochloride salt). The crude obtained was treated with dimethylamino in methanol, purified to provide the title compound. MS (m/z):$[M+H]^+$=465 (neutral compound).

6.0.1.102 Preparation of 3-(dimethylamino)-7-(4-(N,N-dimethylsulfamoyl)piperazin-1-yl)-1,9-diethylphenothiazin-5-ium iodide The mixture of 1,9-diethylphenothiazin-5-ium (0.21 g, 0.32 mmol) and piperazine-1-sulfonic acid dimethylamide (0.12 g, 0.64 mmol) in chloroform 10 mL, was stirred at room for 3 h, concentrated, treated with dimethylamine in methanol. Purification provided the title compound. MS (m/z):$[M+H]^+$=490 (neutral product).

6.0.1.103 Preparation of 3-(4-(cyclopropylsulfonyl) piperazin-1-yl)-7-(dimethylamino)-1,9-diethylphenothiazin-5-ium iodide The mixture of 1,9-diethylphenothiazin-5-ium (0.20 g, 0.30 mmol), triethylamine and (0.14 g, 0.60 mmol) in chloroform 10 mL, was stirred for 3 h and concentrated to dryness. Then treated with dimethylamine in methanol, purified to provide the title compound. MS (m/z):[M+H]+=487 (neutral compound).

6.0.1.104 Preparation of 3-(4-tert-butylcarbamoyl) piperazin-1-yl)-7-(dimethylamino)-1,9-diethylphenothiazin-5-ium iodide The mixture of 1,9-diethylphenothiazin-5-ium (0.21 g, 0.32 mmol), triethylamine and N-tert-butylpiperazine 1-carboxamide hydrochloride (0.15 g, 0.68 mmol) in chloroform and stirred for 3 h and concentrated to dryness (analogously as described above, except Boc-piperazine was used). The usual treatment with dimethylamine in methanol followed by purification provided the title compound. MS (m/z):$[M+H]^+$=482.

6.0.1.105 Preparation of 3-(4-(tert-butoxycarbonyl)-1,4-diazepan-1-yl)-7-(dimethylamino-1,9-diethylphenothiazin-5-ium iodide 1,9-Diethylphenothiazin-5-ium (0.24 g, 0.37 mmol) and Boc-homopiperazine (0.2 g, 0.99 mmol) in chloroform were stirred for 3 h, concentrated to dryness, and the residue treated with dimethylamine in methanol. The crude was purified to provide the title compound. MS (m/z):$[M+H]^+$=497 (neutral product).

6.0.1.106 Preparation of 3-(1,4-diazepan-1-yl)-7-(dimethylamino)-1,9-diethylphenothiazin 2,2,2-trifluoroacetate This compound was obtained by the Boc-deprotection of the preceeding compound using TFA in DCE. MS (m/z):[M+H]+=397 (neutral product).

6.0.1.107 Preparation of 3-(4-butylpiperazin-1-yl)-7-(dimethylamino)-1,9-diethylphenothiazin-5-ium iodide The mixture of (0.21 g, 0.32 mmol) and 1-butylpiperazine (0.10 g, 0.70 mmol) in chloroform was stirred for 3 h and concentrated to dryness. Treatment of the crude with dimethylamine in methanol, followed by purification provided the title compound. MS (m/z): [M+H]+=439 (neutral compound).

6.0.1.108 N-Acetyl-2-trifluoromethylaniline

Commercial 2-trifluoromethylaniline (13.5 g, 83.9 mmol) was dissolved in acetic anhydride (55 mL, 580.0 mmol) and stirred at room temperature for 1 h. Then the reaction mixture was poured into $H_2O$, the whole was extracted with ethyl acetate (2×300 mL). The combined organic extracts were washed with 5% aqueous $NaHCO_3$, brine, dried ($K_2CO_3$), filtered and concentrated to provide the title compound as a white solid (15.7 g, 92%).

6.0.1.109 N-Acetyl-2-trifluoromethyldiphenylamine

A mixture of the N-acetyl-2-trifluoromethylaniline (6.1 g, 30.0 mmol), anhydrous $K_2CO_3$ (4.1 g, 30.0 mmol), CuI (210 mg, 1.1 mmol) and bromobenzene (16 mL, 160 mmol) was stirred and heated at 175° C. to 180° C. under an argon atmosphere for 48 h. After cooling the reaction mixture was poured into ice-$H_2O$ and extracted with ethyl acetate (2×200 mL), the combined organic extracts were washed with brine, dried over anhydrous $K_2CO_3$, filtered and concentrated to dryness. The obtained crude material was purified by flash chromatography (using ethyl acetate-hexane as an eluent) to afford the N-acetyl-2-trifluoromethyldiphenylamine (5.4 g, 64%).

6.0.1.110 2-Trifluoromethyldiphenylamine

A solution of the N-acetyl-2-trifluoromethyldiphenylamine (3.5 g, 12.5 mmol) in 10% KOH (2 g, 36 mmol)/EtOH (20 mL) was stirred and refluxed for 6 h, then poured into $H_2O$. The mixture was extracted with ethyl acetate (2×100 mL). The combined organic layers were washed with brine, dried ($Na_2SO_4$), filtered and concentrated to dryness, gave dark red oil (2.5 g, 85%).

6.0.1.111 2-Trifluoromethyl-10H-phenothiazine

To 2-trifluoromethyldiphenylamine (1.1 g, 4.6 mmol), sulfur (295 mg, 9.2 mmol) and iodine (328 mg, 1.29 mmol) were combined. Vial was charged with balloon for discharge. The heating block was preheated (150° C.). The vial was heated on the heating block and after 15 min. Temperature was increased to 210° C., reaction mixture was stirred and heated for an additional 45 min and cooled. The dark solid material was dissolved in mixture methanol/chloroform and purified by flash chromatography (ethyl acetate-hexane as an eluent) to afford the desired product (450 mg, 36%).

1-Trifluoromethyl-3,7-di(4-methylpiperazin-1-yl) phenothiazin-5-ium bromide 6.0.1.112 1-Trifluoromethyl-3,7-dibromophenothiazin-5-ium bromide 1-Trifluoromethyl-10H-phenothiazine (725 mg, 2.72 mmol) was dissolved in glacial acetic acid (20 mL) and a solution of bromine (2.8 mL, 54.3 mmol) also in acetic acid (30 mL) was added to it all at once with vigorous stirring; stirring was continued for about 1-2 min, then water (150 mL) was added to the mixture, the red precipitate was filtered, washed with $Et_2O$, dried under vacuum to afford product (0.27 g, 20%).

6.0.1.113 1-Trifluoromethyl-3,7-di(4-methylpiperazin-1-yl)phenothiazin-5-ium bromide To the stirred solution of 1-trifluoromethyl-3,7-dibromophenothiazin-5-ium bromide (300 mg, 0.6 mmol) in chloroform (10 mL) 1-methylpiperazine (350 mg, 3.5 mmol) in chloroform (10 mL) was added all at once with vigorous stirring at room temperature. The resulting mixture was stirred at room temperature 3 h, concentrated to dryness. The crude product was purified by flash chromatography methanol-chloroform as an eluent) to provide the title compound.

6.0.1.114 1-Trifluoromethylphenothiazin-5-ium tetraiodide hydrate

A solution of 1-trifluoromethyl-10H-phenothiazine (1.55 g, 5.81 mmol) in anhydrous chloroform (50 mL) was stirred at 5° C. and the solution of iodine (4.42 g, 17.41 mmol) in $CHCl_3$ (250 mL) was added drop wise (addition funnel) over 1 h. The resulting dark solution was stirred for an additional 3 h at 5° C., monitored by TLC. After the disappearance of the starting material, the resulting precipitate was filtered, washed with a copious amount of chloroform, dried overnight in vacuum to afford a dark solid (3.50 g, 76%).

7-(Dimethylamino)-1-trifluoromethyl-3-(4-methylpiperazin-1-yl)phenothiazin-5-ium iodide 6.0.1.115 7-(Dimethylamino)-1-trifluoromethylphenothiazin-5-ium triiodide To the stirred mixture of 1-trifluorophenothiazin-5-ium tetraiodide hydrate (920 mg, 1.1 mmol) in anhydrous $CHCl_3$ (20 mL) dimethylamine (1.1 mL, 2.2 mmol, 2 M solution in THF) was added drop wise over 4 h. The resulting mixture was stirred at room temperature overnight, concentrated to dryness.

6.0.1.116 7-(Dimethylamino)-1-trifluoromethyl-3-(4-methylpiperazin-1-yl)-phenothiazin-5-ium iodide A solution of 7-(dimethylamino)-1-trifluoromethylphenothiazin-5-ium triiodide (100 mg, 0.15 mmol) in methanol (10 mL) and 4-methylpiperazine (0.02 mL, 0.15 mmol) was stirred for 4 h at room temperature. The resulting mixture was concentrated to dryness and purified by flash chromatography using the methanol-chloroform gradient to provide the title compound.

6.0.1.117 7-(Dimethylamino)-1-trifluoromethyl-3-(4-Boc-piperazin-1-yl)-phenothiazin-5-ium iodide A solution of 7-(dimethylamino)-1-trifluoromethylphenothiazin-5-ium triiodide (100 mg, 0.15 mmol) in methanol (10 mL) and 1-Boc-piperazine (28 mg, 0.15 mmol) was stirred for 4 h at room temperature. The resulting mixture was concentrated to dryness and purified by flash chromatography using the methanol-chloroform gradient to provide the title compound.

6.0.1.118 3,7-(Di(4-Boc-piperazin-1-yl)-1-trifluoromethylphenothiazin-5-ium iodide A solution of 1-trifluoromethylphenothiazin-5-ium tetraiodide hydrate (150 mg, 0.19 mmol) in methanol (10 mL) and 1-Boc-piperazine (93 mg, 0.5 mmol) was stirred for 4 h at room temperature. The resulting mixture was concentrated to dryness and purified by flash chromatography using the methanol-chloroform gradient to provide the title compound.

6.0.1.119 7-(Dimethylamino)-1-trifluoromethyl-3-(piperazin-1-yl)phenothiazin-5-ium trifluoroacetate A solution of 7-(dimethylamino)-1-trifluoromethyl-3-(4-Boc-piperazin-1-yl)-phenothiazin-5-ium iodide (50 mg) in dichloromethane (5 mL) and trifluoroacetic acid (0.5 mL) was stirred for 2 h at room temperature. The resulting mixture was concentrated to dryness, rinsed out by toluene (3×10 mL) and dried under vacuum to provide the title compound.

3-7-Dibromo-1-trifluoromethyl-10-Boc-phenothiazine 6.0.1.120 3,7-Dibromo-1-trifluoromethyl-10H-phenothiazine 1-Trifluoromethyl-10H-phenothiazine (2.10 g, 7.85 mmol) was dissolved in acetic acid (40 mL) and stirred at room temperature as a solution of bromine (2.52 g, 0.81 mL, 15.7 mmol) in acetic acid (10 mL) was added. The mixture was allowed to stir overnight at this condition. To this mixture $Na_2SO_3$ (1.98 g, 15.7 mmol) and water (2 mL) were added. The mixture was stirred at room temperature for 3 h. After that reaction mixture was poured into 100 mL of ice-water contained NaOH (1.28 g, 32 mmol). The mixture was stirred overnight and filtered, gave light green solid (2.84 g, 84%).

6.0.1.121 3,7-Dibromo-1-trifluoromethyl-10-Boc-phenothiazine 3,7-Dibromo-1-trifluoromethyl-10H-phenothiazine (2.0 g, 4.7 mmol) was suspended in $CH_3CN$ (20 mL) and $(Boc)_2O$ (3.1 g, 14.2 mmol) and DMAP (0.57 g, 4.7 mmol) were added. The mixture was warmed to 50° C. After 5 min starting material was dissolved in solvent, $CO_2$ was eliminated and solid material formed. After 2 h the reaction mixture was cooled to room temperature. The solid was filtered off and dried on air (1.83 g, 74%).

3-(4-methylpiperazin-1-yl)-7-(pyrrolidin-1-yl)-1-trifluoromethylphenothiazin-5-ium trifluoroacetate 6.0.1.122 7-(Pyrrolidin-1-yl)-3-bromo-1-trifluoromethyl-10-Boc-phenothiazine To a stirred solution of 3,7-dibromo-1-trifluoromethyl-10-Boc-phenothiazine (18) (104 mg, 0.2 mmol) in xylenes (5 mL) $Pd(dba)_2$ (5.8 mg, 0.01 mmol), BINAP (4.4 mg, 0.007 mmol), $Cs_2CO_3$ (325 mg, 1.0 mmol) and pyrrolidine (0.017 mL, 14.2 mg, 0.2 mmol) were added. The mixture was refluxed for 48 h. After that reaction mixture was filtered, solvent was removed under vacuum. Product was used without additional purification.

6.0.1.123 3-(4-Methylpiperazin-1-yl)-7-(pyrrolidin-1-yl)-1-trifluoromethyl-10-Boc-phenothiazine To a stirred solution of 7-(pyrrolidin-1-yl)-3-bromo-1-trifluoromethyl-10-Boc-phenothiazine (30 mg, 0.058 mmol) in xylenes (5 mL) $Pd(dba)_2$ (1.7 mg, 0.003 mmol), BINAP (1.3 mg, 0.002 mmol), $Cs_2CO_3$ (94.5 mg, 0.29 mmol) and 1-methylpiperazine (8.7 mg, 0.01 mL, 0.087 mmol) were added. The mixture was refluxed for 48 h. After that reaction mixture was filtered, solvent was removed under vacuum. Product was used without additional purification.

6.0.1.124 3-(4-methylpiperazin-1-yl)-7-(pyrrolidin-1-yl)-1-trifluoromethylphenothiazin-5-ium trifluoroacetate To a solution 3-(4-methylpiperazin-1-yl)-7-(pyrrolidin-1-yl)-1-trifluoromethyl-10-Boc-phenothiazine (20 mg) in $CH_2Cl_2$ (2 mL) trifluoroacetic acid (0.5 mL) was added. The reaction mixture was stirred at 50° C. for 10 h. Solvent was removed under vacuum; product was purified by flash chromatography (solvent system-dichloromethanemethanol as an eluent).

3,7-di(piperazin-1-yl)-1-trifluoromethylphenothiazin-5-ium trifluoroacetate 6.0.1.125 3,7-di(4-Boc-piperazin-1-yl)-1-trifluoromethyl-10-Boc-phenothiazine To a stirred solution of 3,7-dibromo-1-trifluoromethyl-10-Boc-phenothiazine (373 mg, 0.71 mmol) in xylenes (10 mL) $Pd(dba)_2$ (21 mg, 0.36 mmol), BINAP (15.6 mg, 0.025 mmol), $Cs_2CO_3$ (1.16 g, 3.6 mmol) and 1-Boc-piperazine (335 mg, 1.8 mmol) were added. The mixture was refluxed for 24 h. After that reaction mixture was cooled, filtered, solvent was removed under vacuum. Product was used without additional purification.

6.0.1.126 3,7-dipiperazinyl-1-trifluoromethylphenothiazin-5-ium trifluoroacetate To a solution 3,7-di(4-Boc-piperazin-1-yl)-1-trifluoromethyl-10-Boc-phenothiazine (50 mg) in $CH_2Cl_2$ (5 mL) trifluoroacetic acid (0.5 mL) was added. The reaction mixture was stirred at 50° C. for 10 h. Solvent was removed under vacuum; product was purified by flash chromatography (solvent system-dichloromethane-methanol as an eluent).

6.0.1.127 3,7-Di(1,4-diazepan-1-yl)-1-trifluoromethylphenothiazin-5-ium trifluoroacetate 6.0.1.128 3,7-Di(4-Boc-azepan-1-yl)-1-trifluoromethyl-10-Boc-phenothiazine To a stirred solution of 3,7-dibromo-1-trifluoromethyl-10-Boc-phenothiazine (208 mg, 0.4 mmol) in xylenes (5 mL) $Pd(dba)_2$ (11.5 mg, 0.02 mmol), BINAP (9 mg, 0.014 mmol), $Cs_2CO_3$ (652 mg, 2 mmol) and 1-Boc-1,4-homopiperazine (100 mg, 0.5 mmol) were added. The mixture was heated at 100° C. for 48 h with vigorous stirring. After cooling reaction mixture was filtered, solvent was removed under vacuum. Product was used without additional purification.

6.0.1.129 3,7-Di(1,4-diazepan-1-yl)-1-trifluoromethylphenothiazin-5-ium trifluoroacetate To a solution 3,7-di(4-Boc-azepan-1-yl)-1-trifluoromethyl-10-Boc-phenothiazine (50 mg) in $CH_2Cl_2$ (5 mL) trifluoroacetic acid (0.5 mL) was added. The reaction mixture was stirred at 50° C. for 3 h. Solvent was removed under vacuum; product was purified by flash chromatography (solvent system-dichloromethane-methanol as an eluent).

7-(Bis(2-methoxyethyl)amino)-3-(piperazin-1-yl)-1-(trifluoromethyl)phenothiazin-5-ium trifluoroacetate 6.0.1.130 7-(Bis(2-methoxyethyl)amino)-3-bromo-1-trifluoromethyl-10-Boc-phenothiazine To a stirred solution of 3,7-dibromo-t-trifluoromethyl-10-Boc-phenothiazine (525 mg, 1.0 mmol) in xylenes (15 mL) $Pd(dba)_2$ (28.8 mg, 0.05 mmol), BINAP (21.8 mg, 0.035 mmol), $Cs_2CO_3$ (1.63 g, 5.0 mmol) and di(2-methoxyethyl) amine (120 mg, 0.9 mmol) were added. The mixture was refluxed with stirring for 24 h. After cooling solid material was filtered off and solvent was removed under vacuum. Product was used without additional purification.

6.0.1.131 7-(Bis(2-methoxyethyl)amino)-3-(4-Boc-piperazin-1-yl)-1-trifluoromethyl-10-Boc-phenothiazine To a stirred solution of 7-(bis(2-methoxyethyl)amino)-3-bromo-t-trifluoromethyl-10-Boc-phenothiazine (57 mg, 0.1 mmol) in xylenes (5 mL) $Pd(dba)_2$ (2.9 mg, 0.005 mmol), BINAP (2.1 mg, 0.003 mmol), $Cs_2CO_3$ (225 mg, 0.69 mmol) and 4-Boc-piperazine (37.2 mg, 0.2 mmol) were added. The mixture was refluxed for 48 h. After cooling reaction mixture was filtered, solvent was removed under vacuum. Product was used without additional purification.

6.0.1.132 7-(Bis(2-methoxyethyl)amino)-3-(piperazin-1-yl)-1-(trifluoromethyl)phenothiazin-5-ium trifluoroacetate To a solution of 7-(bis(2-methoxyethyl)amino)-3-(4-Boc-piperazin-1-yl)-1-trifluoromethyl-10-Boc-phenothiazine (20 mg) in $CH_2Cl_2$ (5 mL) trifluoroacetic acid (2 mL) was added. The reaction mixture was stirred at 50° C. for 4 h. Solvent was removed under vacuum; product was purified by flash chromatography (solvent system-dichloromethane-methanol as an eluent).

3,7-Di(4-methylpiperazin-1-yl)-1-n-butylphenothiazin-5-ium bromide 6.0.1.133 1-n-Butyl-10H-phenothiazine To a solution of 2-chloro-10H-phenothiazine (1.17 g, 5.0 mmol) in anhydrous ether (50 mL) n-butyllithium (10 mL, 25 mmol, 2.5 m solution in hexane) was added drop wise for 1 h at room temperature. After that mixture had been stirred for 6 h, ice-water was added and the stirring was continued for 30 min. The organic layer was separated and combined with ether extracts of the aqueous phase. The combined organic phases were washed with water, dried ($Na_2SO_4$) and concentrated to give the product (0.9 g, 71%).

6.0.1.134 3,7-Dibromo-1-n-butylphenothiazin-5-ium bromide 1-n-Butyl-10H-phenothiazine (400 mg, 1.6 mmol) was dissolved in glacial acetic acid (20 mL) and a solution of bromine (1.7 mL, 33.2 mmol) also in acetic acid (17 mL) was added to it all at once with vigorous stirring; stirring was continued for about 1 min to 2 min, then water (50 mL) was added to the mixture; the red precipitate was filtered, washed with $Et_2O$, dried under vacuum to afford product (0.75 g, 96%).

6.0.1.135 3,7-Di(4-methylpiperazin-1-yl)-1-n-butylphenothiazin-5-ium bromide

To the stirred solution of 3,7-dibromo-1-n-butylphenothiazin-5-ium bromide (200 mg, 0.41 mmol) in chloroform (10 mL) kept under argon 1-methylpiperazine (205 mg, 2.1 mmol) in chloroform (10 mL) was added all at once with vigorous stirring at room temperature. The resulting mixture was stirred at room temperature for 3 h and concentrated to dryness. The crude product was purified by flash chromatography (methanol-chloroform as an eluent) to provide the title compound.

3,7-Di(4-methylpiperazin-1-yl)-1-methylphenothiazin-5-ium bromide 6.0.1.136 1-Methyl-10H-phenothiazine To a solution of 2-chlorophenothiazine (4.67 g, 20 mmol) in anhydrous ethyl ether (60 mL) methyllithium (1.6 m solution, 62.5 mL, 0.1 mole) was added at room temperature (1 h). After that the mixture had been stirred (6 h), ice-water was added slowly, the stirring was continued for 30 min. The organic layer was separated and combined with ether extracts of the aqueous phase. The combined organic phase was washed with water, dried ($Na_2SO_4$) and concentrated to give the crude product (37% yield). Compound was purified by flash chromatography.

6.0.1.137 1-Methyl-3,7-dibromophenothiazinium bromide

1-Methyl-10H-phenothiazine (0.9 g, 0.004 mole) was dissolved in oxygen-free acetic acid (40 mL) and a solution of bromine also in acetic acid (4.3 mL $Br_2$ in 40 mL AcOH) was added to it all at once with vigorous stirring. Stirring was continued for about 1 min to 2 min., after that water (100 mL) was added to mixture, dark red precipitate was filtered off, washed with ether, dried under vacuum (95% yield).

6.0.1.138 3,7-Di(4-methylpiperazin-1-yl)-1-methylphenothiazin-5-ium bromide

To a solution of 1-methyl-3,7-dibromophenothiazinium bromide (300 mg, 0.7 mmol) in chloroform (15 mL) kept under argon, 1-methylpiperazine (350 mg, 3.5 mmol) was added (30 min) with vigorous stirring. The mixture was stirred for 3 h and after that extracted once with aqueous HBr (10 mL, 1% v/v) and twice with water. The organic layer was dried ($Na_2SO_4$), concentrated and dried under vacuum. Compound was purified by flash chromatography (solvent system—dichloromethane-methanol).

3,7-Di(4-methylpiperazin-1-yl)-1-t-butylphenothiazin-5-ium bromide 6.0.1.139 1-t-Butyl-10H-phenothiazine To a solution of 2-chlorophenothiazine (7.9 g, 34 mmol) in anhydrous THF (100 mL) t-butyllithium (1.7 m solution, 100 mL, 170 mmol) was added at −70° C. (1 h). The reaction mixture had been stirred (2 h), ice-water was added slowly (30 min.) and after that the stirring was continued for 30 min. The organic layer was separated and combined with ether extracts of the aqueous phase. The combined organic phase was washed with water, dried ($Na_2SO_4$) and concentrated to give the crude product (68% yield). Compound was purified by flash chromatography (solvent system-hexane-ethylacetate).

6.0.1.140 1-t-Butyl-3,7-dibromophenothiazinium bromide 1-t-Butyl-10H-phenothiazine (1.2 g, 4.7 mmol) was dissolved in oxygen-free acetic acid (40 mL) and a solution of bromine also in acetic acid (4.9 mL $Br_2$ in 40 mL AcOH) was added to it all at once with vigorous stirring. Stirring was continued for about 1 min to 2 min, after that water (100 mL) was added to mixture, dark red precipitate was filtered off, washed with ether, dried under vacuum (90% yield).

6.0.1.141 3,7-Di(4-methylpiperazin-1-yl)-1-t-butylphenothiazin-5-ium bromide

To a solution of 1-t-butyl-3,7-dibromophenothiazinium bromide (400 mg, 0.8 mmol) in chloroform (15 mL) kept under argon, 1-methylpiperazine (400 mg, 4.0 mmol) was added (30 min) with vigorous stirring. The mixture was stirred for 3 h and after that extracted once with aqueous HBr (10 mL, 1% v/v) and twice with water. The organic layer was dried ($Na_2SO_4$), concentrated and dried under vacuum. Compound was purified by flash chromatography (solvent system: dichloromethane-methanol).

3,7-Di(4-methylpiperazin-1-yl)-1-methylphenothiazin-5-ium bromide 6.0.1.142 1-i-Propyl-10H-phenothiazine To a solution of 2-chlorophenothiazine (4.67 g, 20 mmol) in anhydrous THF (40 mL) i-propyllithium (0.7 m solution in pentane, 100 mL, 70 mmol) was added at −75° C. (1 h). The reaction mixture had been stirred (2 h), ice-water was added slowly (30 min.) and after that the stirring was continued for 30 min. The organic layer was separated and combined with ether extracts of the aqueous phase. The combined organic phase was washed with water, dried ($Na_2SO_4$) and concentrated to give the crude product (52% yield). Compound was purified by flash chromatography (solvent system: hexane-ethyl acetate).

6.0.1.143 1-i-Propyl-3,7-dibromophenothiazinium bromide 1-i-Propyl-10H-phenothiazine (700 mg, 2.9 mmol) was dissolved in oxygen-free acetic acid (30 mL) and a solution of bromine also in acetic acid (3 mL $Br_2$ in 30 mL AcOH) was added to it all at once with vigorous stirring. Stirring was continued for about 1-2 min., after that water (100 mL) was added to mixture, dark red precipitate was filtered off, washed with ether, dried under vacuum (90% yield).

6.0.1.144 3,7-Di(4-methylpiperazin-1-yl)-1-i-propylphenothiazin-5-ium bromide

To a solution of 1-i-propyl-3,7-dibromophenothiazinium bromide (200 mg, 0.42 mmol) in chloroform (10 mL) kept under argon, 1-methylpiperazine (290 mg, 2.9 mmol) was added (30 min) with vigorous stirring. The mixture was stirred for 3 h and after that extracted once with aqueous HBr (10 mL, 1% v/v) and twice with water. The organic layer was dried ($Na_2SO_4$), concentrated and dried under vacuum. Compound was purified by flash chromatography (solvent system: dichloromethane-methanol).

1,9-Dimethylphenothiazinium-5-ium derivatives 6.0.1.145 3-(4-Acetylpiperazin-1-yl)-7-(methyl(n-butyl)amino)-1,9-dimethylphenothiazin-5-ium iodide To a solution of 3-(4-acetylpiperazin-1-yl)-1,9-dimethylphenothiazin-5-ium triiodide (73 mg, 0.1 mmol) in methanol (5 mL) methyl(n-butyl)amine (0.034 mL, 25.2 mg, 0.3 mmol) was added. Reaction mixture was stirred for 24 h at room temperature. The resulting mixture was concentrated to dryness and purified by flash chromatography using the methanol-chloroform gradient to provide the title compound.

6.0.1.146 3,7-di(4-Acetylpiperazin-1-yl)-1,9-dimethylphenothiazin-5-ium iodide

A solution of 3-(4-acetylpiperazin-1-yl)-1,9-dimethylphenothiazin-5-ium triiodide (73 mg, 0.1 mmol) in methanol (5 mL) and 1-acetylpiperazine (38.5 mg, 0.3 mmol) was stirred for 24 h at room temperature. The resulting mixture was concentrated to dryness and purified by flash chromatography using the methanol-chloroform gradient to provide the title compound.

6.0.1.147 3-(4-Boc-piperazin-1-yl)-7-(methyl(n-butyl)amino)-1,9-dimethylphenothiazin-5-ium iodide To a solution of 3-(4-Boc-piperazin-1-yl)-1,9-dimethylphenothiazin-5-ium triiodide (158 mg, 0.2 mmol) in methanol (5 mL) methyl(n-butyl)amine (0.065 mL, 25.2 mg, 0.6 mmol) was added. Reaction mixture was stirred for 24 h at room temperature. The resulting mixture was concentrated to dryness and purified by flash chromatography using the methanol-chloroform gradient to provide the title compound.

6.0.1.148 3-(piperazin-1-yl)-7-(methyl(n-butyl)amino)-1,9-dimethylphenothiazin-5-ium trifluoroacetate A solution of 3-(4-Boc-piperazin-1-yl)-7-(methyl(n-butyl)amino)-1,9-dimethylphenothiazin-5-ium iodide (25 mg) in dichloromethane (5 mL) and trifluoroacetic acid (2 mL) was stirred for 4 h at room temperature. The resulting mixture was concentrated to dryness, rinsed out by toluene (3×10 mL) and dried under vacuum to provide the title compound.

1-Ethyl-9-methylphenothiazinium-5-ium derivatives

1-Ethyl-9-methylphenothiazin-5-ium tetraiodide hydrate 6.0.1.149 N-Acetyl-2-ethylaniline Commercial 2-ethylaniline (50 mL, 0.40 mol) was dissolved in acetic anhydride (160 mL, 1.70 mol) and stirred at room temperature for 2 h. Then the reaction mixture was poured into $H_2O$, the whole was extracted with ethyl acetate (2×200 mL). The combined organic extracts were washed with 5% aqueous $NaHCO_3$, brine, dried ($K_2CO_3$), filtered and concentrated to provide the title compound as a white solid (60.0 g, 92%).

6.0.1.150 N-Acetyl-2-ethyl-2'-methyldiphenylamine

A mixture of the N-acetyl-2-ethylaniline (35.0 g, 215 mmol), anhydrous $Cs_2CO_3$ (70.0 g, 215 mmol), CuBr (2.86 g, 20 mmol), KI (3.33 g, 20 mmol) and 2-bromotoluene (78 mL, 640 mmol) was stirred and heated at 175° C. to 180° C. under an argon atmosphere for 48 h. After cooling the reaction mixture was poured into ice-$H_2O$ and extracted with ethyl acetate (2×200 mL), the combined organic extracts were washed with brine, dried over anhydrous $K_2CO_3$, filtered and concentrated to dryness. The obtained crude material was purified by flash chromatography (using ethyl acetate-hexane as an eluent) to afford the N-acetyl-2-ethyl-2'-methyldiphenylamine (35.4 g, 65%).

6.0.1.151 2-Ethyl-2'-methyldiphenylamine a solution of the N-acetyl-2-ethyl-2'-methyldiphenylamine (32.5 g, 128 mmol) in 10% KOH (72 g, 1.28 mol)/EtOH (120 mL) was stirred and refluxed for 6 h, then poured into $H_2O$. The mixture was extracted with ethyl acetate (2×100 mL). The combined organic layers were washed with brine, dried ($Na_2SO_4$), filtered and concentrated to dryness, gave dark red oil (21.1 g, 78%).

6.0.1.152 1-Ethyl-9-methyl-10H-phenothiazine to a 2-ethyl-2'-methyldiphenylamine (3.0 g, 14.2 mmol), sulfur (909 mg, 28.4 mmol) and iodine (601 mg, 4.7 mmol) were added. Vial was charged with balloon for discharge. The heating block was preheated (150° C.). The vial was heated on the heating block and after 15 min. Temperature was increased to 210° C., reaction mixture was stirred and heated for an additional 1 h. The mixture was allowed to cool to 90° C. The dark solid material was dissolved in mixture methanol/chloroform and purified by flash chromatography (ethyl acetate-hexane as an eluent) to afford the desired product (790 mg, 23%).

6.0.1.153 1-Ethyl-9-methylphenothiazin-5-ium tetraiodide hydrate a solution of 1-ethyl-9-methyl-10H-phenothiazine (4.83 g, 20 mmol) in anhydrous chloroform (50 mL) was stirred at 5° C. and the solution of iodine (15.25 g, 60 mmol) in $CHCl_3$ (300 mL) was added drop wise over 3 h. The resulting dark solution was stirred for an additional 3 h at 5° C., monitored by TLC. After the disappearance of the starting material, the resulting precipitate was filtered, washed with a copious amount of chloroform, dried overnight in vacuum to afford a dark solid (9.18 g, 60%).

6.0.1.154 3,7-(Di(4-methylpiperazin-1-yl)-1-ethyl-9-methylphenothiazin-5-ium iodide A solution of 1-ethyl-9-methylphenothiazin-5-ium tetraiodide hydrate (50 mg, 0.07 mmol) in methanol (10 mL) and 1-methylpiperazine (30 mg, 0.3 mmol) was stirred for 2 h at room temperature. The resulting mixture was concentrated to dryness and purified by flash chromatography using the methanol-chloroform gradient to provide the title compound.

3-(Dimethylamino)-9-ethyl-1-methyl-7-(4-methylpiperazin-1-yl)phenothiazin-5-ium iodide 6.0.1.155 3-(Dimethylamino)-1-ethyl-9-methylphenothiazin-5-ium triiodide To the stirred mixture of 9-ethyl-1-methylphenothiazin-5-ium tetraiodide hydrate (383 mg, 0.5 mmol) in anhydrous $CHCl_3$ (20 mL) dimethylamine (0.5 mL, 1.0 mmol, 2 M solution in THF) was added drop wise over 4 h. The resulting mixture was stirred at room temperature overnight, concentrated to dryness.

6.0.1.156 3-(Dimethylamino)-1-ethyl-9-methyl-7-(4-methylpiperazin-1-yl)-phenothiazin-5-ium iodide a solution of 3-(dimethylamino)-1-ethyl-9-methylphenothiazin-5-ium triiodide (137 mg, 0.21 mmol) in methanol (10 mL) and 1-methylpiperazine (30 mg, 0.3 mmol) was stirred for 2 h at room temperature. The resulting mixture was concentrated to dryness and purified by flash chromatography using the methanol-chloroform gradient to provide the title compound.

6.0.1.157 3-(Dimethylamino)-1-ethyl-9-methyl-7-(4-(trifluoromethylsulfonyl)piperazin-1-yl)phenothiazin-5-ium iodide To a solution of 3-(dimethylamino)-1-ethyl-9-methylphenothiazin-5-ium triiodide (100 mg, 0.15 mmol) in methanol (10 mL), 4-(trifluoromethylsulfonyl)piperazin-1-ium hydrochloride (115 mg, 0.45 mmol) and triethylamine (0.15 mL, μmol) was stirred for 2 h at room temperature. The resulting mixture was concentrated to dryness and purified by flash chromatography using the methanol-chloroform gradient to provide the title compound.

6.0.1.158 3-(4-(Cyclopropylsulfonyl)piperazin-1-yl)-7-(dimethylamino)-9-ethyl-1-methyl-phenothiazin-5-ium iodide To a solution of 3-(dimethylamino)-1-ethyl-9-methylphenothiazin-5-ium triiodide (200 mg, 0.30 mmol) in acetonitrile (10 mL), 4-(cyclopropylsulfonyl)piperazin-1-ium hydrochloride (114 mg, 0.5 mmol) and triethylamine (0.15 mL, 1 mmol) was stirred for 4 h at room temperature. The resulting mixture was concentrated to dryness and purified by flash chromatography using the methanol-chloroform gradient to provide the title compound.

3-(Bis(2-methoxyethyl)amino)-1-ethyl-9-methyl-7-(4-methylpiperazin-1-yl)-phenothiazin-5-ium iodide 6.0.1.159 3-(Bis(2-methoxyethyl)amino)-1-ethyl-9-methylphenothiazin-5-ium triiodide To the stirred mixture of 9-ethyl-1-methylphenothiazin-5-ium tetraiodide hydrate (383 mg, 0.5 mmol) in anhydrous $CHCl_3$ (20 mL) bis(2-methoxyethyl)amine (133 mg, 1.0 mmol was added drop wise over 4 h. The resulting mixture was stirred at room temperature overnight and concentrated to dryness.

6.0.1.160 3-(Bis(2-methoxyethyl)amino)-1-ethyl-9-methyl-7-(4-methylpiperazin-1-yl)phenothiazin-5-ium iodide A solution of 3-(bis(2-methoxyethyl)amino)-9-ethyl-1-methylphenothiazin-5-ium triiodide (150 mg, 0.2 mmol) in methanol (10 mL) and 1-methylpiperazine (30 mg, 0.3 mmol) was stirred for 2 h at room temperature. The resulting mixture was concentrated to dryness and purified by flash chromatography using the methanol-chloroform gradient to provide the title compound.

1-Ethyl-9-methyl-)-7-(4-(methylsulfonyl)-1,4-diazepan-1-yl)-3-(pyrrolidin-1-yl)phenothiazin-5-ium iodide 6.0.1.161 1-Ethyl-9-methyl-3-(pyrrolidin-1-yl)phenothiazin-5-ium triiodide To the stirred mixture of 9-ethyl-1-methylphenothiazin-5-ium tetraiodide hydrate (383 mg, 0.5 mmol) in anhydrous $CHCl_3$ (20 mL) pyrrolidine (71 mg, 1.0 mmol) was added drop wise over 4 h. The resulting mixture was stirred at room temperature overnight and concentrated to dryness.

6.0.1.162 1-Ethyl-9-methyl-7-(4-methylsulfonyl)-1,4-diazepan-1-yl)-3-(pyrrolidin-1-yl)-phenothiazin-5-ium iodide A solution of 3-(pyrrolidin-1-yl)-1-ethyl-9-methylphenothiazin-5-ium triiodide (160 mg, 0.23 mmol) in methanol (10 mL), 4-(methylsulfonyl)-1,4-diazepan-1-ium hydrochloride (150 mg, 0.7 mmol) and triethylamine (0.15 mL, 1 mmol) was stirred for 4 h at room temperature. The resulting mixture was concentrated to dryness and purified by flash chromatography using the methanol-chloroform gradient to provide the title compound.

6.0.1.163 3-(4-(cyclopropylsulfonyl)piperazin-1-yl)-9-ethyl-1-methyl-7-(pyrrolidin-1-yl)-phenothiazin-5-ium iodide To a solution of 3-(pyrrolidin-1-yl)-1-ethyl-9-methylphenothiazin-5-ium triiodide (150 mg, 0.20 mmol) in acetonitrile (10 mL), 4-(cyclopropylsulfonyl)piperazin-1-ium hydrochloride (91 mg, 0.4 mmol) and triethylamine (40 mg, 0.4 mmol) was stirred for 4 h at room temperature. The resulting mixture was concentrated to dryness and purified by flash chromatography using the methanol-chloroform gradient to provide the title compound.

3,7-Bis(4-Boc-1,4-diazepan-1-yl)-1-ethyl-9-methylphenothiazin-5-ium iodide 6.0.1.164 3-(4-Boc-1,4-diazepan-1-yl)-1-ethyl-9-methyl-phenothiazin-5-ium triiodide to the stirred mixture of 9-ethyl-1-methylphenothiazin-5-ium tetraiodide hydrate (153 mg, 0.2 mmol) in anhydrous $CHCl_3$ (10 mL) 1-Boc-1,4-homopiperazine (60 mg, 0.3 mmol) was added drop wise over 2 h. The resulting mixture was stirred at room temperature overnight, concentrated to dryness.

6.0.1.165 3,7-Bis(4-Boc-1,4-diazepan-1-yl)-1-ethyl-9-methyl-phenothiazin-5-ium iodide A solution of 3-(4-Boc-1,4-diazepan-1-yl)-1-ethyl-9-methyl-phenothiazin-5-ium triiodide (100 mg, 0.12 mmol) in methanol (10 mL) and 4-Boc-1,4-diazepane (100 mg, 0.5 mmol) was stirred for 4 h at room temperature. The resulting mixture was concentrated to dryness and purified by flash chromatography using the methanol-chloroform gradient to provide the title compound.

3-(4-Boc-1,4-diazepan-1-yl)-1-ethyl-9-methyl-7-(pyrrolidin-1-yl)-phenothiazin-5-ium iodide 6.0.1.166 3-(4-Boc-1,4-diazepan-1-yl)-1-ethyl-9-methyl-7-(pyrrolidin-1-yl)-phenothiazin-5-ium iodide a solution of 3-(4-Boc-1,4-diazepan-1-yl)-1-ethyl-9-methyl-phenothiazin-5-ium triiodide (100 mg, 0.12 mmol) in methanol (10 mL) and pyrrolidine (71 mg, 1.0 mmol) was stirred for 4 h at room temperature. The resulting mixture was concentrated to dryness and purified by flash chromatography using the methanol-chloroform gradient to provide the title compound.

3,7-di(1,4-Diazepan-1-yl)-1-ethyl-9-methyl-phenothiazin-5-ium trifluoroacetate 6.0.1.167 3,7-di(1,4-Diazepan-1-yl)-1-ethyl-9-methyl-phenothiazin-5-ium iodide a solution of 3,7-bis(4-Boc-1,4-diazepan-1-yl)-1-ethyl-9-methyl-phenothiazin-5-ium iodide (75 mg, 0.01 mmol) in dichloromethane (10 mL) and trifluoroacetic acid (1.0 mL) was stirred for 3 h at 50° C. The resulting mixture was washed by toluene (2×5 mL), pentane (2×5 mL) and concentrated to dryness.

3-(1,4-diazepan-1-yl)-1-ethyl-9-methyl-7-(pyrrolidin-1-yl)-phenothiazin-5-ium trifluoroacetate 6.0.1.168 3-(1,4-Diazepan-1-yl)-1-ethyl-9-methyl-7-(pyrrolidin-1-yl)-phenothiazin-5-ium iodide A solution of 3-(4-Boc-1,4-diazepan-1-yl)-1-ethyl-9-methyl-7-(pyrrolidin-1-yl)-phenothiazin-5-ium iodide (65 mg, 0.01 mmol) in dichloromethane (10 mL) and trifluoroacetic acid (1.0 mL) was stirred for 3 h at 50° C. The resulting mixture was washed by toluene (2×5 mL), pentane (2×5 mL) and concentrated to dryness.

3-(4-Boc-piperazin-1-yl)-1-ethyl-9-methyl-7-morpholino-phenothiazin-5-ium iodide 6.0.1.169 3-(4-Boc-piperazin-1-yl)-1-ethyl-9-methyl-phenothiazin-5-ium triiodide to the stirred mixture of 9-ethyl-1-methylphenothiazin-5-ium tetraiodide hydrate (383 mg, 0.5 mmol) in anhydrous $CHCl_3$ (20 mL) 1-Boc-piperazine (93 mg, 0.5 mmol) was added drop wise over 4 h. The resulting mixture was stirred at room temperature overnight, concentrated to dryness.

6.0.1.170 3-(4-Boc-piperazin-1-yl)-1-ethyl-9-methyl-7-morpholino-phenothiazin-5-ium iodide a solution of 3(4Bocpiperazin1yl)1ethyl9-methylphenothiazin5ium triiodide (403 mg, 0.5 mmol) in acetonitrile (10 mL) and morpholine (70 mg, 0.8 mmol) was stirred for 4 h at 50° C. The resulting mixture was concentrated to dryness and purified by flash chromatography using the methanol-chloroform gradient to provide the title compound.

1-Ethyl-9-methyl-7-morpholino-3-(piperazin-1-yl)-phenothiazin-5-ium trifluoroacetate 6.0.1.171 1-Ethyl-9-methyl-7-morpholino-3-(piperazin-1-yl)-phenothiazin-5-ium trifluoroacetate a solution of 3-(4-Boc-piperazin-1-yl)-1-ethyl-9-methyl-7-morpholino-phenothiazin-5-ium iodide (65 mg, 0.01 mmol) in dichloromethane (10 mL) and trifluoroacetic acid (1.0 mL) was stirred for 1 h at 50° C. The resulting mixture was washed by toluene (2×5 mL), pentane (2×5 mL) and concentrated to dryness.

6.0.2 Biological Activity of Compounds 6.0.2.1 Respiratory Viruses

The activities of compounds of the invention were determined for the following viruses using the protocol below:

Corona Virus on MRC5 Cells
Influenza Virus A on MDCK Cells
Respiratory Syncytial Virus on HEp2 cells
Adenovirus serotype 5 on A549 cells
Human Rhinovirus on H1Hela Cells
Herpes Simplex Virus 1 on Vero cells Virus was grown in the presence of four dilutions (10 μM, 2 μM, 0.4 μM and 0.08 μM) of the chemical compound tested with two controls using standard methods and materials for the relevant virus. The infected cell extract was collected using known methods, and the infectious virus concentration was determined using standard techniques.

Each well was titrated by $TCID_{50}$. Four serial dilutions in quadruplicate required to determine the titer of each well. To assay 36 replicates as directed, one hundred eight (108) 96-well plates will be required. Each drug was tested at four dilutions against one virus will require $TCID_{50}$ titers of 18 sample wells.

6.0.2.2 Monkey Pox Virus

Compounds of the invention were tested for activity against monkey pox virus using the following protocol:

1. Infected cells with target dose of 100 PFU/well MPXV.
2. One hour later, removed the virus solution and wash cells with media and aspirated.
3. Added serial half-log dilutions of compounds in methyl cellulose to triplicate wells; methyl cellulose is semi-solid media which contains virus in one location, so only the adjacent cells are infected. Each plate included a positive control of virus only wells (triplicate), with methyl cellulose overlay.
4. Four days later, removed the media from wells and added crystal violet to stain the cells.

5. After 20 min to 30 min later, washed the cells with $ddH_2O$ and dried.
6. Counted the plaques.
7. Compared plaque numbers of compound wells with the plaque numbers in virus only wells and determined the difference (percentage) of inhibition vs. protection.

6.0.2.3 Marburg Virus

Compounds of the invention were tested against Marburg virus using the following protocol:

Dimethylsulfoxide (DMSO) in 5 mM concentration was used as a solvent for the compounds and as a control. The compounds tested were stored under argon. Each compound was provided in a vial. The experiments were performed on 24-well plate.

Incubation of Compounds With Cells.

Day 0: Plated Vero cells at $1\times10^5$ cells/well in a 1 mL volume of medium (24-well plate), and incubated overnight.

Day 1:

1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and added 1 mL of compound or control to the appropriate wells.
4. Incubated plate overnight.

Day 2:

1. Dilute virus: Diluted MARV to a concentration of $1\times10^6$ pfu/mL EMEM with 10% FBS/Pen/Strep.
2. Infection: Removed media from wells and applied 100 μL diluted virus to each well, except mock-infected well. Applied 100 μL EMEM with 10% FBS to the mock-infected well. Incubated the plate for 1 h at 37° C., rocking the plate gently every 15 min to prevent the cell monolayer from drying out.
3. Wash cells and add compound: After the one-hour infection period, aspirated the virus from the wells and add 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
5. Incubated the plates at 37° C. under 5% $CO_2$ for 72 h.

Day 3: Removed as much media as possible from each well and stored at −80° C.

Determination of Plaques.

Day 0: Seeded 6-well plates with $2.5\times10^5$ Vero cells/well in 2 mL volumes of medium. Incubated overnight.

Day 1:

1. In deep-well 96-well plates prepared six 1:10 serial dilutions of supernatants from each well beginning with 1:10 and ending with 1:6 in 500 μL volumes EMEM with 2% FBS:
   (a) Diluted 60 μL undiluted supe into 540 μL EMEM with 2% FBS=1:1.
   (b) Diluted 60 μL of the 1:1 supe into 540 μL EMEM with 2% FBS=1:2.
   (c) Diluted 60 μL of the 1:2 supe into 540 μL EMEM with 2% FBS=1:3.
   (d) Diluted 60 μL of the 1:3 supe into 540 μL EMEM with 2% FBS=1:4
   (e) Diluted 60 μL of the 1:4 supe into 540 μL EMEM with 2% FBS=1:5
   (f) Diluted 60 μL of the 1:5 supe into 540 μL EMEM with 2% FBS=1:6
2. Prepared 2% agarose and place in a 37° C. water bath to prevent the solution from solidifying. Prewarm 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and add 200 μL of diluted culture supernatant in duplicate to appropriate wells, according to plate diagram.
4. Incubated each plate for 1 h at 37° C. under 5% $CO_2$, rocking the plate gently every 15 minute.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.
7. Incubated the plates for 5 d at 37° C. under 5% $CO_2$.
8. Stained the cells using a secondary overlay containing neutral red and incubate for 24 h.
9. Quantified the plaques in each well.

6.0.2.4 Influenza Virus

Compounds of the invention were tested for activity against Influenza virus using the following protocol:

1. MDCK (Madin-Darby canine kidney) cells were plated in three 96-well plates ($6\times10^4$ per well) and cultured overnight. The next day the cells were inspected with a microscope to document the confluence. The required amount of wells were infected with the fowl plaque virus (Influenza A/H7N7/Bratislava/1979) with an MOI of 1 (assuming duplication of cells over night to generate $1.2\times10^5$ PFU/well). Infection was performed with 200 μL of virus suspension. All three plates were treated identically and served as triplicates. On each plate was one well with one concentration of substance, three wells with the highest concentration of DMSO that is used on the plate, and three wells with the lowest concentration of DMSO that is on the plate. In addition there were three infected wells that were cultured with cell culture medium without additional substance. There also were 12 wells on every plate that were not infected and served as controls for the cpe determination and for the neutral red staining.
2. Substances were diluted before cells were infected and plates in 96-well plates so that they could easily be plated on the infected cells.
3. Infection was performed for 30 min at 37° C. in a cell culture incubator.
4. After infection the cells were washed once with infection-PBS. During washing the cell monolayer was inspected with a microscope, and damaged monolayers were excluded from testing. Uninfected wells were mock infected with infection-PBS and also inspected visually.
5. The pattern of substances on every individual plate was marked on the top of the plate and on a scheme.

6. An aliquot of 250 μL of diluted substance was used and cells were incubated for 16 h. After incubation time the cell monolayer was again inspected and cpe was monitored and recorded.
7. Supernatants of the first plate were transferred to a 96-well ELISA-plate and kept cool for titration, which was performed later the same day.
8. Cells of this plate were washed carefully with PBS again inspected at the microscope and then stained with neutral red (which is staining the living cells) for 3 hours at 37° C. (neutral red is used at the concentration 1 mg/20 mL MEM; 200 μL/well.
9. In the meantime the dilutions for the titration were generated in a 96-well plate by diluting the supernatants 1:10. A 100 μL aliquot of undiluted supernatant and five dilutions (from $10^{-1}$ to $10^{-5}$ were used to infect 24-wells of MDCK monolayers of cells. This means that at this time point we only titrate one unique copy of every tested substance. The other three plates were immediately frozen at −70° C. and stored until titration.
10. The neutral red staining was stopped by washing the monolayer three times very carefully with PBS and the plate was dried on cellulose to eliminate residual PBS.
11. The neutral red was dissolved from the cells by using Ethanol/acidic acid for 15 min on a plate rocking platform.
12. The Ethanol/acidic acid was transferred to an Elisa-plate and measured at 570 nm in an Elisa-reader.
13. The percentage of live cells was calculated setting the non-infected cells to 100%.

6.0.2.5 Ebola Virus

Compounds of the invention were tested for activity against Ebola virus using the following protocol:

Concentration of Compound: 10 mm DMSO stock. Day 0:

Vero cells were plated at $1\times10^5$ cells/well in a 1 mL volume of medium (24-well plate), and incubate overnight.

Day 1: Compound Dilutions

1. Following sterile procedure, diluted each of the four compound stocks in DMSO to concentrations 100-fold greater than will be used in the treatment wells.
2. Further diluted the DMSO stocks 1:100 in EMEM with 10% FBS/Pen/Strep to generate treatments containing 1% DMSO. To generate DMSO control media, diluted DMSO (no compound) to 1% in EMEM with 10% FBS/Pen/Strep.
3. Aspirated the media in cell plates and add 1 mL of compound or control to the appropriate wells.
4. Incubated plate overnight.

Day 2:

1. Diluted virus: Diluted EBOV to a concentration of $1\times10^6$ PFU/mL Eagle's Minimum Essential Medium (EMEM) with 10% FBS/Pen/Strep.
2. Infection: Removed media from wells and applied 100 μL diluted virus to each well, except mock-infected well. Applied 100 μL) EMEM with 10% FBS to the mock-infected well. Incubated the plate 1 h at 37° C., rocking the plate gently every 15 min to prevent the cell monolayer from drying out.
3. Washed cells and added compound. After the 1 h infection period, aspirated the virus from the wells and added 1 mL PBS to each well. Aspirated the PBS and immediately added 1 mL diluted compound to the appropriate wells. The DMSO control and mock-infected wells received 1 mL of the DMSO control media.
4. Critical Treatments:
   (a) Compound Treatment Wells
   (b) DMSO control media+virus
   (c) DMSO control media no virus (Mock)
5. Incubated the plates: Incubated the plates at 37° C. under 5% $CO_2$ for 72 h.

Day 3:

Removed the supernatant from infected plates: Removed as much media as possible from each well and stored at −80° C.

Plaque Assay:

Day 0:

1. Seeded 6-well plates with $2.5\times10^5$ Vero cells/well in 2 mL volumes of medium. Incubated overnight.

Day 1:

1. In deep-well 96-well plates prepared six 1:10 serial dilutions of supernatants from each well beginning with 1:10 and ending with 1:$10^6$ in 500 μL volumes of EMEM with 2% FBS:
   (a) Diluted 60 μL undiluted supe into 540 μL EMEM with 2% FBS=1:10'.
   (b) Diluted 60 μL of the 1:$10^1$ supe into 540 μL EMEM with 2% FBS=1:$10^2$.
   (c) Diluted 60 μL of the 1:$10^2$ supe into 540 μL EMEM with 2% FBS=1:$10^3$.
   (d) Diluted 60 μL of the 1:$10^3$ supe into 540 μL EMEM with 2% FBS=1:$10^4$
   (e) Diluted 60 μL of the 1:$10^4$ supe into 540 μL EMEM with 2% FBS=1:$10^5$
   (f) Diluted 60 μL of the 1:$10^5$ supe into 540 μL EMEM with 2% FBS=1:$10^6$
2. Prepared 2% agarose and placed in a 37° C. water bath to prevent the solution from solidifying. Prewarmed 2×EMEM in a 37° C. water bath.
   (a) Volume of agarose needed=12 mL per undiluted supe sample+extra.
   (b) Volume of 2×EMEM needed is the same.
3. Removed culture supernatant from plated cells and added 200 μL of diluted culture supernatant in duplicate to appropriate wells, according to plate diagram.
4. Incubated each plate for 1 h at 37° C. under 5% $CO_2$, rocking the plate gently every 15 min.
5. After plates had incubated for 1 h, combined the 2% agarose with the 2×EMEM and mixed well. Gently applied 2 mL overlay to each well without removing the inoculum and swirled the plate gently to mix the inoculum in with the overlay. Repeated this process to apply overlays to each plate.
6. Allowed the overlays to solidify at room temperature for 1 h.
7. Incubated the plates for 5 d at 37° C. under 5% $CO_2$.
8. Stained the cells using a secondary overlay containing neutral red and incubated for 24 h.
9. Quantified the plaques in each well.

6.0.2.6 Dengue, Easter Equine Encephalitis, Venezuelan Equine Encephalitis, Western Equine Encephalitis, West Nile, and Chikungunya Viruses Compounds of the invention were tested for activity against Dengue, Easter Equine Encephalitis, Venezuelan Equine Encephalitis, Western Equine Encephalitis, West Nile, and Chikungunya Viruses using the following protocol:

1. The Set test sample was set up in ten-fold dilutions across a 96-well plate. A mixture of 270 μL HBSS with HEPES and 2% FBS with Pen/Strep or complete media 2% FBS was added to each well. To the first well in each row 30 μL of test sample was introduced (i.e, a 1:10 dilution) and mixed. A 30 μL aliquot was transferred from the first well to next well, and so on. Dilutions out to well #9 were made to provide a range of dilutions from $10^{-1}$ to $10^{-9}$. Be sure to discard tips between transfers.

2. Once dilutions were ready the plates were labeled with sample number and dilutions (plates can be labeled at any time prior to infection). Each dilution was plated on two wells. If plating dilutions $10^{-1}$ to $10^{-9}$, requires three plates per sample.
3. The media was removed from six-well plates by inverting over a dishpan containing microchem disinfectant. Then 100 μL was added to each well of virus dilution. A duplicate was done to obtain an average. The plates were incubated at 37° C., 5% $CO_2$ for 1 h with occasional rocking (approximately every 15 min).
4. Preparation of media and agarose for overlay. Final concentration 1×EMEM, 10% FBS, 1% Pen/Strep, 0.1% gentamycin, in a 0.6% agarose solution (see cell culture overlay without neutral red chart). Added about 2 mL of overlay to each well and returned to the incubator. (It is not necessary to allow to solidify prior to placing in the incubator.) Incubated overnight at 37° C., 5% $CO_2$.
5. Next day: The resulting plaques were visualized with Neutral Red. A media/agarose overlay was prepared as above with 4% neutral red solution added to the media/agarose overlay as prepared in Step 4 (see cell culture overlay with neutral red overlay chart). Added about 2 mL ml per well.
6. Incubated the plates overnight at 37° C., 5% $CO_2$.
7. Counted plaques.

The results of the above-described assays for some compounds of the invention are provided in the FIGURE. As will be appreciated by those having ordinary skill in the art, the compounds of the invention display surprisingly strong antiviral properties across a startlingly wide range of viruses, especially viruses associated respiratory diseases including, but not limited to, bronchiolitis, the common cold, croup, influenza, and pneumonia. In particular, the compound 3-(dimethylamino)-1,9-dimethyl-7-(4-methylpiperazin-1-yl)phenothiazin-5-ium iodide displayed surprisingly strong activity across all of the respiratory viruses tested, demonstrating unprecedented pan-respiratory anti-viral activity. Given that many respiratory diseases are in fact syndromes caused by multiple factors, especially multiple viruses, these results demonstrate that compounds of the invention can be treatments for diseases in which a virus (or multiple viruses) is an etiological component of a respiratory syndrome, in particular a respiratory syndrome selected from the group consisting of: bronchiolitis, the common cold, croup, influenza, and pneumonia.

CONCLUSION

The above description of the embodiments, alternative embodiments, and specific examples, are given by way of illustration and should not be viewed as limiting. Further, many changes and modifications within the scope of the present embodiments may be made without departing from the spirit thereof, and the present invention includes such changes and modifications.

What is claimed:

1. A compound having the structure:

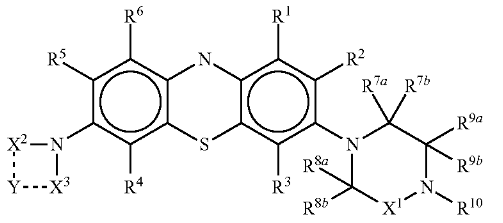

and its pharmaceutically acceptable salts, hydrates, and coordination compounds, wherein:

$R^6$ is halo or optionally substituted alkyl, $R^1$-$R^5$ and $R^{7a}$-$R^{9b}$ are selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl) alkylcarbonylamino, (cycloheteroalkyl) alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsuonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralkyloxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl;

$R^{10}$ is hydrogen or optionally substituted alkyl, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsufonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl;

$X^1$ is $(CR^{11}R^{11'})_m$, wherein m is either 1 or 2 such that each of $R^{11}$ and $R^{11'}$, independently for each value of m, is selected independently from the group consisting of: hydrogen, halo, cyano, nitro, thio, amino, carboxyl, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl) alkylcarbonylamino, (cycloheteroalkyl) alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl Y is optionally present; and when Y is present, Y is $NR^{12}$, O, S, SO, or $SO^2$, or a single or double bond between $X^2$ and $X^3$;

$R^{12}$ is hydrogen or optionally substituted alkyl, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsufonyl, cycloalkylsulfonyl, alkyloxycarbonyl, aryloxycarbonyl, heteroaryloxycarbonyl, cycloalkyloxycarbonyl, cycloheteroalkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl; and $X^2$ and $X^3$ are $(CR^{13}R^{13'})_n$ and $(CR^{14}R^{14'})_o$ respectively, wherein each of n and o is independently either 1, 2, or 3 such that the sum n+o is either 3, 4, or 5, and independently for each value of the n and o methylene units of $X^2$ and $X^3$, each of $R^{13}$, $R^{13'}$, $R^{14}$, and $R^{14'}$ is selected independently from the group consisting of:

hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl) iminoalkyl, and (cycloheteroalkyl)iminoalkyl; and when Y is not present $X^2$ is $R^{15}$ and $X^3$ is $R^{16}$, wherein $R^{15}$ and $R^{16}$ are selected independently from the group consisting of: hydrogen and optionally substituted alkyl, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylsulfonyl, arylsulfonyl, heteroarylsufonyl, cycloalkylsulfonyl, alkyloxycarbonyl, aryloxycarbonyl, heteroaryloxycarbonyl, cycloalkyloxycarbonyl, cycloheter-alkyloxycarbonyl, aralkyloxycarbonyloxycarbonyl, heteroaralkyloxycarbonyl, (cycloalkyl)alkyloxycarbonyl, and (cycloheteroalkyl)alkyloxycarbonyl wherein when said optionally substituted alkyl is substituted, said substitution is with a group which is hydrooxyl, nitro, amino, imino, cyano, halo, thio, thioamido, amidino, oxo, oxamidino, methoxamidino, imidino, guanidino, sulfonamido, carboxyl, formyl, lower alkyl, haloloweralkyl, loweralkoxy, haloloweralkoxy, lower alkoxyalkyl, alkylcarbonyl, arylcarbonyl, aralkylcarbonyl, heteroarylcarbonyl, heteroaralkylcarbonyl, alkylthio, aminoalkyl, or cyanoalkyl.

2. A compound of claim 1, wherein m is 1, such that $X^1$ is $(CR^{11'})$, thereby defining $X^1$ as $(CR^{11a}R^{11b})$, said compound having the structure:

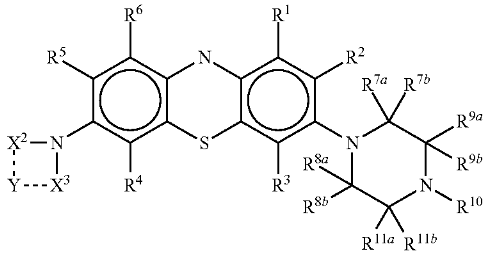

wherein $R^{11a}$ and $R^{11b}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl) alkylcarbonylamino, (cycloheteroalkyl) alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

3. A compound of claim 2, wherein Y is not present, said compound having the structure:

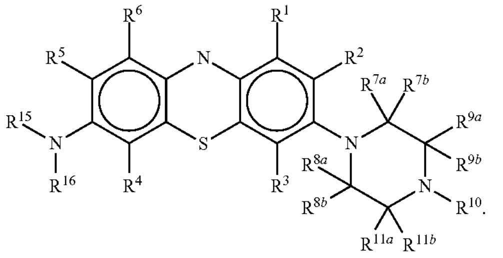

4. A compound of claim 3, wherein each of $R^{15}$ and $R^{16}$ is hydrogen.

5. A compound of claim 4, wherein each of $R^2$-$R^5$, $R^{7a}$-$R^{9b}$, $R^{11a}$, and $R^{11b}$ is hydrogen, each of $R^1$ and $R^6$ independently is optionally substituted alkyl, and $R^{10}$ is optionally substituted alkyl or alkylsulfonyl.

6. A compound of claim 3, wherein each of $R^{15}$ and $R^{16}$ independently is alkyl or alkyloxyalkyl.

7. A compound of claim 6, wherein each of $R^{15}$ and $R^{16}$ independently is alkyl.

8. A compound of claim 7, wherein each of $R^{15}$ and $R^{16}$ independently is methyl or ethyl.

9. A compound of claim 8, wherein each of $R^2$-$R^5$, $R^{7a}$-$R^{9b}$, $R^{11a}$, and $R^{11b}$ is hydrogen, and $R^{10}$ is hydrogen, or optionally substituted alkyl, alkyloxycarbonyl, alkylsulfonyl, cycloalkylsulfonyl, and alkylaminosulfonyl.

10. A compound of claim 2, wherein Y is present, said compound having the structure:

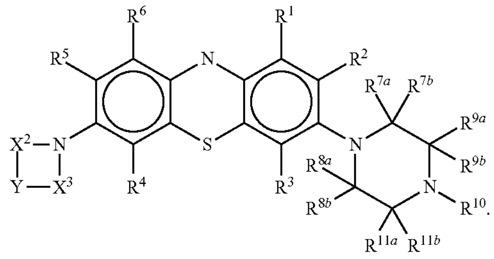

11. A compound of claim 10, wherein each of n and o is 2, such that $X^2$ and $X^3$ have the form $(CR^{13}R^{13'})_2$ and $(CR^{14}R^{14b})_2$ respectively defining thereby $X^2$ as $(CR^{13a}R^{13b})$ $(CR^{13c}R^{13d})$ and $X^3$ as $(CR^{14a}R^{14b})$ $(CR^{14c}R^{14d})$, said compound having the structure:

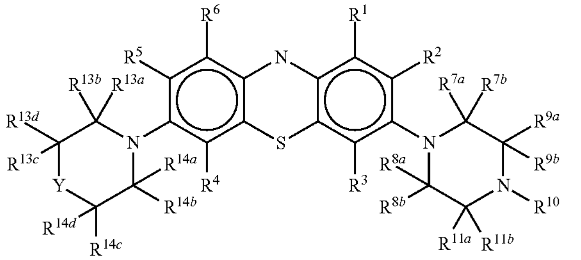

wherein $R^{13a}$-$R^{14d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl) alkylcarbonylamino, (cycloheteroalkyl) alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

12. A compound of claim 11, wherein each of $R^2$-$R^5$, $R^{7a}$-$R^{9b}$, $R^{11a}$, $R^{11b}$, and $R^{13a}$-$R^{14d}$ is hydrogen.

13. A compound of claim 12, wherein Y is $NR^{12}$ or O.

14. A compound of claim 13, wherein Y is $NR^{12}$, and $R^{10}$ and $R^{12}$ are selected independently from the group consisting of: hydrogen, or optionally substituted alkyl, alkyloxycarbonyl, alkylsulfonyl, cycloalkylsulfonyl, and alkylaminosulfonyl.

15. A compound of claim 13, wherein Y is O.

16. A compound of claim 1, wherein m is 2, such that $X^1$ is $(CR^{11}R^{11'})_2$, thereby defining $X^1$ as $(CR^{11a}R^{11b})(CR^{11c}R^{11d})$, said compound having the structure:

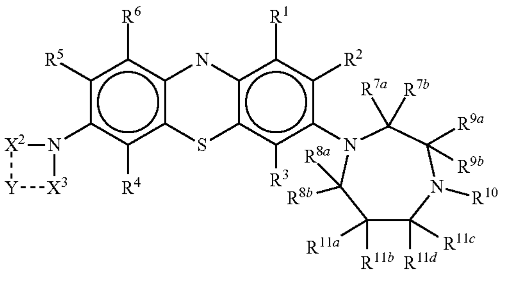

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

17. A compound of claim 16, wherein Y is not present, said compound having the structure:

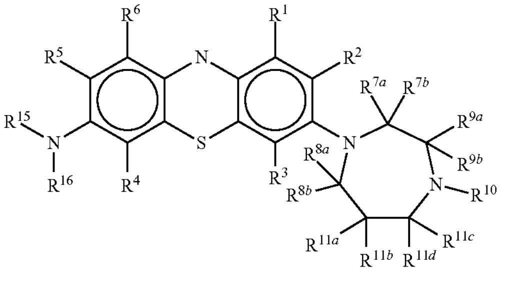

wherein $R^{11a}$-$R^{11d}$ selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl)alkylcarbonylamino, (cycloheteroalkyl)alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

18. A compound of claim 16, wherein Y is present, said compound having the structure:

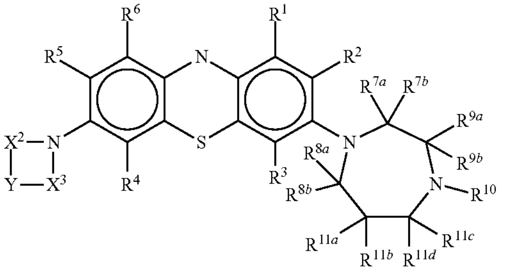

wherein $R^{11a}$-$R^{11d}$ are selected independently from the group consisting of: hydrogen, halo, cyano, nitro, thio, amino, carboxy, formyl, and optionally substituted alkyl, alkylcarbonyloxy, arylcarbonyloxy, heteroarylcarbonyloxy, cycloalkylcarbonyloxy, cycloheteroalkylcarbonyloxy, aralkylcarbonyloxy, heteroaralkylcarbonyloxy, (cycloalkyl)alkylcarbonyloxy, (cycloheteroalkyl)alkylcarbonyloxy, alkylcarbonyl, arylcarbonyl, heteroarylcarbonyl, cycloalkylcarbonyl, cycloheteroalkylcarbonyl, aralkylcarbonyl, heteroaralkylcarbonyl, (cycloalkyl)alkylcarbonyl, (cycloheteroalkyl)alkylcarbonyl, alkylaminocarbonyl, arylaminocarbonyl, aralkylaminocarbonyl, heteroarylaminocarbonyl, heteroaralkylaminocarbonyl, alkylcarbonylamino, arylcarbonylamino, heteroarylcarbonylamino, cycloalkylcarbonylamino, cycloheteroalkylcarbonylamino, aralkylcarbonylamino, heteroaralkylcarbonylamino, (cycloalkyl) alkylcarbonylamino, (cycloheteroalkyl) alkylcarbonylamino, dialkylamino, arylamino, diarylamino, aralkylamino, diaralkylamino, heteroarylamino, diheteroarylamino, heteroaralkylamino, diheteroaralkylamino, alkylsulfonyl, arylsulfonyl, heteroarylsulfonyl, cycloalkylsulfonyl, aralkylcarbonylthiooxy, carbonylthio, heteroaralkylcarbonylthio, (cycloalkyloxy)carbonylthio, (cycloheteroalkyl)alkylcarbonylthio, alkyloxycarbonyl, aryloxycarbonyl, heteroaryloxycarbonyl, cycloalkyloxycarbonyl, cycloheteroalkyloxycarbonyl, aralyoxycarbonyloxloxycarbonyl, heteroaralkyloxycarbonyl, (cycloalkyl)alkyloxycarbonyl, (cycloheteroalkyl)alkyloxycarbonyl, iminoalkyl, iminocycloalkyl, iminocycloheteroalkyl, iminoaralkyl, iminoheteroaralkyl, (cycloalkyl)iminoalkyl, and (cycloheteroalkyl)iminoalkyl.

19. A method for treating a viral disease in a mammal afflicted with such disease, comprising administering to such mammal a therapeutically effective amount of the compound of claim 1 wherein said viral disease is influenza, Adenovirus, Human Corona Virus, Herpes Simplex Virus, Rhinovirus, Respiratory Syntactical Virus, Hepatitis C Virus, Human Immunodeficiency Virus, Monkey Pox Virus, Rabies Virus, Dengue Virus, Easter Equine Encephalitis Virus, Venezuelan Equine Encephalitis Virus, Wester Equine Encephalitis Virus, West Nile Virus, Chikungunya Virus, Ebola Virus, or Marburg Virus.

20. The method of claim 19, wherein said viral disease is an etiological component of a respiratory syndrome selected from the group consisting of: bronchiolitis, the common cold, croup, influenza, and pneumonia.

21. A compound of claim 1, which is 3-(diethylamino)-1-ethyl-7-(piperazin-1-yl)phenothiazin-5-ium.

22. A compound of claim 1, which is 3-(1,4-diazepan-1-yl)-7-(dimethylamino)-1,9-diethylphenothiazin-5-ium.

23. A compound of claim 1, which is 3-(4-(cyclopropylsulfonyl)piperazin-1-yl)-7-(dimethylamino)-1,9-diethylphenothiazin-5-ium.

24. A compound of claim 1, which is 3,7-di(4-methylpiperazin-1-yl)-1-t-butylphenothiazin-5-ium.

25. A compound of claim 1, which is 1,9-dichloro-3-(piperazin-1-yl)-7-(pyrrolidin-1-yl)phenothiazin-5-ium.

26. A compound of claim 1, which is 3,7-(di(4-methylpiperazin-1-yl))-1-ethyl-9-methylphenothiazin-5-ium.

27. A compound of claim 1, which is 3,7-di(1,4-diazepan-1-yl)-1-ethyl-9-methylphenothiazin-5-ium.

28. A compound of claim 1, which is 3-(dimethylamino)-1-ethyl-9-methyl-7-(4-(trifluoromethylsulfonyl)piperazin-1-yl)phenothiazin-5-ium.

29. A compound of claim 1, which is 3,7-di(1,4-diazepan-1-yl)-1-trifluoromethylphenothiazin-5-ium.

30. A compound of claim 1, which is a member selected from 3-amino-7-(4-isopropylpiperazin-1-yl)-1,9-dimethylphenothiazin-5-ium, 3-amino-1,9-dimethyl-7-(4-(methylsulfonyl)piperazin-1-yl)phenothiazin-5-ium, 3-amino-1,9-dimethyl-7-(4-(trifluoromethylsulfonyl)piperazin-1-yl) phenothiazin-5-ium, and 3-amino-7-(4-(isopropylsulfonyl) piperazin-1-yl)-1,9-dimethylphenothiazin-5-ium.

31. A compound of claim 1, which is a member selected from 7-(4-(tert-butoxycarbonyl)piperazin-1-yl)-1-chloro-3-(diethylamino)phenothiazin-5-ium, 1-chloro-3-(diethylamino)-7-(piperazin-1-yl)phenothiazin-5-ium, 7-(4-(tert-butoxycarbonyl)piperazin-1-yl)-3-(diethylamino)-1-ethylphenothiazin-5-ium, 3-(diethylamino)-1-ethyl-7-(piperazin-1-yl)phenothiazin-5-ium, 3-(bis(2-methoxyethyl) amino)-7-(4-(tertbutoxycarbonyl)piperazin-1-yl)-1-ethylphenothiazin-5-ium, and 3-(bis(2-methoxyethyl) amino)-1,9-dichloro-7-(piperazin-1-yl)phenothiazin-5-ium.

32. A compound of claim 1, which is a member selected from 1,9-dichloro-3,7-di(piperazin-1-yl)phenothiazin-5-ium, 1-trifluoromethyl-3,7-di(4-methylpiperazin-1-yl)phenothiazin-5-ium, 3,7-(di(4-Boc-piperazin-1-yl))-1-trifluoromethylphenothiazin-5-ium, 3,7-dipiperazinyl-1-trifluoromethylphenothiazin-5-ium, 3,7-di(4-methylpiperazin-1-yl)-1-n-butylphenothiazin-5-ium, 3,7-di (4-methylpiperazin-1-yl)-1-methylphenothiazin-5-ium, 1-(tert-butyl)-3,7-bis(4-methylpiperazin-1-yl)phenothiazin-5-ium, and 3,7-di(4-methylpiperazin-1-yl)-1-isopropylphenothiazin-5-ium.

33. A compound of claim 1, which is a member selected from 3-(dimethylamino)-1,9-dimethyl-7-(4-methylpiperazin-1-yl)phenothiazin-5-ium, 3-(4-(tert-butoxycarbonyl) piperazin-1-yl)-7-(dimethylamino)-1,9-dimethylphenothiazin-5-ium, 3-(dimethylamino)-1,9-dimethyl-7-(piperazin-1-yl)phenothiazin-5-ium, 3,7-bis(4-(tert-butoxycarbonyl) piperazin-1-yl)-1,9-dimethylphenothiazin-5-ium, 3-(butyl (methyl)amino)-7-(4-(2-methoxyethyl)piperazin-1-yl)-1,9-dimethylphenothiazin-5-ium, 3-(4-(cyclopropylsulfonyl) piperazin-1-yl)-7-(dimethylamino)-1,9-dimethylphenothiazin-5-ium, 3-(dimethylamino)-7-(4-(isopropylsulfonyl)piperazin-1-yl)-1,9-dimethylphenothiazin-5-ium, 3-(dimethylamino)-1,9-dimethyl-7-(4-(2,2,2-trifluoroethylsulfonyl)piperazin-1-yl) phenothiazin-5-ium, 4-carboxy-3-(dimethylamino)-1,9-dimethyl-7-(4-methylpiperazin-1-yl)phenothiazin-5-ium, 4-carboxy-7-(dimethylamino)-1,9-dimethyl-3-(4-methylpiperazin-1-yl)phenothiazin-5-ium, 3-(4-(cyclopropylsulfonyl)piperazin-1-yl)-7-(dimethylamino)-1-isopropyl-9-methylphenothiazin-5-ium, 3-(diethylamino)-1,9-dimethyl-7-(4-(methylsulfonyl)piperazin-1-yl)phenothiazin-5-ium, 3-(diethylamino)-1,9-dimethyl-7-(piperazin-1-yl)phenothiazin-5-ium, 3-(diethylamino)-7-(4-isopropylpiperazin-1-yl)-1,9-dimethylphenothiazin-5-ium, 3-(diethylamino)-7-(4-isopropylpiperazin-1-yl)-1,9-dimethylphenothiazin-5-ium, 1,9-diethyl-3-dimethylamino-7-[4-isopropylpiperazinyl]-phenothiazinium, 3-(butyl(methyl)amino)-1,9-dimethyl-7-(4-methylpiperazin-1-yl)phenothiazin-5-ium, 3-(dimethylamino)-1,9-diethyl-7-((4-trifluoromethylsulfonyl) piperazin-1-yl)phenothiazin-5-ium, 3-(4-(cyclopentylsulfonyl)piperazin-1-yl)-7-(dimethylamino)-1,9-diethylphenothiazin-5-ium, 3-(dimethylamino)-9-ethyl-1-isopropyl-7-(4-isopropylpiperazin-1-yl)phenothiazin-5-ium, 3-(butyl(methyl)amino)-7-((4-cyclopropylsulfonyl)piperazin-1-yl)-1,9-diethylphenothiazin-5-ium, 3-(4-cyclopentylpiperazin-1-yl)-7-(dimethylamino)-1,9-diethylphenothiazin-5-ium, 3-(dimethylamino)-1,9-diethyl-7-(4-(2-methoxyethyl)piperazin-1-yl)phenothiazin-5-ium, 3-(4-(cyclopropylsulfonyl)piperazin-1-yl)-7-(dimethylamino)-1-ethyl-9-isopropylphenothiazin-5-ium, 3-(dimethylamino)-9-ethyl-1-isopropyl-7-((4-trifluoromethylsulfonyl)piperazin-1-yl)phenothiazin-5-ium, 3-(dimethylamino)-7-(4-(N,N- dimethylsulfamoyl)piperazin-1-yl)-1,9-diethylphenothiazin-5-ium, 3-(4-(cyclopropylsulfonyl)piperazin-1-yl)-7-(dimethylamino)-1,9-diethylphenothiazin-5-ium, 3-((4-tert-butylcarbamoyl)piperazin-1-yl)-7-(dimethylamino)-1,9-diethylphenothiazin-5-ium, 3-(4-butylpiperazin-1-yl)-7-(dimethylamino)-1,9-diethylphenothiazin-5-ium, 3-(4-acetylpiperazin-1-yl)-7-(methyl(n-butyl)amino)-1,9-dimethylphenothiazin-5-ium, 3-(4-boc-piperazin-1-yl)-7-(methyl(n-butyl)amino)-1,9-dimethylphenothiazin-5-ium, 3-(piperazin-1-yl)-7-(methyl(n-butyl)amino)-1,9-dimethylphenothiazin-5-ium, 3-(dimethylamino)-1-ethyl-9-methyl-7-(4-methylpiperazin-1-yl)-phenothiazin-5-ium, 3-(dimethylamino)-1-ethyl-9-methyl-7-(4-(trifluoromethylsulfonyl)piperazin-1-yl)phenothiazin-5-ium, 3-(4-(cyclopropylsulfonyl)piperazin-1-yl)-7-(dimethylamino)-9-ethyl-1-methyl-phenothiazin-5-ium, and 3-(bis(2-methoxyethyl)amino)-1-ethyl-9-methyl-7-(4-methylpiperazin-1-yl)phenothiazin-5-ium.

34. A compound of claim 1, which is a member selected from 1,9-dimethyl-3,7-bis(4-methylpiperazin-1-yl)phenothiazin-5-ium, 3,7-bis(4-(tert-butoxycarbonyl)piperazin-1-yl)-1,9-dimethylphenothiazin-5-ium, 3,7-bis[4-(2-methoxyethyl)piperazin-1-yl]-1,9-dimethyl-phenothiazin-5-ium, 1,9-dimethyl-3,7-bis(4-sulfamoylpiperazin-1-yl)phenothiazin-5-ium, 3,7-bis(4-isopropylpiperazin-1-yl)-1,9-dimethylphenothiazin-5-ium, 3, 7 bis(4(cyclopropanecarbonyl)piperazin-1-yl)-1,9-diethylphenothiazin-5-ium, 3,7-bis(4-(cyclopropylsulfonyl)piperazin-1-yl)-1,9-diethyl-phenothiazin-5-ium, 3,7-di(4-acetylpiperazin-1-yl)-1,9-dimethylphenothiazin-5-ium, and 3,7-(di(4-methylpiperazin-1-yl))-1-ethyl-9-methylphenothiazin-5-ium.

35. A compound of claim 1, which is a member selected from 1,9-dimethyl-3-morpholino-7-(4-sulfamoylpiperazin-1-yl)phenothiazin-5-ium, 3-((2R,6S)-2,6-dimethylmorpholino)-1,9-dimethyl-7-(4-sulfamoylpiperazin-1-yl)phenothiazin-5-ium, 3-((2R,6R)-2,6-dimethylmorpholino)-1,9-dimethyl-7-(4-sulfamoylpiperazin-1-yl)phenothiazin-5-ium, 1,9-diethyl-3-morpholino-7-(4-sulfamoylpiperazin-1-yl)phenothiazin-5-ium, 3-(4-(tert-butoxycarbonyl)-3-(methoxycarbonyl)-piperazin-1-yl)-1,9-diethyl-7-morpholinophenothiazin-5-ium, 3-(4-boc-piperazin-1-yl)-1-ethyl-9-methyl-7-morpholino-phenothiazin-5-ium, and 1-ethyl-9-methyl-7-morpholino-3-(piperazin-1-yl)-phenothiazin-5-ium.

36. A compound of claim 1, which is a member selected from 3-(azetidin-1-yl)-7-(4-(isopropylsulfonyl)piperazin-1-yl)-1,9-dimethylphenothiazin-5-ium, 1,9-dimethyl-3-(pyrrolidin-1-yl)-7-(4-(2,2,2-trifluoroethylsulfonyl)piperazin-1-yl)phenothiazin-5-ium, and 3-(4-(cyclopropylsulfonyl)piperazin-1-yl)-9-ethyl-1-methyl-7-(pyrrolidin-1-yl)-phenothiazin-5-ium.

37. A compound of claim 1, which is a member selected from 3-(4-(cyclopropylsulfonyl)-1,4-diazepan-1-yl)-7-(dimethylamino)-1,9-diethylphenothiazin-5-ium, 3-(dimethylamino)-1,9-diethyl-7-((methylsulfonyl)-1,4-diazepan-1-yl)phenothiazin-5-ium, 3-(dimethylamino)-1,9-diethyl-7-(4-(ethylsulfonyl)-1,4-diazepan-1-yl)phenothiazin-5-ium, 3-(4-(tert-butylcarbamoyl)-1,4-'diazepan-1-yl)-7-(dimethylamino)-1,9-diethylphenothiazin-5-ium, 3-(dimethylamino)-1,9-diethyl-7-(4-sulfamoyl-1,4-diazepan-1-yl)phenothiazin-5-ium, 3-(dimethylamino)-1,9-diethyl-7-(4-(isopropylsulfonyl)-1,4-diazepan-1-yl)phenothiazin-5-ium, 3-(dimethylamino)-1,9-diethyl-7-(4-(methylbut-2-enyl)-1,4-diazepan-1-yl)phenothiazin-5-ium, 3-(4-(tert-butoxycarbonyl)-1,4-diazepan-1-yl)-7-(dimethylamino)-1,9-diethylphenothiazin-5-ium, and 3-(1,4-diazepan-1-yl)-7-(dimethylamino)-1,9-diethylphenothiazin-5-ium.

38. A compound of claim 1, which is a member selected from 3,7-di(1,4-diazepan-1-yl)-1,9-dimethylphenothiazin-5-ium, 3-(1,4-diazepan-1-yl)-1,9-diethyl-7-(4-ureidopiperidin-1-yl)phenothiazin-5-ium, 3,7-di(1,4-diazepan-1-yl)-1,9-diethylphenothiazin-5-ium, 3-(4-(tert-butoxycarbonyl)-1,4-diazepan-1-yl)-1,9-diethyl-7-(2-methylpyrrolidin-1-yl)phenothiazin-5-ium, 3-(1,4-diazepan-1-yl)-1,9-diethyl-7-(2-methylpyrrolidin-1-yl)phenothiazin-5-ium, 3,7-bis(4-(tert-butoxycarbonyl)-1,4-diazepan-1-yl)-1,9-diethylphenothiazin-5-ium, 1-ethyl-9-methyl-7-((4-methylsulfonyl)-1,4-diazepan-1-yl)-3-(pyrrolidin-1-yl)-phenothiazin-5-ium, 3,7-bis(4-boc-1,4-diazepan-1-yl)-1-ethyl-9-methyl-phenothiazin-5-ium, 3-(4-boc-1,4-diazepan-1-yl)-1-ethyl-9-methyl-7-(pyrrolidin-1-yl)-phenothiazin-5-ium, 3,7-di(1,4-diazepan-1-yl)-1-ethyl-9-methyl-phenothiazin-5-ium, and 3-(1,4-diazepan-1-yl)-1-ethyl-9-methyl-7-(pyrrolidin-1-yl)-phenothiazin-5-ium.

39. The method of claim 19, wherein said viral disease is influenza.

40. The method of claim 19, wherein said viral disease is Human Immunodeficiency Virus.

41. A compound of claim 1, which is 7-(4-methylpiperazin-1-yl)-3-(pyrrolidin-1-yl)-1-(trifluoromethyl)phenothiazin-5-ium.

* * * * *

UNITED STATES PATENT AND TRADEMARK OFFICE

CERTIFICATE OF CORRECTION

PATENT NO. : 8,785,434 B2
APPLICATION NO. : 13/099006
DATED : July 22, 2014
INVENTOR(S) : Kurt et al.

It is certified that error appears in the above-identified patent and that said Letters Patent is hereby corrected as shown below:

Specification

Column 1, line 14, insert the following:

-- STATEMENT AS TO RIGHTS TO INVENTIONS MADE UNDER FEDERALLY SPONSORED RESEARCH OR DEVELOPMENT

This invention was made with Government support under Grant Number W911NF-11-C-0059, awarded by the Defense Threat Reduction Agency (DTRA). The Government has certain rights in the invention. --

Signed and Sealed this
Fifth Day of July, 2016

Michelle K. Lee
*Director of the United States Patent and Trademark Office*